(12) United States Patent
Shan et al.

(10) Patent No.: US 7,468,439 B2
(45) Date of Patent: Dec. 23, 2008

(54) ALKYLENE BRIDGED SULTAM COMPOUNDS USEFUL AS MODULATORS OF NUCLEAR HORMONE RECEPTOR FUNCTION

(75) Inventors: Weifang Shan, Princeton, NJ (US); James Aaron Balog, Lambertville, NJ (US); Andrew James Nation, Scotch Plains, NJ (US); Ashvinikumar V. Gavai, Princeton Junction, NJ (US); Wen-Ching Han, Newtown, PA (US); Mark E. Salvati, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/850,070

(22) Filed: Sep. 5, 2007

(65) Prior Publication Data

US 2008/0090883 A1   Apr. 17, 2008

Related U.S. Application Data

(60) Provisional application No. 60/953,217, filed on Aug. 1, 2007, provisional application No. 60/842,541, filed on Sep. 6, 2006.

(51) Int. Cl.
C07D 275/04   (2006.01)
A61K 31/425   (2006.01)

(52) U.S. Cl. ..................... 548/207; 514/373
(58) Field of Classification Search .......... 548/207; 514/373
See application file for complete search history.

(56) References Cited

U.S. PATENT DOCUMENTS

| | | | |
|---|---|---|---|
| 5,296,496 A | 3/1994 | Desai et al. | |
| 6,670,386 B2 | 12/2003 | Sun et al. | |
| 6,960,474 B2 | 11/2005 | Salvati et al. | |
| 7,001,911 B2 | 2/2006 | Salvati et al. | |
| 7,087,636 B2 | 8/2006 | Salvati et al. | |
| 7,141,578 B2 | 11/2006 | Salvati et al. | |
| 2005/0187267 A1 | 8/2005 | Hamann et al. | |
| 2005/0187273 A1* | 8/2005 | Salvati et al. | 514/373 |
| 2005/0197367 A1 | 9/2005 | Li et al. | |
| 2006/0111424 A1 | 5/2006 | Salvati et al. | |
| 2007/0088039 A1 | 4/2007 | Balog et al. | |

FOREIGN PATENT DOCUMENTS

EP   0220051   4/1987

OTHER PUBLICATIONS

Beer, R. J. S., et al., "Studies on 5-Benzoyl-3-Isothiazolinones", Tetrahedron, vol. 37(22), pp. 3867-3870 (1981).

Harned, A. M., et al., "Ring-Opening Metathesis Phase-Trafficking (ROMpt) Synthesis: Multistep on Soluble ROM Supports", Organic Letters, vol. 5(1), pp. 15-18 (2003).
Ho, K. F., et al., "Synthesis and Diels-Alder reactions of α,β-unsaturated-γ-sultams", Tetrahedron Letters, vol. 42, pp. 3121-3124 (2001).
Jiang L-S., et al., "Synthesis and Diels-Alder Reactions of Prop-1-ene-1,3-sultone, and Chemical Transformations of the Diels-Alder Adducts", Tetrahedron, vol. 55, pp. 2245-2262 (1999).
Lee. A. W. M., et al., "Ruthenium catalyzed asymmetric dihydroxylation with sultams as chiral auxiliaries", Tetrahedron: Asymmetry, vol. 10, pp. 1421-1424 (1999).
Lee, A. W. M., et al., "Synthesis and Diels-Alder reactions of α,β-unsaturated γ-sultone", Chem. Commun., vol. 6, pp. 611-612 (1997).
Lin, J., et al., "Asymmetric synthesis of 1,3- and 1,3,4-substituted pyrrolidines", Tetrahedron Letters, vol. 41, pp. 2949-2951 (2000).
Lin, J., et al., "Asymmetric Alkylation Mediated by Tricyclic Chiral Sultam Auxiliaries", Tetrahedron, vol. 55, 13983-13998 (1999).
Wanner, J., et al., "A dual metathesis route to oligomeric sulfonamides", Tetrahedron Letters, vol. 43, pp. 917-921 (2002).
Beilstein Abstract, BRN: 5129935.
Beilstein Abstract, BRN: 9335197.
Beilstein Abstract, BRN: 9350372.
Beilstein Abstract, BRN: 9359394.
Beilstein Abstract, BRN: 9362313.
Beilstein Abstract, BRN: 9364304.
Beilstein Abstract, BRN: 9366506.
Beilstein Abstract, BRN: 9367324.
Beilstein Abstract, BRN: 9368944.
Beilstein Abstract, BRN: 9369766.
Beilstein Abstract, BRN: 9371255.

* cited by examiner

*Primary Examiner*—Kamal A Saeed
*Assistant Examiner*—Kristin Bianchi
(74) *Attorney, Agent, or Firm*—Gary D. Greenblatt

(57) ABSTRACT

Disclosed are sultam compounds of Formula (I)

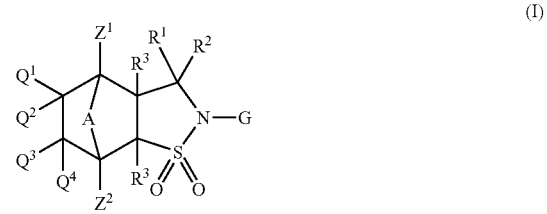

(I)

or a pharmaceutically-acceptable salt thereof. Also disclosed are methods of using such compounds in the treatment of at least one nuclear hormone receptor-associated condition, such as, for example, cancer and immune disorders, and at least one pharmaceutical composition comprising such compounds.

12 Claims, No Drawings

ALKYLENE BRIDGED SULTAM COMPOUNDS USEFUL AS MODULATORS OF NUCLEAR HORMONE RECEPTOR FUNCTION

FIELD OF THE INVENTION

Disclosed is at least one sultam compound; at least one method of using at least one sultam compound disclosed herein to treat at least one nuclear hormone receptor-associated condition; and at least one pharmaceutical composition comprising at least one sultam compound disclosed herein.

BACKGROUND OF THE INVENTION

Nuclear hormone receptors (NHRs) constitute a super-family of ligand-dependent and sequence-specific transcription factors. Members of the NHR family influence transcription either directly via specific binding to promoter target genes, or indirectly via protein-protein interactions with other transcription factors. The NHR family includes, for example, conventional NHRs, such as, for example, cortisol, aldosterone, estrogen, progesterone, testosterone, dihydrotestosterone, vitamin D3, thyroid hormone, and retinoic acid; and orphan NHRs that either interact with ubiquitous ligands that have not been identified, or do not need to bind ligand to exert activity.

Steroid binding NHRs (SB-NHRs) are a sub-family of NHRs that utilize steroid based ligands. Exemplary SB-NHRs include, but are not limited to, for example, the androgen receptor (AR); the estrogen receptor (ER); the progesterone receptor (PR); the glucocorticoid receptor (GR); the mineralocorticoid receptor (MR); the aldosterone receptor (ALDR); and the steroid and xenobiotic receptor (SXR).

In general, the endogenous ligands that bind to SB-NHRs have a common steroid core. Exemplary endogenous ligands, include, but are not limited to, for example, cortisol, aldosterone, estrogen, progesterone, testosterone, and dihydrotestosterone. The specificity with which an endogenous ligand binds to a particular SB-NHR depends on the differential substitution about the steroid core of such ligand.

Non-endogenous ligands, such as, for example, synthetically or food derived steroidal or non-steroidal SB-NHR antagonists and/or agonists have been developed to treat a variety of medical conditions. Synthetically derived SB-NHR antagonists and/or agonists include, but are not limited to, for example, RU486, which is an agonist of the PR; flutamide, which is an antagonist of the AR; and tamoxifen, which is a partial agonist/partial antagonist of the ER. Food-derived SB-NHR antagonists and/or agonists include, but are not limited to, for example, flavanoid phytoestrogens found in soy.

Non-endogenous SB-NHR antagonists and/or agonists can be synthetically engineered by first identifying a core structure capable of mimicking the core system of the endogenous ligand of interest, and subsequently differentially substituting about the core of the mimic to obtain an agent with selectivity for the SB-NHR of interest. Differential substitution about the steroid mimic core can result in a series of high affinity agonists and antagonists with specificity for, for example, ER versus PR versus AR versus GR versus MR.

The sultam compounds disclosed herein may mimic at least one endogenous ligand capable of binding to at least one SB-NHR and/or at least one other NHR, and therefore may be useful to modulate the function of at least one SB-NHR and/or at least one other NHR.

SUMMARY OF THE INVENTION

Described herein are compounds of Formula (I):

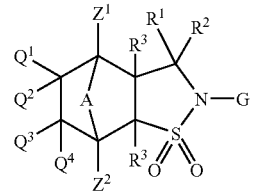

or a pharmaceutically-acceptable salt thereof;

wherein the symbols have the following meanings and are, for each occurrence, independently selected:

G is aryl, substituted aryl, heteroaryl, or substituted heteroaryl, wherein G is attached to the N atom of the core rings via a carbon atom of G;

A is $CR^4R^5$, $C(=O)$, $C(OR^4)R^5$, $CR^4R^5CR^4R^5$, $CR^4R^5C(=O)$, or $CR^4R^5C(OR^4)R^5$;

$Z^1$ and $Z^2$ are each independently H, halogen, CN, alkyl, substituted alkyl, alkenyl, substituted alkenyl, cycloalkyl, substituted cycloalkyl, cycloalkylalkyl, substituted cycloalkylalkyl, aryl, substituted aryl, arylalkyl, substituted arylalkyl, heterocyclo, substituted heterocyclo, heterocycloalkyl, substituted heterocycloalkyl, $-C(=O)OR^6$, $-C(=O)R^6$, $-C(=O)NR^6R^7$, $-OC(=O)NR^6R^7$, $-OC(=O)R^6$, $-OR^6$, $-C(=N-CN)NR^6R^7$, $-NR^6C(=O)OR^7$, $-NR^6C(=O)R^7$, $-SO_2R^7$, $-NR^6R^7$, $-NR^6SO_2R^7$, $-NR^6SO_2NR^6R^7$, and/or $-NR^6C(=O)NR^6R^7$;

$Q^1$, $Q^2$, $Q^3$, and $Q^4$ are each independently H, halogen, CN, alkyl, substituted alkyl, aryl, substituted aryl, heterocyclo, substituted heterocyclo, $-OR^6$, $-NR^6R^7$, $-NR^6C(=O)OR^7$, $-OC(=O)NR^6R^7$, $-NR^6SO_2R^7$, $-SO_2R^7$, $-OSO_2R^7-SO_2NR^6R^7$, $-NR^6SO_2NR^6R^7$, $-SR^9$, $-SOR^9$, $-C(=O)NR^6R^7$, $-C(=O)OR^6$, $-C(=O)R^6$, $-NR^6C(=O)R^7$, and/or $-NR^6C(=O)NR^6R^7$; or $Q^1$ and $Q^2$ together form 0 and/or $Q^3$ and $Q^4$ together form 0; or $Q^2$ and $Q^4$ together form $CR^6R^7$, O, $NR^3$, or a carbon-carbon bond;

$R^1$ and $R^2$ are each independently H, alkyl, substituted alkyl, cycloalkyl, substituted cycloalkyl, cycloalkylalkyl, substituted cycloalkylalkyl, alkenyl, substituted alkenyl, arylalkyl, substituted arylalkyl, heterocycloalkyl, substituted heterocycloalkyl, aryl, substituted aryl, heteroaryl, substituted heteroaryl, OH, and/or CN;

each $R^3$ is independently H, alkyl, substituted alkyl, alkenyl, substituted alkenyl, cycloalkyl, substituted cycloalkyl, cycloalkylalkyl, substituted cycloalkylalkyl, $-COR^6$, $-CONR^6R^7$, $-OR^6$, $-C(=O)OR^6$, $-OC(=O)NR^6R^7$, $-SO_2R^7$, $-NR^6C(=O)R^7$, $-NR^6SO_2R^7$, $-NR^6C(=O)NR^6R^7$, $-NR^6C(=O)OR^7$, and/or $-NR^6R^7$;

each $R^4$ and each $R^5$ are independently H, alkyl, substituted alkyl, cycloalkyl, substituted cycloalkyl, cycloalkylalkyl, substituted cycloalkylalkyl, arylalkyl, substituted arylalkyl, heterocycloalkyl, substituted heterocycloalkyl, aryl, substituted aryl, heteroaryl, substituted heteroaryl, and/or CN; or $R^4$ and $R^5$ together with the carbon atom to which they are attached form a cycloalkyl ring;

each $R^6$ and each $R^7$ are independently H, alkyl, substituted alkyl, cycloalkyl, substituted cycloalkyl, cycloalkylalkyl, substituted cycloalkylalkyl, arylalkyl, substituted arylalkyl, heterocycloalkyl, substituted heterocycloalkyl, aryl, substituted aryl, heteroaryl, substituted heteroaryl, and/or CN;

$R^8$ is H, alkyl, substituted alkyl, cycloalkyl, substituted cycloalkyl, cycloalkylalkyl, substituted cycloalkylalkyl, —C(=O)$R^6$, —C(=O)N$R^6R^7$, —C(=O)O$R^6$, —SO$_2R^7$, —SO$_2$N$R^6R^7$, or —SO$_3R^7$; and each $R^9$ is independently H, alkyl, substituted alkyl, cycloalkyl, substituted cycloalkyl, cycloalkylalkyl, substituted cycloalkylalkyl, arylalkyl, substituted arylalkyl, heterocycloalkyl, substituted heterocycloalkyl, aryl, substituted aryl, heteroaryl, and/or substituted heteroaryl;

with the proviso that when $Q^2$ and $Q^4$ together form a carbon-carbon bond and $A^1$ is CH$_2$, then G is not a phenyl group substituted at the 4-position with an oxygen-substituted methylene group or —C(=O)O-alkyl.

Further described herein is at least one pharmaceutical composition comprising at least one compound of Formula (I) or a pharmaceutically acceptable salt thereof; at least one pharmaceutically acceptable carrier and/or diluent; and optionally at least one other anti-cancer agent.

Even further described herein is a method of modulating the function of at least one nuclear hormone receptor comprising administering to a patient in need thereof, an effective amount of at least one compound of Formula (I), or a pharmaceutically acceptable salt thereof.

Yet even further described herein is at least one method of treating at least one condition and/or at least one disorder comprising administering to a patient in need thereof, a therapeutically effective amount of at least one compound of Formula (I), or a pharmaceutically acceptable salt thereof; optionally administering either simultaneously or sequentially at least one other anti-cancer agent, and optionally administering either simultaneously or sequentially at least one other anti-cancer treatment.

DETAILED DESCRIPTION OF THE INVENTION

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Definitions of terms used in describing the invention are set forth hereinbelow. Unless otherwise indicated, the initial definition provided for a group or term applies each time such group or term is used individually or as part of another group.

Throughout the specification, groups and substituents thereof may be chosen by one skilled in the field to provide stable moieties and compounds.

The terms "alkyl" and "alk" refer to a straight or branched chain alkane (hydrocarbon) radical containing from 1 to 12 carbon atoms and preferably from 1 to 6 carbon atoms. Exemplary "alkyl" and/or "alk" groups include, but are not limited to, for example, methyl; ethyl; propyl; isopropyl; 1-methylpropyl; n-butyl, t-butyl; isobutyl; pentyl; hexyl; isohexyl; heptyl; 4,4-dimethylpentyl; diethylpentyl; octyl; 2,2,4-trimethylpentyl; nonyl; decyl; undecyl; and dodecyl.

The term "substituted alkyl" refers to an alkyl group substituted with at least one substituent, preferably 1 to 4 substituents, at any available and substitutable position. Exemplary substituents include, but are not limited to, for example, halo (e.g., a single halo substituent or multiple halo substituents forming, in the latter case, groups such as, for example, a perfluoroalkyl group or an alkyl group bearing CCl$_3$ or CF$_3$); alkoxy, alkylthio; hydroxyl; carboxy (i.e., —COOH); alkoxycarbonyl; alkylcarbonyloxy; CN; amino (i.e., —NH$_2$); alkylamino; dialkylamino; carbamoyl; substituted carbamoyl; carbamate; substituted carbamate; urea; substituted urea; amidinyl; substituted amidinyl; thiol (i.e., —SH); alkyl; aryl; substituted aryl; heterocycle; substituted heterocycle; cycloalkyl; substituted cycloalkyl; heterocycloalkyl; —S-aryl; —S-heterocycle; —S=O-aryl; —S=O-heterocycle; arylalkyl-O—; —S(O)$_2$-aryl; —S(O)$_2$-heterocycle; —NHS(O)$_2$-aryl; —NHS(O)$_2$-heterocycle; —NHS(O)$_2$NH-heterocycle; —NHS(O)$_2$NH-aryl; —O-aryl; —O-heterocycle; —NH-aryl; —NH-heterocycle; —NHC(=O)-aryl; —NHC(=O)-alkyl; —NHC(=O)-heterocycle; —OC(=O)-aryl; —OC(=O)-heterocycle; —NHC(=O)NH-aryl; —NHC(=O)NH-heterocycle; —OC(=O)O-alkyl; —OC(=O)O-aryl; —OC(=O)O-heterocycle; —OC(=O)NH-aryl; —OC(=O)NH-heterocycle; —NHC(=O)O-aryl; —NHC(=O)O-heterocycle; —NHC(=O)O-alkyl; —C(=O)NH-aryl; —C(=O)NH-heterocycle; —C(=O)O-aryl; —C(=O)O-heterocycle; —N(alkyl)S(O)$_2$-aryl; —N(alkyl)S(O)$_2$-heterocycle; —N(alkyl)S(O)$_2$NH-aryl; —N(alkyl)S(O)$_2$NH-heterocycle; —N(alkyl)-aryl; —N(alkyl)-heterocycle; —N(alkyl)C(=O)-aryl; —N(alkyl)C(=O)-heterocycle; —N(alkyl)C(=O)NH-aryl; N(alkyl)C(=O)NH-heterocycle; —OC(=O)N(alkyl)-aryl; —OC(=O)N(alkyl)-heterocycle; —N(alkyl)C(=O)O-aryl; —N(alkyl)C(=O)O-heterocycle; —C(=O)N(alkyl)-aryl; —C(=O)N(alkyl)-heterocycle; —NHS(O)$_2$N(alkyl)-aryl; —NHS(O)$_2$N(alkyl)-heterocycle; —NHP(O)$_2$N(alkyl)-aryl; —NHC(=O)N(alkyl)-aryl; —NHC(=O)N(alkyl)-heterocycle; —N(alkyl)S(O)$_2$N(alkyl)-aryl; —N(alkyl)S(O)$_2$N(alkyl)-heterocycle; —N(alkyl)C(=O)N(alkyl)-aryl; —N(alkyl)C(=O)N(alkyl)-heterocycle; and —Si(alkyl)$_3$. In the aforementioned exemplary substituents, in each instance, groups such as "alkyl", "aryl" and "heterocycle" can themselves be optionally substituted; for example, "alkyl" in the group "NHC(=O)O-alkyl" recited above can be optionally substituted so that both "NHC(=O)O-alkyl" and "NHC(=O)O-substituted alkyl" are exemplary substituents.

The term "lower alkyl" refers to an "alkyl" and/or "alk" group containing from 1 to 4 carbon atoms and preferably from 1 to 2 carbon atoms. When a subscript is used with reference to an alkyl or other group, the subscript refers to the number of carbon atoms the group may contain. For example, the term "$C_{0-4}$alkyl" includes a bond and an alkyl group containing 1 to 4 carbon atoms, and the term "$C_{1-4}$alkyl" refers to alkyl groups containing 1 to 4 carbon atoms. It is of import to note that although the term "lower alkyl" is encompassed within the definition of "alkyl" and/or "alk", the usage of the term "lower alkyl" is not intended to limit the definition of the term "alkyl" either explicitly or implicitly to a straight- or branched-chain alkane (hydrocarbon) radical containing from 5 to 12 carbon atoms. Exemplary lower alkyl groups include, but are not limited to, for example, methyl; ethyl; propyl; isopropyl; n-butyl; t-butyl; and isobutyl.

The term "substituted lower alkyl" refers to a lower alkyl substituted at any available and substitutable position with at least one substituted alkyl, lower alkyl, and/or substituent described above in defining the term "substituted alkyl" as an exemplary alkyl substituent.

The term "aryl" refers to cyclic aromatic hydrocarbon groups having from 1 to 5 aromatic rings, especially monocyclic or bicyclic groups, such as, for example, phenyl; biphenyl; or naphthyl. When the aryl group contains two or more aromatic rings (e.g., bicyclic, etc.), the aromatic rings may be joined at a single point (e.g., biphenyl), or fused (e.g., naphthyl and phenanthrenyl).

The term "substituted aryl" refers to an aryl substituted with at least one substituent, preferably 1 to 5 substituents, at any available and substitutable ring position, or where valence allows on any rings fused or attached thereto. Exemplary substituents include, but are not limited to, for example, nitro; cycloalkyl; substituted cycloalkyl; cycloalkenyl; substituted cycloalkenyl; alkyl-S(O)$_m$ (where m=0, 1 or 2); alkyl; substituted alkyl; aryl; halo (e.g., a single halo substituent or multiple halo substituents forming, in the latter case, groups such as, for example, a perfluoroalkyl group or an alkyl group bearing CCl$_3$ or CF$_3$); alkoxy; alkylthio; hydroxyl; carboxy (i.e., —COOH); alkoxycarbonyl; alkylcarbonyloxy; CN; amino (i.e., —NH$_2$); alkylamino; dialkylamino; carbamoyl; substituted carbamoyl; carbamate; substituted carbamate; urea; substituted urea; amidinyl; substituted amidinyl; thiol (i.e., —SH); heterocycle; substituted heterocycle; heterocycloalkyl; —S-aryl; —S-heterocycle; —S=O-aryl; —S=O-heterocycle; arylalkyl-O—; —S(O)$_2$-aryl; —S(O)$_2$-heterocycle; —NHS(O)$_2$-aryl; —NHS(O)$_2$-heterocycle; —NHS(O)$_2$NH-heterocycle; —NHS(O)$_2$NH-aryl; —O-aryl; —O-heterocycle; —NH-aryl; —NH-heterocycle; —NHC(=O)-aryl; —NHC(=O)-alkyl; —NHC(=O)-heterocycle; —OC(=O)-aryl; —OC(=O)-heterocycle; —NHC(=O)NH-aryl; —NHC(=O)NH-heterocycle; —OC(=O)O-alkyl; —OC(=O)O-aryl; —OC(=O)O-heterocycle; —OC(=O)NH-aryl; —OC(=O)NH-heterocycle; —NHC(=O)-aryl; —NHC(=O)O-heterocycle; —NHC(=O)O-alkyl; —C(=O)NH-aryl; —C(=O)NH-heterocycle; —C(=O)O-aryl; —C(=O)O-heterocycle; —N(alkyl)S(O)$_2$-aryl; —N(alkyl)S(O)$_2$-heterocycle; —N(alkyl)S(O)$_2$NH-aryl; —N(alkyl)S(O)$_2$NH-heterocycle; —N(alkyl)-aryl; —N(alkyl)-heterocycle; —N(alkyl)C(=O)-aryl; —N(alkyl)C(=O)-heterocycle; —N(alkyl)C(=O)NH-aryl; —N(alkyl)C(=O)NH-heterocycle; —OC(=O)N(alkyl)-aryl; —OC(=O)N(alkyl)-heterocycle; —N(alkyl)C(=O)O-aryl; —N(alkyl)C(=O)O-heterocycle; —C(=O)N(alkyl)-aryl; —C(=O)N(alkyl)-heterocycle; —NHS(O)$_2$N(alkyl)-aryl; —NHS(O)$_2$N(alkyl)-heterocycle; —NHP(O)$_2$N(alkyl)-aryl; —NHC(=O)N(alkyl)-aryl; —NHC(=O)N(alkyl)-heterocycle; —N(alkyl)S(O)$_2$N(alkyl)-aryl; —N(alkyl)S(O)$_2$N(alkyl)-heterocycle; —N(alkyl)C(=O)N(alkyl)-aryl; —N(alkyl)C(=O)N(alkyl)-heterocycle; —Si(alkyl)$_3$; and fused cyclic substituents, such as, for example, heterocyclo, cycloalkenyl, substituted heterocyclo, and/or cycloalkenyl substituents that fuse together to form, for example, a fluorenyl, tetrahydronapthalenyl, and/or dihydroindenyl substituent. In the aforementioned exemplary substituents, in each instance, groups such as "alkyl", "aryl" and "heterocycle" can themselves be optionally substituted; for example, "alkyl" in the group "NHC(=O)O-alkyl" recited above can be optionally substituted so that both "NHC(=O)O-alkyl" and "NHC(=O)O-substituted alkyl" are exemplary substituents.

The term "alkenyl" refers to a straight or branched chain hydrocarbon radical containing from 2 to 12 carbon atoms and at least one carbon-carbon double bond. Exemplary alkenyls include, but are not limited to, for example, ethenyl and allyl.

The term "substituted alkenyl" refers to an alkenyl substituted with at least one substituent, preferably 1 to 4 substituents, at any available point of attachment. Exemplary substituents include, but are not limited to, for example, substituted alkyl; alkenyl; and the substituents described above in defining the term "substituted alkyl" as exemplary alkyl substituents.

The term "cycloalkyl" refers to a fully saturated or partially saturated cyclic hydrocarbon group containing from 1 to 4 rings and 3 to 8 carbons per ring. Exemplary fully saturated cycloalkyl groups include, but are not limited to, for example, cyclopropyl, cyclobutyl, cyclopentyl, cyclohexyl, and cycloheptyl. Exemplary partially saturated cycloalkyl groups include, but are not limited to, for example, cyclobutenyl, cyclopentenyl, and cyclohexenyl.

The term "substituted cycloalkyl" refers to a cycloalkyl substituted with at least one substituent, preferably 1 to 4 substituents, at any available point of attachment. Exemplary substituents include, but are not limited to, for example, nitro; halo (e.g., a single halo substituent or multiple halo substituents forming, in the latter case, groups such as, for example, a perfluoroalkyl group or an alkyl group bearing CCl$_3$ or CF$_3$); alkoxy, alkylthio; hydroxyl; carboxy (i.e., —COOH); alkoxycarbonyl; alkylcarbonyloxy; CN; amino (i.e., —NH$_2$); alkylamino; dialkylamino; carbamoyl; substituted carbamoyl; carbamate; substituted carbamate; urea; substituted urea; amidinyl; substituted amidinyl; thiol (i.e., —SH); alkyl; substituted alkyl; aryl; heterocycle; cycloalkyl; heterocycloalkyl; —S-aryl; —S-heterocycle; —S=O-aryl; —S=O-heterocycle; arylalkyl-O—; —S(O)$_2$-aryl; —S(O)$_2$-heterocycle; —NHS(O)$_2$-aryl; —NHS(O)$_2$-heterocycle; —NHS(O)$_2$NH-heterocycle; —NHS(O)$_2$NH-aryl; —O-aryl; —O-heterocycle; —NH-aryl; —NH-heterocycle; —NHC(=O)-aryl; —NHC(=O)-alkyl; —NHC(=O)-heterocycle; —OC(=O)-aryl; —OC(=O)-heterocycle; —NHC(=O)NH-aryl; —NHC(=O)NH-heterocycle; —OC(=O)O-alkyl; —OC(=O)O-aryl; —OC(=O)O-heterocycle; —OC(=O)NH-aryl; —OC(=O)NH-heterocycle; —NHC(=O)O-aryl; —NHC(=O)O-heterocycle; —NHC(=O)O-alkyl; —C(=O)NH-aryl; —C(=O)NH-heterocycle; —C(=O)O-aryl; —C(=O)O-heterocycle; —N(alkyl)S(O)$_2$-aryl; —N(alkyl)S(O)$_2$-heterocycle; —N(alkyl)S(O)$_2$NH-aryl; —N(alkyl)S(O)$_2$NH-heterocycle; —N(alkyl)-aryl; —N(alkyl)-heterocycle; —N(alkyl)C(=O)-aryl; —N(alkyl)C(=O)-heterocycle; —N(alkyl)C(=O)NH-aryl; N(alkyl)C(=O)NH-heterocycle; —OC(=O)N(alkyl)-aryl; —OC(=O)N(alkyl)-heterocycle; —N(alkyl)C(=O)O-aryl; —N(alkyl)C(=O)O-heterocycle; —C(=O)N(alkyl)-aryl; —C(=O)N(alkyl)-heterocycle; —NHS(O)$_2$N(alkyl)-aryl; —NHS(O)$_2$N(alkyl)-heterocycle; —NHP(O)$_2$N(alkyl)-aryl; —NHC(=O)N(alkyl)-aryl; —NHC(=O)N(alkyl)-heterocycle; —N(alkyl)S(O)$_2$N(alkyl)-aryl; —N(alkyl)S(O)$_2$N(alkyl)-heterocycle; —N(alkyl)C(=O)N(alkyl)-aryl; —N(alkyl)C(=O)N(alkyl)-heterocycle; and —Si(alkyl)$_3$. In the aforementioned exemplary substituents, in each instance, groups such as "alkyl", "aryl", "heterocycle", and "heterocyclo" can themselves be optionally substituted. For example, "alkyl" in the group "NHC(=O)O-alkyl" recited above can be optionally substituted so that both "NHC(=O)O-alkyl" and "NHC(=O)O-substituted alkyl" are exemplary substituents. Exemplary substituents also include spiro-attached or fused cyclic substituents, especially cycloalkenyl or substituted cycloalkenyl.

The term "alkylamino" refers to an amino having one hydrogen atom replaced with an alkyl. Thus, alkylamino refers to the group —NR$^a$R$^b$, wherein R$^a$ and R$^b$ are independently selected form H and alkyl, provided at least one of R$^a$ or R$^b$ is an alkyl.

The term "substituted alkylamino" refers to an alkylamino in which the one hydrogen atom is replaced with a substituted alkyl.

The term "dialkylamino" refers to an amino having both of the hydrogen atoms replaced with a group chosen from alkyl and substituted alkyl.

The terms "alkoxy" or "alkylthio" refers to an alkyl bonded through an oxygen linkage (—O—) or a sulfur linkage (—S—), respectively.

The terms "substituted alkoxy" or "substituted alkylthio" refer to a substituted alkyl bonded through an oxygen or sulfur linkage, respectively.

The term "carbonyl" refers to a C(=O).

The term "alkoxycarbonyl" refers to an alkoxy bonded through a carbonyl.

The term "alkylcarbonyl" refers to an alkyl bonded through a carbonyl.

The term "alkylcarbonyloxy" refers to an alkylcarbonyl bonded through an oxygen linkage.

The term "cycloalkenyl" refers to a cyclized alkenyl.

The term "substituted cycloalkenyl" refers to a cycloalkenyl substituted with at least one substituent, preferably 1 to 4 substituents, at any available point of attachment. Exemplary substituents include, but are not limited to, for example, the substituents described above in defining the term "substituted alkenyl" as exemplary alkenyl substituents.

The terms "heterocycle", heterocyclic" and "heterocyclo" refer to fully saturated, partially saturated, or fully unsaturated, aromatic (i.e., "heteroaryl") or nonaromatic cyclic groups that are, for example, 3 to 7 membered monocyclic, 7 to 11 membered bicyclic, or 10 to 16 membered tricyclic ring systems having at least one heteroatom in at least one carbon atom-containing ring. Each ring of the heterocycle, heterocyclic, or heterocyclo containing a heteroatom may have 1, 2, 3, or 4 heteroatoms selected from N, O, and/or S, where the N and/or S heteroatom(s) may optionally be oxidized and the N heteroatom(s) may optionally be quaternized. A heterocycle, heterocyclic, or heterocyclo may be attached to the remainder of the molecule at any heteroatom or carbon atom of the ring or ring system.

Exemplary groups containing a quaternized N include, but are not limited to, for example, a tetraalkylammonium group, such as, for example, tetramethylammonium and N-methylpyridinium; a protonated ammonium species, such as, for example, trimethylhydroammonium and N-hydropyridinium; an amine N-oxide, such as, for example, N-methylmorpholine-N-oxide and pyridine-N-oxide; and an N-aminoammonium group, such as, for example, N-aminopyridinium.

Exemplary monocyclic heterocycles, heterocyclics, or heterocyclos include, but are not limited to, for example, ethylene oxide; azetidinyl; pyrrolidinyl; pyrrolyl; pyrazolyl; oxetanyl; pyrazolinyl; imidazolyl; imidazolinyl; imidazolidinyl; oxazolyl; oxazolidinyl; isoxazolinyl; isoxazolyl; thiazolyl; thiadiazolyl; thiazolidinyl; isothiazolyl; isothiazolidinyl; furyl; tetrahydrofuryl; thienyl; oxadiazolyl; piperidinyl; piperazinyl; 2-oxopiperazinyl; 2-oxopiperidinyl; 2-oxopyrrolodinyl; 2-oxoazepinyl; azepinyl; hexahydrodiazepinyl; 4-piperidonyl; pyridyl; pyrazinyl; pyrimidinyl; pyridazinyl; triazinyl; triazolyl; tetrazolyl; tetrahydropyranyl; morpholinyl; thiamorpholinyl; thiamorpholinyl sulfoxide; thiamorpholinyl sulfone; 1,3-dioxolane; and tetrahydro-1,1-dioxothienyl.

Exemplary bicyclic heterocycles, heterocyclics, or heterocyclos include, but are not limited to, for example, indolyl; isoindolyl; benzothiazolyl; benzodioxolyl; benzoxazolyl; benzoxadiazolyl; benzothienyl; quinuclidinyl; quinolinyl; tetrahydroisoquinolinyl; isoquinolinyl; benzimidazolyl; benzopyranyl; indolizinyl; benzofuryl; benzofurazanyl; chromonyl; coumarinyl; benzopyranyl; cinnolinyl; quinoxalinyl; indazolyl; pyrrolopyridyl; furopyridinyl, such as, for example, furo[2,3-c]pyridinyl, furo[3,2-b]pyridinyl], and furo[2,3-b]pyridinyl; dihydrobenzodioxinyl; dihydrodiodobenzothiophenyl; dihydroisoindolyl; dihydroindolyl; dihydroquinolinyl; dihydroquinazolinyl, such as, for example, 3,4-dihydro-4-oxo-quinazolinyl; triazinylazepinyl; and tetrahydroquinolinyl.

Exemplary tricyclic heterocycles, heterocyclics, or heterocyclos include, but are not limited to, for example, carbazolyl; benzidolyl; phenanthrolinyl; dibenzofuranyl; acridinyl; phenanthridinyl; and xanthenyl.

The terms "substituted heterocycle," "substituted heterocyclic," and "substituted heterocyclo" refer to a heterocycle, heterocyclic, or heterocyclo substituted at any available point of attachment with at least one substituent, preferably 1 to 4 substituents. Exemplary substituents include, but are not limited to, for example, cycloalkenyl; substituted cycloalkenyl; nitro; oxo (i.e., =O); alkyl-S(O)$_m$— (m=0, 1, or 2); halo (e.g., a single halo substituent or multiple halo substituents forming, in the latter case, groups such as, for example, a perfluoroalkyl group or an alkyl group bearing CCl$_3$ or CF$_3$); alkoxy, alkylthio; hydroxyl; carboxy (i.e., —COOH); alkoxycarbonyl; alkylcarbonyloxy; CN; amino (i.e., —NH$_2$); alkylamino; dialkylamino; carbamoyl; substituted carbamoyl; carbamate; substituted carbamate; urea; substituted urea; amidinyl; substituted amidinyl; thiol (i.e., —SH); alkyl; substituted alkyl; aryl; substituted aryl; heterocycle; cycloalkyl; substituted cycloalkyl; heterocycloalkyl; —S-aryl; —S-heterocycle; —S=O-aryl; —S=O-heterocycle; arylalkyl-O—; —S(O)$_2$-aryl; —S(O)$_2$-heterocycle; —NHS(O)$_2$-aryl; —NHS(O)$_2$-heterocycle; —NHS(O)$_2$NH-heterocycle; —NHS(O)$_2$NH-aryl; —O-aryl; —O-heterocycle; —NH-aryl; —NH-heterocycle; —NHC(=O)-aryl; —NHC(=O)-alkyl; —NHC(=O)-heterocycle; —OC(=O)-aryl; —OC(=O)-heterocycle; —NHC(=O)NH-aryl; —NHC(=O)NH-heterocycle; —OC(=O)O-alkyl; —OC(=O)O-aryl; —OC(=O)O-heterocycle; —OC(=O)NH-aryl; —OC(=O)NH-heterocycle; —NHC(=O)O-aryl; —NHC(=O)O-heterocycle; —NHC(=O)O-alkyl; —C(=O)NH-aryl; —C(=O)NH-heterocycle; —C(=O)O-aryl; —C(=O)O-heterocycle; —N(alkyl)S(O)$_2$-aryl; —N(alkyl)S(O)$_2$-heterocycle; —N(alkyl)S(O)$_2$NH-aryl; —N(alkyl)S(O)$_2$NH-heterocycle; —N(alkyl)-aryl; —N(alkyl)-heterocycle; —N(alkyl)C(=O)-aryl; —N(alkyl)C(=O)-heterocycle; —N(alkyl)C(=O)NH-aryl; —N(alkyl)C(=O)NH-heterocycle; —OC(=O)N(alkyl)-aryl; —OC(=O)N(alkyl)-heterocycle; —N(alkyl)C(=O)O-aryl; —N(alkyl)C(=O)O-heterocycle; —C(=O)N(alkyl)-aryl; —C(=O)N(alkyl)-heterocycle; —NHS(O)$_2$N(alkyl)-aryl; —NHS(O)$_2$N(alkyl)-heterocycle; —NHP(O)$_2$N(alkyl)-aryl; —NHC(=O)N(alkyl)-aryl; —NHC(=O)N(alkyl)-heterocycle; —N(alkyl)S(O)$_2$N(alkyl)-aryl; —N(alkyl)S(O)$_2$N(alkyl)-heterocycle; —N(alkyl)C(=O)N(alkyl)-aryl; —N(alkyl)C(=O)N(alkyl)-heterocycle; and —Si(alkyl)$_3$. In the aforementioned exemplary substituents, in each instance, groups such as "alkyl", "aryl" and "heterocycle" can themselves be optionally substituted; for example, "alkyl" in the group "NHC(=O)O-alkyl" recited above can be optionally substituted so that both "NHC(=O)O-alkyl" and "NHC(=O)O-substituted alkyl" are exemplary substituents.

The term "heteroaryl" refers to an aromatic heterocycle, heterocyclic, or heterocyclo.

The term "substituted heteroaryl" refers to an aromatic heterocycle, heterocyclic, or heterocyclo substituted with at least one substituent, preferably 1 to 4 substituents, at any available point of attachment. Exemplary substituents include, but are not limited to, for example, the substituents describe above in defining the terms "substituted heterocycle," "substituted heterocyclic," and "substituted heterocyclo".

The term "nitro" refers to the group —N(O)$_2$.

The terms "arylalkyl", "substituted arylalkyl," "cycloalkylalkyl," "substituted cycloalkylalkyl," "cycloalkenylalkyl", "substituted cycloalkenylalkyl", "heterocycloalkyl" and "substituted heterocycloalkyl" refer to aryl, cycloalkyl, cycloalkenyl and heterocyclo groups bonded through an alkyl group, substituted on the aryl, cycloalkyl, cycloalkenyl, heterocyclo and/or alkyl where identified as a "substituted." Exemplary substituents include, but are not limited to, for example, substituted alkyl and the substituents described above in defining the term "substituted alkyl" as exemplary alkyl substituents.

The term "carbamoyl" refers to the group —C(=O)NH— which is bonded on one end to the remainder of the molecule and on the other to hydrogen or an organic moiety, such as, for example, alkyl, substituted alkyl, aryl, substituted aryl, heterocycle, alkylcarbonyl, hydroxyl, and substituted nitrogen.

The term "substituted nitrogen" refers to

The term "carbamate" refers to the group —O—C(=O)—NH— which is bonded on one end to the remainder of the molecule and on the other to hydrogen or an organic moiety, such as, for example, alkyl, substituted alkyl, aryl, substituted aryl, heterocycle, alkylcarbonyl, hydroxyl, and substituted nitrogen.

The term "urea" refers to the group —NH—C(=O)—NH— which is bonded on one end to the remainder of the molecule and on the other to hydrogen or an organic moiety, such as, for example, alkyl, substituted alkyl, aryl, substituted aryl, heterocycle, alkylcarbonyl, hydroxyl, and substituted nitrogen.

The term "amidinyl" refers to the group —C(=NH)(NH$_2$).

The terms "substituted carbamoyl", "substituted carbamate", "substituted urea", and "substituted amidinyl" refer to a carbamoyl, carbamate, urea, and amidinyl, respectively, in which one more hydrogen group is replaced by an organic moiety, such as, for example, alkyl, substituted alkyl, aryl, substituted aryl, heterocycle, alkylcarbonyl, hydroxyl, and substituted nitrogen.

The terms "halogen" and "halo" refer to fluorine, chlorine, bromine, and iodine.

The term "salt(s)", as employed herein, denotes acidic and/or basic salts formed with inorganic and/or organic acids and/or bases, and such term, as used herein, further includes zwitterion(s) ("inner salts").

The terms "zwitterion(s)", as employed herein, denote compound(s) containing both a basic moiety, including but not limited to, for example, amine, pyridine and imidazole; and an acidic moiety including but not limited to, for example, a carboxylic acid.

The term "pharmaceutically acceptable", as employed herein, indicates the subject matter being identified as "pharmaceutically acceptable" is suitable and physiologically acceptable for administration to a patient. For example, the term "pharmaceutically acceptable salt(s)" denotes suitable and physiologically acceptable salt(s).

When a functional group is termed "protected", the functional group is in a modified form to mitigate, especially to preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991).

The compounds of Formula (I) can also form salts. As a result, when a compound of Formula (I) is referred to herein, such reference includes, unless otherwise indicated, salts thereof. In one embodiment, the compounds of Formula (I) form pharmaceutically acceptable salts. In another embodiment, the compounds of Formula (I) form salts that can, for example, be used to isolate and/or purify the compounds of Formula (I). Salt(s) of the Formula (I) compounds can be formed by, for example, reacting a Formula (I) compound with, for example, an equivalent amount of acid or base in a medium that allows the thusly formed salt to, for example, either be precipitated out, or be isolated via lyophilization Exemplary acidic salt(s) that the compounds of Formula (I) can form with inorganic and/or organic acids include, but are not limited to, for example, acetates, such as are formed with acetic or trihaloacetic acid; adipates; alginates; ascorbates; aspartates; benzoates; benzenesulfonates; bisulfates; borates; butyrates; citrates; camphorates; camphorsulfonates; cyclopentanepropionates; digluconates; dodecylsulfates; ethanesulfonates; fumarates; glucoheptanoates; glycerophosphates; hemisulfates; heptanoates; hexanoates; hydrochlorides; hydrobromides; hydroiodides; hydroxyethanesulfonates, such as, for example, 2-hydroxyethanesulfonates; lactates; maleates; methanesulfonates; naphthalenesulfonates, such as, for example, 2-naphthalenesulfonates; nicotinates; nitrates; oxalates; pectinates; persulfates; phenylpropionates, such as, for example, 3-phenylpropionates; phosphates; picrates; pivalates; propionates; salicylates; succinates; sulfates, such as, for example, are formed with sulfuric acid; sulfonates; tartrates; thiocyanates; and toluenesulfonates, such as, for example, tosylates and undecanoates. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), and aralkyl halides (e.g. benzyl and phenethyl bromides) to quaternize basic nitrogen-containing groups. Such salts can be formed in accordance with methods known to a person of ordinary skill in the art.

Prodrugs and solvates of the compounds of Formula (I) are also contemplated herein. The term "prodrug(s)", as employed herein, denotes a compound that, upon administration to a subject, undergoes chemical conversion via metabolic and/or chemical processes in vivo to yield a compound and/or derivative of Formula (I), or a salt and/or solvate thereof. Various forms of prodrug(s) are well known in the art. For examples of such prodrug derivatives, see:

a) *Design of Prodrugs*, edited by H. Bundgaard (Elsevier, 1985) and *Methods in Enzymology*, Vol. 112, pp. 309-396, edited by K. Widder et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, pp. 1-38 (1992).

The term "solvate", as employed herein, denotes a compound produced by the chemical interaction of at least one solvent with at least one solute comprising at least one compound of Formula (I). Exemplary solvates include, but are not limited to, for example, hydrates.

All stereoisomers and geometric isomer(s) of the compounds of Formula (I), such as, for example, stereoisomer(s) that exist due to asymmetric carbons on various substituents, either in admixture or in pure or substantially pure form are further contemplated herein. In one embodiment, all enantiomers, tautomers, and diastereomers of the compounds of Formula (I), as well as mixtures, compounds, racemic compounds, racemic mixtures, and racemates produced therefrom are contemplated herein. In another embodiment, all optically active isomers of the compounds of Formula (I), including pure or substantially pure optically active isomers, i.e., optically active isomers substantially free of other isomers are contemplated herein.

When a compound containing a single enantiomer of a compound of Formula (I) is desired, such compound can be obtained by either resolution of the final product or by stereospecific synthesis from either isomerically pure starting material(s), or any convenient intermediate(s). Resolution of the final product, an intermediate, or a starting material can be effected by any suitable method known in the art, including, for example, physical methods, such as, for example, fractional crystallization, separation or crystallization of diastereomeric derivatives, and separation by chiral column chromatography. Individual optical isomers can be obtained from racemates through, for example, conventional methods, such as, for example, salt formation with an optically active acid followed by crystallization. The chiral centers of the compounds in accordance with Formula (I) can have the S or R configuration as defined by the IUPAC 1974 Recommendations.

Disclosed herein are compounds of Formula (I):

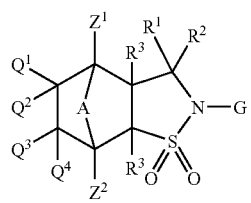

(I)

wherein A, G, $Z^1$, $Z^2$, $Q^1$, $Q^2$, $Q^3$, $Q^4$, $R^1$, $R^2$, $R^3$, $R^5$, $R^6$, $R^7$, $R^8$, and $R^9$ are as defined hereinabove; or a pharmaceutically-acceptable salt thereof.

The structures of the compounds of Formula (I) comprise core rings represented by Formula (II):

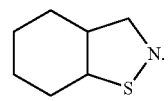

(II)

The structures of the compounds of Formula (I) further comprise an optionally substituted alkylene bridge represented by group A, wherein A is $CR^4R^5$, $C(=O)$, $C(OR^4)R^5$, $CR^4R^5CR^4R^5$, $CR^4R^5C(=O)$, or $CR^4R^5C(OR^4)R^5$; and $R^4$ and $R^5$ are as defined hereinabove.

Examples of Formula (I) compounds in which A is $CR^4R^5C(=O)$ include compounds of Formula (Ia):

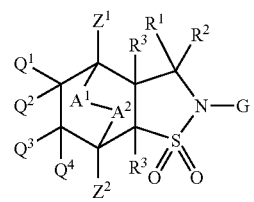

(Ia)

wherein one of $A^1$ and $A^2$ is $CR^4R^5$ and the other of $A^1$ and $A^2$ is $C(=O)$; and G, $Z^1$, $Z^2$, $Q^1$, $Q^2$, $Q^3$, $Q^4$, $R^1$, $R^2$, $R^3$, $R^4$, $R^5$, $R^6$, $R^7$, $R^8$, and $R^9$ are as defined hereinabove.

Examples of Formula (I) compounds in which A is $CR^4R^5C(OR^4)R^5$ include compounds of Formula (Ia) wherein one of $A^1$ and $A^2$ is $CR^4R^5$ and the other of $A^1$ and $A^2$ is $C(OR^4)R^5$; and G, $Z^1$, $Z^2$, $Q^1$, $Q^2$, $Q^3$, $Q^4$, $R^1$, $R^2$, $R^3$, $R^4$, $R^5$, $R^6$, $R^7$, $R^8$, and $R^9$ are as defined hereinabove.

In one embodiment, compounds of Formula (I) are provided wherein A is $CR^4R^5$ or $CR^4R^5CR^4R^5$ and $R^4$ and $R^5$ are each independently H, lower alkyl, and/or substituted lower alkyl.

In another embodiment, compounds of Formula (I) are provided wherein A is $CR^4R^5$ or $CR^4R^5CR^4R^5$ and $R^4$ and $R^5$ are each independently H, methyl, substituted methyl, ethyl, and/or substituted ethyl.

In an even further embodiment, compounds of Formula (I) are provided wherein A is $CH_2$.

According to another embodiment, there are provided compounds of Formula (I) wherein $Z^1$ and $Z^2$ are each independently H, alkyl, substituted alkyl, alkenyl, substituted alkenyl, and/or $-C(=O)OR^6$; and $R^6$ is as defined hereinabove.

In yet another embodiment, compounds of Formula (I) are provided wherein $Z^1$ and $Z^2$ are each independently H, lower alkyl, and/or substituted lower alkyl; and in a further embodiment, $Z^1$ and $Z^2$ are each independently H, methyl, and/or substituted methyl.

In yet a further embodiment, compounds of Formula (I) are provided wherein $Z^1$ is H and $Z^2$ is H, alkyl, substituted alkyl, alkenyl, substituted alkenyl, or $-C(=O)OR^6$; and $R^6$ is as defined hereinabove.

In yet an even further embodiment, compounds of Formula (I) are provided wherein $Z^1$ is H and $Z^2$ is H; a lower alkyl, such as, for example, methyl; or a substituted lower alkyl, such as, for example, substituted methyl.

According to another embodiment, compounds of Formula (I) are provided wherein $R^1$ and $R^2$ are each independently H, alkyl, substituted alkyl, and/or CN; and in yet another embodiment, $R^1$ and $R^2$ are each independently H, lower alkyl, and/or substituted lower alkyl.

In an even further embodiment, compounds of Formula (I) are provided wherein $R^1$ and $R^2$ are each independently H, methyl, substituted methyl, ethyl, and/or substituted ethyl.

In yet a further a further embodiment, compounds of Formula (I) are provided wherein one of $R^1$ and $R^2$ is H; and the other of $R^1$ and $R^2$ is H alkyl, substituted alkyl, or CN.

In yet an even further embodiment, compounds of Formula (I) are provided wherein one of $R^1$ and $R^2$ is H; and the other of $R^1$ and $R^2$ is H, lower alkyl, and/or substituted lower alkyl.

In still yet a further embodiment, compounds of Formula (I) are provided wherein one of $R^1$ and $R^2$ is H; and the other of $R^1$ and $R^2$ is H, methyl, substituted methyl, ethyl, and/or substituted ethyl.

In still yet an even further embodiment, compounds of Formula (I) are provided wherein one of $R^1$ and $R^2$ is H; and the other of $R^1$ and $R^2$ is H or lower alkyl.

According to still yet another embodiment, compounds of Formula (I) are provided wherein each $R^3$ is independently H, alkyl, substituted alkyl, alkenyl, substituted alkenyl, —C(=O)O$R^6$, and/or —C(=O)N$R^6R^7$; and $R^6$ and $R^7$ are as defined hereinabove.

In a further embodiment, compounds of Formula (I) are provided wherein each $R^3$ is independently H, lower alkyl, and/or substituted lower alkyl.

In yet a further embodiment, there are provided compounds of Formula (I) wherein each $R^3$ is independently H, methyl, and/or substituted methyl.

In yet an even further embodiment, compounds of Formula (I) are provided wherein one $R^3$ is H and the other $R^3$ is H; a lower alkyl, such as, for example, methyl; a substituted lower alkyl, such as, for example, substituted methyl; or —C(=O)N$R^6R^7$, wherein $R^6$ and $R^7$ are as defined hereinabove.

According to another embodiment, there are provided compounds of Formula (Ib):

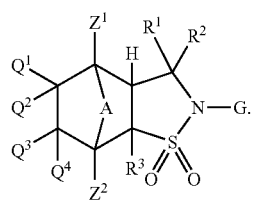

(Ib)

wherein A, G, $Z^1$, $Z^2$, $Q^1$, $Q^2$, $Q^3$, $Q^4$, $R^1$, $R^2$, $R^3$, $R^4$, $R^5$, $R^6$, $R^7$, $R^8$, and $R^9$ are as defined hereinabove.

In one embodiment, compounds of Formula (Ib) are provided wherein $R^3$ is H, alkyl, substituted alkyl, alkenyl, substituted alkenyl, —C(=O)O$R^6$, or —C(=O)N$R^6R^7$; and $R^6$ and $R^7$ are as defined hereinabove.

In a further embodiment, compounds of Formula (Ib) are provided wherein $R^3$ is H, lower alkyl, substituted lower alkyl, or —C(=O)N$R^6R^7$; and $R^6$ and $R^7$ are as defined hereinabove.

In still as further embodiments, compounds of Formula (Ib) are provided wherein $R^3$ is H, methyl, substituted methyl, or —C(=O)N$R^6R^7$; and $R^6$ and $R^7$ are as defined hereinabove.

According to yet another embodiment, compounds of Formula (I) are provided wherein each $R^4$ and each $R^5$ are independently H, alkyl, and/or substituted alkyl.

In a further embodiment, compounds of Formula (I) are provided wherein each $R^4$ and each $R^5$ are independently H, lower alkyl, and/or substituted lower alkyl.

In yet a further embodiment, compounds of Formula (I) are provided wherein each $R^4$ and each $R^5$ are independently H, methyl, substituted methyl, ethyl, and/or substituted ethyl.

In a still further embodiment, compounds of Formula (I) are provided wherein each $R^4$ is H and each $R^5$ is H.

According to another embodiment, compounds of Formula (I) are provided wherein each $R^6$ and each $R^7$ are independently H, alkyl, substituted alkyl, arylalkyl, substituted arylalkyl, aryl, substituted aryl, heteroaryl, substituted heteroaryl, and/or CN.

In a further embodiment, compounds of Formula (I) are provided wherein each $R^6$ and each $R^7$ are independently H, alkyl, and/or substituted alkyl.

In yet a further embodiment, compounds of Formula (I) are provided wherein each $R^6$ and each $R^7$ are independently H, lower alkyl, and/or substituted lower alkyl.

In an even further embodiment, compounds of Formula (I) are provided wherein each $R^6$ and each $R^7$ are independently H, methyl, substituted methyl, ethyl, and/or substituted ethyl.

According to another embodiment, there are provided compounds of Formula (I) wherein $R^8$ is H, lower alkyl, substituted lower alkyl, —C(=O)O$R^6$, or —SO$_2R^7$; and $R^6$ and $R^7$ are as defined hereinabove.

In a further embodiment, compounds of Formula (I) are provided wherein $R^8$ is H, lower alkyl, or substituted lower alkyl.

In an even further embodiment, compounds of Formula (I) are provided wherein $R^8$ is H, methyl, or substituted methyl.

According to another embodiment, compounds of Formula (I) are provided wherein each $R^9$ is independently alkyl or substituted alkyl.

In a further embodiment, compounds of Formula (I) are provided wherein each $R^9$ is lower alkyl or substituted lower alkyl.

In an even further embodiment, compounds of Formula (I) are provided wherein each $R^9$ is methyl, substituted methyl, ethyl, or substituted ethyl.

According to another embodiment, compounds of Formula (I) are provided wherein $Q^1$, $Q^2$, $Q^3$, and $Q^4$ are each independently H, halogen, CN, alkyl, substituted alkyl, aryl, substituted aryl, heterocyclo, substituted heterocyclo, —O$R^6$, —N$R^6R^7$, —$NR^6$C(=O)O$R^7$, —OC(=O)N$R^6R^7$, —$NR^6$SO$_2R^7$, —$NR^6$SO$_2NR^6R^7$, —SO$_2R^7$—SO$_2NR^6R^7$, —S$R^9$, —SO$R^9$, —C(=O)N$R^6R^7$, —C(=O)O$R^6$, —C(=O)$R^6$, —$NR^6$C(=O)$R^7$, and/or —$NR^6$C(=O)N$R^6R^7$; or $Q^1$ and $Q^2$ together form 0 and/or $Q^3$ and $Q^4$ together form 0; or $Q^2$ and $Q^4$ together form C$R^6R^7$, O, or N$R^8$; and $R^6$, $R^7$, $R^8$, and $R^9$ are as defined hereinabove.

In a further embodiment, compounds of Formula (I) are provided wherein $Q^1$, $Q^2$, $Q^3$, and $Q^4$ are each independently H, halogen, CN, alkyl, substituted alkyl, —O$R^6$, —N$R^6R^7$, —$NR^6$C(=O)O$R^7$, —OC(=O)N$R^6R^7$, —$NR^6$SO$_2R^7$, —SO$_2R^7$, —SO$_2NR^6R^7$, —C(=O)N$R^6R^7$, —C(=O)O$R^6$, —C(=O)$R^6$, —$NR^6$C(=O)$R^7$, and/or —$NR^6$C(=O)N$R^6R^7$; or $Q^1$ and $Q^2$ together form 0 and/or $Q^3$ and $Q^4$ together form 0; or $Q^2$ and $Q^4$ together form C$R^6R^7$, O, or N$R^8$; and $R^6$, $R^7$, and $R^8$ are as defined hereinabove.

In an even further embodiment, compounds of Formula (I) are provided wherein $Q^1$, $Q^2$, $Q^3$, and $Q^4$ are each independently H, halogen, lower alkyl, substituted lower alkyl, —$NR^6$C(=O)O$R^7$, —$NR^6$SO$_2R^7$, —C(=O)N$R^6R^7$, and/or —$NR^6$C(=O)$R^7$; and $R^6$ and $R^7$ are as defined hereinabove.

In a still further embodiment, compounds of Formula (I) are provided wherein $Q^1$, $Q^2$, $Q^3$, and $Q^4$ are each independently H, halogen, CN, $C_1$-$C_4$alkyl, substituted $C_1$-$C_4$alkyl, —$NR^6C(=O)OR^7$, —$NR^6SO_2R^7$, —$C(=O)NR^6R^7$, and/or —$NR^6C(=O)R^7$; and $R^6$ and $R^7$ are as defined hereinabove.

In yet an even further embodiment, compounds of Formula (I) are provided wherein $Q^2$ and $Q^4$ together form $CR^6R^7$, O, or $NR^8$; and $R^6$, $R^7$, and $R^8$ are as defined hereinabove.

According to another embodiment, there are provided compounds of Formula (Ic):

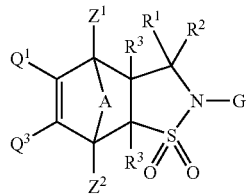

(Ic)

wherein A, G, $Z^1$, $Z^2$, $Q^1$, $Q^3$, $R^1$, $R^2$, $R^3$, $R^4$, $R^5$, $R^6$, $R^7$, $R^8$, and $R^9$ are as defined hereinabove.

In one embodiment, compounds of Formula (Ic) are provided wherein $Q^1$ and $Q^3$ are each independently H, halogen, CN, alkyl, substituted alkyl, aryl, substituted aryl, heterocyclo, substituted heterocyclo, —$OR^6$, —$NR^6R^7$, —$NR^6C(=O)OR^7$, —$OC(=O)NR^6R^7$, —$NR^6SO_2R^7$, —$NR^6SO_2NR^6R^7$, —$SO_2R^7$, —$SO_2NR^6R^7$, —$SR^9$—$SOR^9$—$C(=O)NR^6R^7$, —$C(=O)OR^6$, —$C(=O)R^6$, —$NR^6C(=O)R^7$, and/or —$NR^6C(=O)NR^6R^7$; and $R^6$, $R^7$, and $R^9$ are as defined hereinabove.

In a further embodiment, compounds of Formula (Ic) are provided wherein $Q^1$ and $Q^3$ are each independently H, halogen, CN, alkyl, substituted alkyl, —$OR^6$, —$NR^6R^7$, —$NR^6C(=O)OR^7$, —$OC(=O)NR^6R^7$, —$NR^6SO_2R^7$, —$SO_2R^7$, —$SO_2NR^6R^7$, —$C(=O)NR^6R^7$, —$C(=O)OR^6$, —$C(=O)R^6$, —$NR^6C(=O)R^7$, and/or —$NR^6C(=O)NR^6R^7$; and $R^6$ and $R^7$ are as defined hereinabove.

In an even further embodiment, compounds of Formula (Ic) are provided wherein $Q^1$ and $Q^3$ are each independently H, halogen, CN, lower alkyl, substituted lower alkyl, —$NR^6C(=O)OR^7$, —$NR^6SO_2R^7$, —$C(=O)NR^6R^7$, and/or —$NR^6C(=O)R^7$; and $R^6$ and $R^7$ are as defined hereinabove.

In yet an even further embodiment, compounds of Formula (Ic) are provided wherein $Q^1$ and $Q^3$ are each independently H, halogen, CN, $C_1$-$C_4$alkyl, substituted $C_1$-$C_4$alkyl, —$NR^6C(=O)OR^7$, —$NR^6SO_2R^7$, —$C(=O)NR^6R^7$, and/or —$NR^6C(=O)R^7$; and $R^6$ and $R^7$ are as defined hereinabove.

According to another embodiment, compounds of Formula (I) are provided wherein G is substituted aryl or substituted heteroaryl, and is attached to the N atom of the core rings via a carbon atom of G.

In a further embodiment, compounds of Formula (I) are provided wherein

G is substituted phenyl, substituted naphthyl, substituted pyridyl, substituted quinoline, substituted isoquinoline, or substituted benzoxadiazol.

G may be substituted with 1, 2, or 3 substituents.

In one embodiment, the 1, 2, or 3 substituents are each independently —CN, Cl, Br, I, $CF_3$, methyl, and/or —$OR^{11}$, wherein $R^{11}$ is lower alkyl or substituted lower alkyl.

Examples of suitable G groups include, but are not limited to:

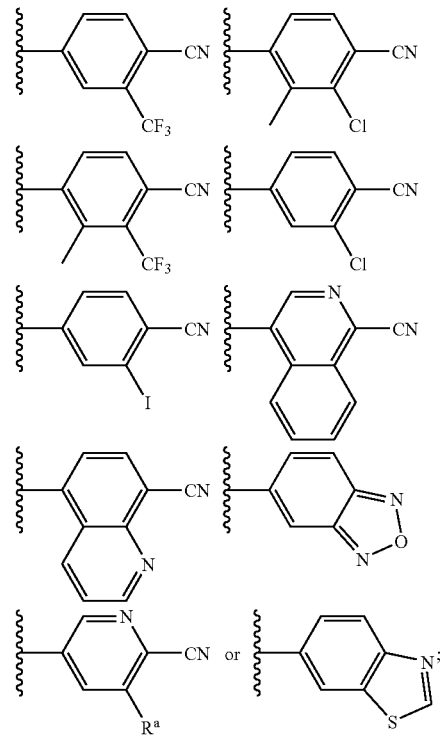

wherein $R^a$ is alkyl, substituted alkyl, or —$OR^{11}$; and $R^{11}$ is alkyl or substituted alkyl.

According to another embodiment, compounds of Formula (I) are provided wherein G is a phenyl substituted at the 4-position, and optionally substituted at the 2- and/or 3-positions.

In one embodiment, compounds of Formula (I) are provided wherein G is a phenyl substituted with at least one of CN, Cl, Br, I, $CF_3$, methyl, and/or —$OR^{11}$; and $R^{11}$ is lower alkyl or substituted lower alkyl.

In a further embodiment, compounds of Formula (I) are provided wherein G is a 4-cyano phenyl optionally substituted at the 2- and/or 3-positions. Examples of suitable 4-cyano phenyl groups include:

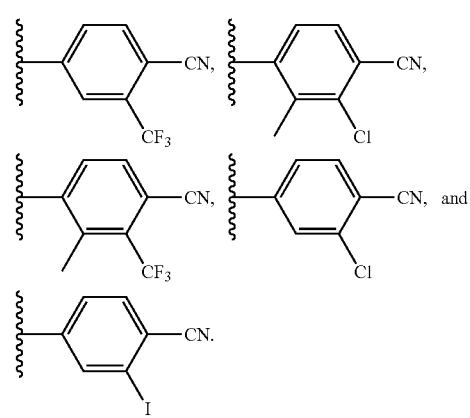

One embodiment provides a compound of Formula (I) or a pharmaceutically-acceptable salt thereof, wherein the symbols have the following meanings and are, for each occurrence, independently selected:

G is aryl or substituted aryl, wherein G is attached to the N atom of the core rings via a carbon atom of G;

A is $CR^4R^5$, $CR^4R^5CR^4R^5$, $C(OR^4)R^5$, or $CR^4R^5C(OR^4)R^5$;

$Z^1$ and $Z^2$ are each independently H, alkyl, and/or substituted alkyl;

$Q^1$, $Q^2$, $Q^3$, and $Q^4$ are each independently H, halogen, CN, alkyl, substituted alkyl, aryl, substituted aryl, —$OR^6$, —$NR^6R^7$, —$NR^6C(=O)OR^7$, $NR^6C(=O)R^7$, —$NR^6C(=O)NR^6R^7$, —$OSO_2R^7$, and/or —$NR^6SO_2R^7$; or $Q^1$ and $Q^2$ together form 0 and/or $Q^3$ and $Q^4$ together form 0; or $Q^2$ and $Q^4$ together form $CR^6R^7$, O, or a carbon-carbon bond;

$R^1$ and $R^2$ are each independently H, alkyl, substituted alkyl, alkenyl, and/or substituted alkenyl;

each $R^3$ is independently H, alkyl, substituted alkyl, alkenyl, substituted alkenyl, —$C(=O)NR^6R^7$, and/or —$C(=O)OR^6$;

$R^4$ and $R^5$ are each independently H, alkyl, substituted alkyl, and/or CN; or $R^4$ and $R^5$ together with the carbon atom to which they are attached form a cycloalkyl ring; and $R^6$ and $R^7$ are each independently H, alkyl, substituted alkyl, arylalkyl, substituted arylalkyl, aryl, substituted aryl, and/or CN;

with the proviso that when $Q^2$ and $Q^4$ together form a carbon-carbon bond and $A^1$ is $CH_2$, then G is not a phenyl group substituted at the 4-position with an oxygen-substituted methylene group or —C(=O)O-alkyl.

As used herein, the endo isomer of the compound of Formula I has the structure shown in Formula (I-endo):

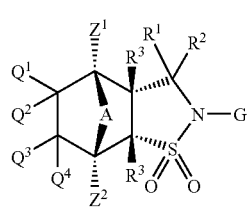

(I-endo)

and is characterized by the bridge formed by A being anti to the core rings.

As used herein, the exo isomer of the compound of Formula (I) has the structure shown in Formula (I-exo):

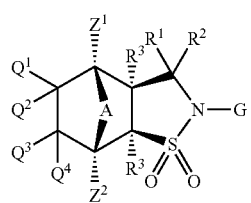

(I-exo)

and is characterized by the bridge formed by A being syn to the core rings.

Compounds in accordance with Formula (I) may be an endo isomer, an exo isomer, or a mixture of the endo and exo isomers, including but not limited to, for example, an equimolar mixture of endo and exo isomers.

In general, the compounds of Formula (I) can be prepared in accordance with the following Schemes and the general knowledge of one skilled in the art and/or using methods set forth in the Examples that follow. Solvents, temperatures, pressures, and other reaction conditions can readily be selected by one of ordinary skill in the art. Starting materials are commercially available or readily prepared by one skilled in the art. Combinatorial techniques can be employed in the preparation of compounds, for example, where the intermediates possess groups suitable for these techniques. In the schemes, the groups A, G, $Z^1$, $Z^2$, $Q^1$, $Q^2$, $Q^3$, $Q^4$, $R^1$, $R^2$, and $R^3$ described hereinabove.

Scheme 1

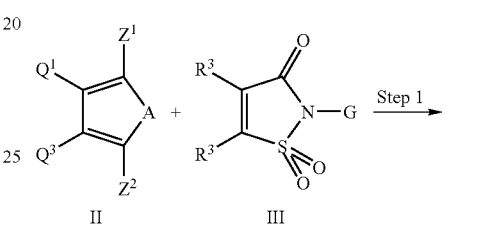

II    III

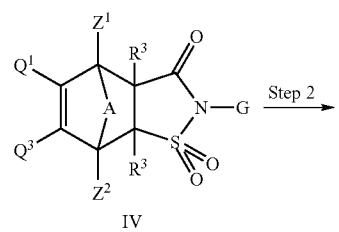

IV

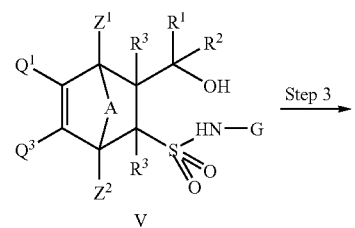

V

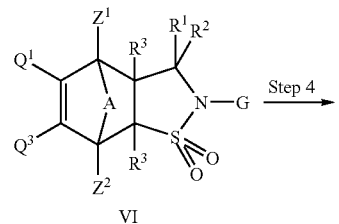

VI

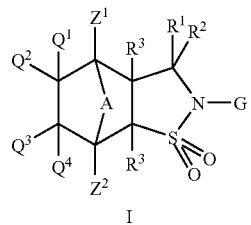

I

Step 1

A diene of the general Formula II and a dienophile of the general Formula III can undergo a [4+2] cycloaddition under thermal or Lewis acidic conditions in a solvent, such as, for example, THF and/or toluene to generate compounds of the general Formula IV.

A diene of general Formula II can be obtained either from commercial sources, or can be readily made by one of skill in the art, for example, in accordance with the following publication and references found therein: Derrick L. J. Clive et al., *Tetrahedron*, 60, 4205-4221 (2004). Representative methods of preparation of dienophiles of general Formula III are discussed below in Schemes 3 and 4.

Step 2

Compounds of general Formula IV can be treated under reductive conditions, such as, for example, sodium borohydride in a solvent system of THF/MeOH to yield an alcohol of general Formula V.

Step 3

Compounds of general Formula V can undergo cyclization under a variety of conditions including, but not limited to, for example, an intramolecular Mitsunobu reaction by treating the Formula V compound with, for example, triphenylphosphine and diisopropylazodicarboxylate in THF to yield a compound of general Formula VI. A Formula V compound may also be treated with an activating agent, such as, for example, para-toluenesulfonyl chloride, followed by a strong base, such as, for example, lithium diisopropylamide to afford a cyclized compound in accordance with Formula VI.

When $R^3$=H, a compound of Formula VI can be treated with a strong base, such as, for example, lithium diisopropylamide to generate an anion that can react with various electrophiles, such as, for example, methyl iodide and methyl chloroformate, to produce a compound of the general Formula VI where $R^3$ is the corresponding alkyl or acyl group.

Step 4

A compound of the general Formula I can be produced by functionalizing the olefin of the Formula VI compound via a variety of methods known to one skilled in the art. Such functionalization methods include, but are not limited to, for example, dihydroxylation; aminohydroxylation; hydrogenation; hydroxylation; hydroboration and subsequent oxidation; epoxidation; aziridination; cyclopropanation; bromination; and chlorination. The resulting products may undergo further functional group manipulations, including, but not limited to, for example, converting a hydroxyl group to a fluoro functionality by treating with DAST; and reducing an azide to the corresponding amine and further derivatizing to alkyl carbamates, amides, sulfonamides or ureas. Other well-known methods for functionalizing an olefin can be found in standard synthetic organic references, such as, for example, Larock, R. C., *Comprehensive Organic Transformations*, VCH Publishers, New York (1989) and March, J., *Advanced Organic Chemistry*, John Wiley & Sons Inc. USA (1985).

If an $R^3$ of a compound in accordance with Formula VI or I is an ester, the compound can be hydrolyzed to the corresponding carboxylic acid by being reacted with a reagent, such as, for example, lithium hydroxide in a solvent, such as, for example, THF. The acid may subsequently be converted to a variety of alkyl amides under standard conditions, e.g. treating with oxalyl chloride followed by reaction with the corresponding amine. The carboxylic acid may also be reduced to the corresponding alcohol or subjected to Curtius rearrangement conditions to provide a primary amine for further functional group manipulations.

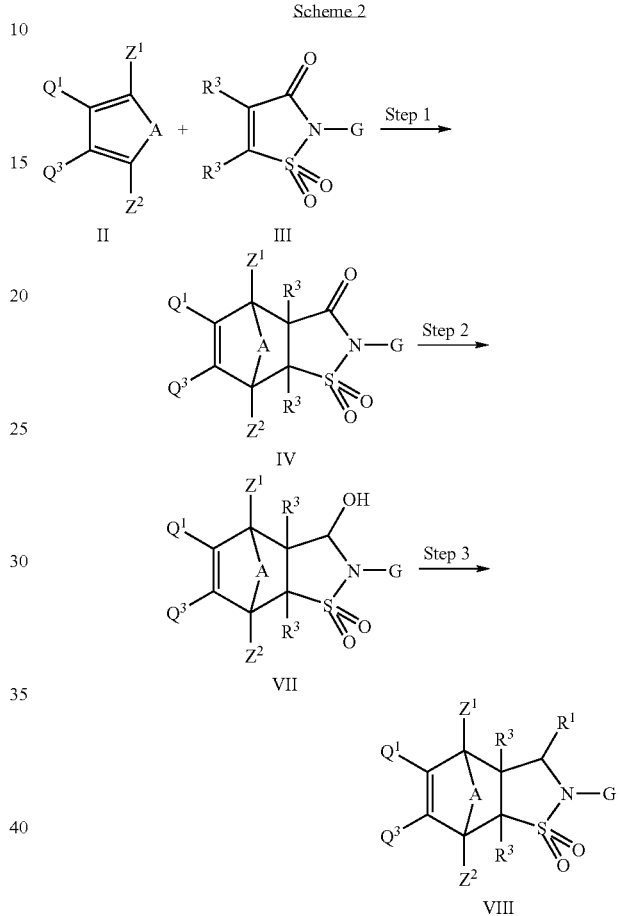

Scheme 2

Step 1

Compounds of general Formula IV can be prepared in accordance with the procedure outlined in Step 1 of Scheme 1.

Step 2

Compounds of general Formula VII can be produced by treating a compound of general Formula IV with an appropriate reducing agent, such as, for example, diisobutylaluminum hydride in a solvent, such as, for example, toluene.

Step 3

Compounds of general Formula VII can be treated with an appropriate reagent, such as, for example, trimethylaluminum and allyltrimethylsilane followed by reaction with a reagent, such as, for example, boron trifluoride etherate to produce the corresponding alkylated compound of Formula VIII. The olefin of a Formula VIII compound can be further functionalized in accordance with the procedures described in step 4 of Scheme 1.

Step 1

Appropriately substituted dithiopropionic acid IX may be commercially available; or in the alternative can be prepared in accordance with synthetic routes described in the literature, e.g., Lewis S. N. et al., *J. Heterocyclic Chem.* 8, 571-580 (1971). The diacid IX can be converted to the corresponding bis-amide X via a 2-step sequence involving a) first reacting the diacid 1× with a reagent, such as, for example, thionyl chloride in the presence of a suitable catalyst, such as, for example, pyridine to produce the corresponding bis-acid chloride, and b) subsequently treating the thusly produced bis-acid chloride with an appropriate amine in a solvent, such as, for example, THF to provide bis-amide X.

Step 2

Bis-amide X can be cyclized to a compound of Formula XI by reacting bis-amide X with a reagent, such as, for example, sulfuryl chloride in a solvent, such as, for example, toluene.

Step 3

A dienophile in accordance with Formula III can be produced by the oxidization of a compound of Formula XI. Such oxidation can be effectuated by, for example, reacting a Formula XI compound with a reagent, such as, for example, meta-chloroperoxybenzoic acid in a solvent, such as, for example, dichloromethane.

Scheme 4 illustrates a method for synthesizing a Formula XVII dienophile, which is a Formula III dienophile in which one $R^3$ is a H, e.g. see Beeley, N. R. A. et al., *J. Chem. Soc. Perkin Trans. I*, 2245-2251 (1994).

Step 1

A propenoic acid in accordance with Formula XIII can be produced by heating a propynoic acid in accordance with Formula XII with a benzylthiol in the presence of a base, such as, for example, sodium carbonate and a solvent, such as, for example, ethanol.

Step 2

The Formula XIII propenoic acid can be converted to the corresponding amide of Formula XIV via successive reactions with an acid chloride, such as, for example, oxalyl chloride and an appropriate amine.

Step 3

The corresponding sulfoxide of Formula XV can be produced by reacting the Formula XIV compound with an oxidizing agent, such as, for example, 1 equivalent of m-CPBA.

Step 4

The Formula XV compound can be cyclized to the isothiazolone of Formula XVI by reacting the Formula XV compound with a reagent, such as, for example, trichloroacetic anhydride in a solvent, such as, for example, dichloromethane.

Step 5

The isothiazolone of Formula XVI can be oxidized to the dienophile XVII in accordance with the procedure described in step 3 of Scheme 3.

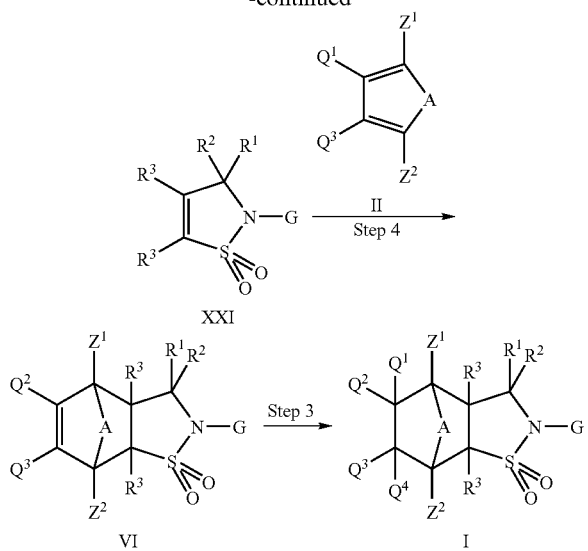

Alternatively, compounds in accordance with Formula I can be synthesized in accordance with Scheme 5. The dienophile of Formula XXI can be prepared in accordance with a procedure reported in the literature (Harned, A. M. et al., Org. Lett., 2003, 5, 15-18).

Step 1

A sulfonamide in accordance with Formula XIX can be produced by treating a styrene sulfonyl chloride in accordance with Formula XVIII with an appropriate amine in a solvent, such as, for example, pyridine.

Step 2

A compound in accordance with Formula XX can be obtained by alkylating the Formula XIX sulfonamide with a suitable electrophile, such as, for example, allyl bromide in the presence of reagents, such as, for example, potassium carbonate and potassium iodide in a solvent, such as, for example, acetonitrile.

Step 3

The Formula XX compound can be subjected to olefin metathesis by being heated in the presence of an appropriate catalyst, such as, for example, $(PCy_3)_2Cl_2Ru=CHPh$ to provide a cyclized compound in accordance with Formula XXI.

Step 4

The dienophile of Formula XXI can undergo a [4+2]cycloaddition with an appropriately substituted diene II in the presence of a catalyst, such as, for example, diethylaluminum chloride in a solvent, such as, for example, toluene to afford a compound in accordance with Formula V.

Step 5

The Formula V compound can be converted to a compound in accordance with Formula VI as described in step 4 of Scheme 1.

Compounds of Formula (I) are useful for modulating the function of nuclear hormone receptors (NHRs). Formula (I) compounds can, for example, act as an agonist, partial agonist, antagonist, or partial antagonist of the androgen receptor (AR), the estrogen receptor (ER), the progesterone receptor (PR), the glucocorticoid receptor (GR), the mineralocorticoid receptor (MR), the steroid and xenobiotic receptor (SXR), other steroid binding NHRs, the Orphan receptors, or other NHRs.

In one embodiment, at least one compound of Formula (J) selectively modulates a single NHR within the NHR family.

The terms "modulate", "modulates", "modulating", or "modulation", as used herein, refer to, for example, the activation (e.g., agonist activity) or inhibition (e.g., antagonist activity) of at least one NHR.

Formula (I) compounds are useful to treat NHR-associated conditions.

The term "NHR-associated condition(s)", as used herein, denotes a condition or disorder that can be treated by modulating the function of at least one NHR associated with the condition or disorder. The treatment comprises preventing, partially alleviating, or curing the condition or disorder. Modulation may occur either locally, for example, within certain tissues of the subject being treated, or more extensively throughout the subject.

Compounds in accordance with Formula (I) can be used to treat a variety of medical conditions and/or disorders associated with the ER pathway. The compounds of Formula (I) can modulate the function of the ER by, for example, agonizing, partially agonizing, antagonizing, and/or partially antagonizing the ER. In one embodiment, at least one Formula (I) compound selectively modulates the function of at least one ER.

Medical conditions associated with the ER pathway include, but are not limited to, for example, osteoporosis; hot flashes; vaginal dryness; prostate cancer; breast cancer; endometrial cancer; other ER expressing cancers; contraception; pregnancy termination; menopause; amenorrhea; and dysmenorrhea.

Compounds in accordance with Formula (I) can be used to treat a variety of medical conditions and/or disorders associated with the PR pathway. Formula (I) compounds can modulate the function of the PR by, for example, agonizing, partially agonizing, antagonizing, and/or partially antagonizing the PR. In one embodiment, at least one Formula (I) compound selectively modulates the function of at least one PR.

Medical conditions associated with the PR pathway include, but are not limited to, for example, breast cancer; other PR containing cancers; endometriosis; cachexia; contraception; menopause; cyclesynchrony; meniginoma; dysmenorrhea; fibroids; pregnancy termination; labor induction; and osteoporosis.

Compounds in accordance with Formula (I) may be used to treat a variety of medical conditions and/or disorders associated with the GR pathway. Formula (I) compounds can modulate the function of the GR by, for example, agonizing, partially agonizing, antagonizing, and/or partially antagonizing the GR. In one embodiment, at least one Formula (I) compound selectively modulates the function of at least one GR.

Medical conditions associated with the GR pathway include, but are not limited to, for example, inflammatory diseases; autoimmune diseases; prostate cancer; breast cancer; Alzheimer's disease; psychotic disorders; drug dependence; non-insulin dependent Diabetes Mellitus; and as dopamine receptor blocking agents or otherwise as agents for the treatment of dopamine receptor mediated disorders. Glucocorticoid receptor AP-1 ("GR AP-1") inhibitors can be used as anti-inflammatory and immunosuppressive agents to, for example, treat a wide variety of inflammatory and autoimmune diseases, including, but not limited to, for example, rheumatoid arthritis; osteoarthritis; inflammatory bowel disease; asthma; chronic obstructive pulmonary disease; prevention of transplant rejection; multiple sclerosis; and psoriasis. In one embodiment, at least one Formula (I) compound may inhibit the GR AP-1 and may further be used in combination with at least one known GR AP-1 inhibitor, such as, for example, prednisone, which is used to treat at least one of the above diseases.

Compounds in accordance with Formula (I) may be used to treat a variety of medical conditions and/or disorders associated with the MR pathway. Formula (I) compounds can modulate the function of the MR by, for example, agonizing, partially agonizing, antagonizing, and/or partially antagonizing the MR. In one embodiment, at least one Formula (I) compound selectively modulates the function of at least one MR.

Medical conditions associated with the MR pathway include, but are not limited to, for example, drug withdrawal syndrome and inflammatory diseases.

Compounds in accordance with Formula (I) may be used to treat a variety of medical conditions and/or disorders associated with the Aldosterone Receptor (ALDR) pathway. Formula (I) compounds can modulate the function of the ALDR by, for example, agonizing, partially agonizing, antagonizing, and/or partially antagonizing the ALDR. In one embodiment, at least one Formula (I) compound selectively modulates the function of at least one ALDR.

Medical conditions associated with the ALDR pathway include, but are not limited to, for example, congestive heart failure.

Compounds in accordance with Formula (I) may be used to treat a variety of medical conditions and/or disorders associated with the AR pathway. Formula (I) compounds can modulate the function of the AR by, for example, agonizing, partially agonizing, antagonizing, and/or partially antagonizing the AR. In one embodiment, at least one Formula (I) selectively modulates the function of at least one AR.

Medical conditions associated with the AR pathway include, but are not limited to, for example, hirsutism; acne; seborrhea; Alzheimer's disease; androgenic alopecia; hypogonadism; hyperpilosity; benign prostate hypertrophia; adenomas and neoplasies of the prostate, such as, for example, advanced metastatic prostate cancer; AR containing benign or malignant tumor cells, such as, are found, for example, in breast, brain, skin, ovarian, bladder, lymphatic, liver, and kidney cancers; pancreatic cancers; endometrial cancer; heart disease associated with VCAM expression; inflammatory diseases; immune system related diseases; angiogenesis; osteoporosis; spermatogenesis; libido; cachexia; endometriosis; polycystic ovary syndrome; anorexia; age related decrease of male testosterone levels; male menopause; male hormone replacement; male and female sexual dysfunction; and muscular atrophy in ambulatory patients. For example, pan AR modulation is contemplated, with prostate selective AR modulation ("SARM") being particularly preferred, such as for the treatment of early stage prostate cancers. In one embodiment, at least one Formula (I) compound is used to treat prostate cancer by being employed as an antagonist or partial antagonist of at least one AR.

Formula (I) compounds can be used to antagonize, preferably selectively antagonize, mutated ARs found, for example, in many tumor cell lines. Exemplary mutated ARs, include, but are not limited to, those found in prostate tumor cell lines, such as, for example, LNCap (T877A mutation, *Biophys. Acta,* 187, 1052 (1990)); PCa2b (L701H & T877A mutations, *J. Urol.,* 162, 2192 (1999)); and CWR22 (H874Y mutation, *Mol. Endo.,* 11, 450 (1997)).

Compound in accordance with Formula (I) may be used to treat a variety of medical conditions and/or disorders associated with the SXR pathway. Formula (I) compounds can modulate the function of the SXR by, for example, agonizing, partially agonizing, antagonizing, and/or partially antagonizing the SXR. In one embodiment, at least one Formula (I) compound selectively modulates the function of at least one SXR.

Medical conditions associated with the SXR pathway, include, but are not limited to, for example, disregulation of cholesterol homeostasis; and attenuation of the metabolism of a pharmaceutical agent by co-administering a Formula (I) compound.

Compounds in accordance with Formula (I) may also modulate the function of Orphan receptors, which are NHRs for which the activating or deactivating ligands have not yet been characterized. The Orphan receptors are classified as NHRs due to their strong sequence homology to other NHRs.

Exemplary Orphan receptors include, but are not limited to, the Orphan receptors listed in Table A.

Medical conditions associated with the Orphan receptor pathway include, but are not limited to, for example, the conditions set forth in Table A in the column labeled "Target Therapeutic Application(s)".

TABLE A

Exemplary Orphan NHRs, form(s), tissue expression, and target therapeutic application(s)

| Orphan Receptor | Form (M = monomeric; D = heterodimeric; H = homodimeric) | Tissue Expression | Target Therapeutic Application(s) |
|---|---|---|---|
| NURR1 | M/D | Dopaminergic Neurons | Parkinson's Disease |
| RZRβ | M | Brain (Pituitary); & Muscle | Sleep Disorders |
| RORα | M | Cerebellum & Purkinje Cells | Arthritis & Cerebellar Ataxia |
| NOR-1 | M | Brain; Muscle; Heart; Adrenal; & Thymus | Central Nervous System (CNS) Disorders & Cancer |
| NGFI-Bβ | M/D | Brain | CNS Disorders |
| COUP-TFα | H | Brain | CNS Disorders |
| COUP-TFβ | H | Brain | CNS Disorders |
| COUP-TFγχ | H | Brain | CNS Disorders |
| Nur77 | H | Brain; Thymus; & Adrenals | CNS Disorders |
| Rev-ErbAα | H | Muscle & Brain (ubiquitous) | Obesity |
| HNF4α | H | Liver; Kidneys; & Intestines | Diabetes |
| SF-1 | M | Gonads & Pituitary | Metabolic Disorders |
| LXRα, β | D | Kidneys (ubiquitous) | Metabolic Disorders |
| GCNF | M/H | Testes & Ovaries | Infertility & Osteoporosis |
| ERRα, β | M | Placenta & Bones | Metabolic Disorders |
| FXR | D | Liver & Kidney | Metabolic Disorders |
| CARα | H | Liver & Kidney | Metabolic Disorders |
| PXR | H | Liver & Intestines | Metabolic Disorders |

One embodiment provides a pharmaceutical composition comprising at least one compound in accordance with Formula (I), pharmaceutically-acceptable salt thereof; optionally at least one pharmaceutically-acceptable carrier and/or diluent; and optionally at least one other anti-cancer agent.

Another embodiment provides a method of modulating the function of at least one NHR comprising administering to a patient in need thereof an effective amount of at least one compound of Formula (I), or a pharmaceutically-acceptable salt thereof.

In a further embodiment, the NHR being modulated is the ER, AR, PR, GR, mutated AR, MR, SXR and/or ALDR.

In an even further embodiment, the NHR being modulated is the AR and/or mutated AR.

A still further embodiment provides a method for treating at least one condition or disorder comprising administering to a patient in need thereof a therapeutically effective amount of at least one compound of Formula (I), or a pharmaceutically-acceptable salt thereof; optionally administering either simultaneously or sequentially at least one other anti-cancer agent, and optionally administering either simultaneously or sequentially at least one other anti-cancer treatment.

The phrase "other anti-cancer agent" includes any known agent useful for treating cancer, preferably prostate cancer. In one embodiment, the other anti-cancer agent may work by a different mechanism than the mechanism defined hereinabove. Examples of other such anti-cancer agent(s) include, but are not limited to, for example, antiangiogenic agents, such as, for example, linomide, inhibitors of integrin αvβ3 function, angiostatin, and razoxane; antiestrogens, such as, for example, tamoxifen, toremifene, raloxifene, droloxifene, and iodoxifene; progestogens, such as, for example, megestrol acetate, hydroxyprogesterone, and medroxyprogesterone; aromatase inhibitors, such as, for example, anastrozole, testolactone, letrozole, borazole, and exemestane; antihormones, such as, for example, aminoglutethimide; synthetic estrogens, such as, for example, chlorotrianisene, diethylstilbestrol and 17 α-ethinylestradiol; synthetic androgens, such as for example, dromostanolone propionate, fluoxymesterone, and methyltestosterone; antiprogestogens; antiandrogens, such as, for example, flutamide, nilutamide, bicalutamide, and cyproterone acetate; androgens, such as, for example, testosterone; synthetic glucocorticoids, such as, for example, methylprednisolone, triamcinolone, prednisolone, and prednisone; LHRH agonists and antagonists, such as, for example, gosereline acetate and leuprolide; inhibitors of testosterone 5α-dihydroreductase, such as, for example, finasteride; farnesyltransferase inhibitors; anti-invasion agents, such as, for example, metalloproteinase inhibitors like marimastat and inhibitors of urokinase plasminogen activator receptor function; VEGF inhibitors, such as, for example, anti-VEGF antibodies (Avastin) and small molecules, such as, for example, ZD6474, SU6668, Vatalanib, BAY-43-9006, SU11248, CP-547632, and CEP-7055; Her 1 and Her 2 inhibitors including, for example, anti-Her 2 antibodies (Herceptin); EGFR inhibitors, such as, for example, gefitinib, erlotinib, ABX-EGF, EMD72000, 11F8, and cetuximab; Eg5 inhibitors, such as, for example, SB-715992, SB-743921, and MKI-833; pan Her inhibitors, such as, for example, canertinib, EKB-569, CI-1033, AEE-788, XL-647, mAb 2C4, and GW-572016; Src inhibitors, such as, for example, Gleevac and Dasatinib; MEK-1 inhibitors; MAPK inhibitors; PI3 kinase inhibitors; Met inhibitors; Aurora kinase inhibitors; PDGF inhibitors, such as, for example, imatinib; IGF1R inhibitors, such as, for example, those disclosed in United States Patent Application No. 2004/0044203 A1; other receptor and non-receptor tyrosine kinase inhibitors; other serine/threonine kinase inhibitors; CDK inhibitors; antimetabolites, such as, for example, methotrexate, idatrexate, trimetrexate, 5-fluorouracil, tegafur, cytarabine, fludarabine, 6-thioguanine, DON (d-oxo-norleucine or AT-125) and 6-mercaptopurine; intercalating antitumor antibiotics, such as, for example, doxorubicin, daunomycin, epirubicin, idarubicin, mitomycin-C, dactinomycin, mitoxantrone, and mithramycin; platinum derivatives, such as, for example, cisplatin, oxaliplatin, and carboplatin; alkylating agents, such as, for example, nitrogen mustard, melphalan, chlorambucil, busulphan, cyclophosphamide, ifosfamide nitrosoureas, dacarbazine, hexamethyl melamine, estramustine, and thiotepa; antimitotic agents, such as, for example, vinblastine, vinflunine, Taxol® (paclitaxel), Taxotere® (docetaxel), 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, epothilone analogs, i.e., ixabepilone, and derivatives thereof; inhibitors of integrin signaling; topoisomerase inhibitors, such as, for example, etoposide, teniposide, amsacrine, doxorubicin, daunorubicin, irinotecan, and topotecan; cell cycle inhibitors, such as, for example, flavopyridols; biological response modifiers, such as, for example, interferon-alpha; monoclonal antibodies, such as for example, rituximab, and gemtuzumab ozogamicin; proteasome inhibitors, such as, for example, Velcade® (bortezomib); SN-8; procarbazine; L-asparaginase; pyridobenzoindole derivatives; ribonucleotide reductase inhibitors; mTOR inhibitors; leucovorin; VM-26; interleukins; and hematopoietic growth factors.

The phrase "anti-cancer treatment" includes but is not limited to, for example, radiation therapy and surgery, e.g. castration.

The condition(s) or disorder(s) that can be treated with compounds of Formula (I) include, but are not limited to, for example, NHR associated diseases, such as, for example, cancer; diabetes; psoriasis; rheumatoid arthritis; Kaposi's sarcoma; haemangioma; obesity; acute and chronic nephropathies; atheroma; arterial restenosis; autoimmune diseases; acute inflammation; and ocular diseases associated with retinal vessel proliferation, e.g., diabetic retinopathy.

In one embodiment, at least one compound of Formula (I) is used to treat cancer.

The cancers Formula (I) compound(s) can be used to treat include, but are not limited to, for example, carcinoma, including, for example, that of the bladder, breast, colon, kidney, liver, lung (including small cell lung cancer), esophagus, gall bladder, ovary, pancreas, stomach, cervix, thyroid, prostate, and skin (including squamous cell carcinoma); hematopoietic tumors of lymphoid lineage, such as, for example, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burkett's lymphoma; hematopoietic tumors of myeloid lineage, such as, for example, acute and chronic myelogenous leukemia, myelodysplastic syndrome, and promyelocytic leukemia; tumors of mesenchymal origin, including, for example, fibrosarcoma and rhabdomyosarcoma; tumors of the central and peripheral nervous system, including, for example, astrocytoma, neuroblastoma, glioma, and schwannomas; and other tumors, such as, for example, melanoma, seminoma, teratocarcinoma, osteosarcoma, xeroderma pigmentosum, keratoacanthoma, thyroid follicular cancer, and Kaposi's sarcoma.

In another embodiment, at least one compound of Formula (I) is used to treat prostate cancer, breast cancer, and/or endometrial cancer.

In yet another embodiment, at least one compound of Formula (I) is used to treat adenoma(s) and neoplasie(s) of the prostate.

Compounds in accordance with Formula (I) may modulate apoptosis, and therefore may be useful to, for example, treat cancer, including but not limited to, for example, cancers already mentioned herein above; treat viral infections, including, but not limited to, for example, herpes virus, pox virus, Epstein-Barr virus, Sindbis virus and adenovirus; prevent AIDS from developing in HIV-infected individuals; treat autoimmune diseases, including, but not limited to, for example, systemic lupus, erythematosus, autoimmune mediated glomerulonephritis, rheumatoid arthritis, psoriasis, inflammatory bowel disease, and autoimmune diabetes mellitus; treat neurodegenerative disorders, including, but not limited to, for example, Alzheimer's disease, AIDS-related dementia, Parkinson's disease, amyotrophic lateral sclerosis, retinitis pigmentosa, spinal muscular atrophy, and cerebellar degeneration; treat myelodysplastic syndromes; treat aplastic anemia; treat ischemic injury associated with myocardial infarctions, stroke, and reperfusion injury; treat arrhythmias; treat atherosclerosis; treat toxin-induced or alcohol related liver diseases; treat hematological diseases, including, but not limited to, for example, chronic anemia and aplastic anemia; treating degenerative diseases of the musculoskeletal system, including, but not limited to, for example, osteoporosis and arthritis; treat aspirin-sensitive rhinosinusitis; treat cystic fibrosis; treat multiple sclerosis; treat kidney diseases; and treat cancer pain.

Due to the role kinases play in regulating cellular proliferation in general, inhibitors can act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections. For example, compounds of Formula (I) may be useful to treat tumors associated with tyrosine kinase activity, such as, for example, colon, lung, and pancreatic tumors.

Compounds in accordance with Formula (I) may also modulate the level of cellular RNA and/or DNA synthesis, and as a result could be useful in treating viral infections, including but not limited to, for example, HIV; human papilloma virus; herpes virus; pox virus; Epstein-Barr virus; Sindbis virus; and adenovirus.

Compounds in accordance with Formula (I) may also be useful in the chemoprevention of cancer. Chemoprevention is defined as inhibiting the development of invasive cancer by blocking the initiating mutagenic event, by blocking progression of pre-malignant cells that have already suffered an insult, or by inhibiting tumor relapse.

Compounds in accordance with Formula (I) may also be useful in inhibiting tumor angiogenesis, metastasis, and/or vascular permeability.

In one embodiment, the patient is an animal.

In another embodiment, the patient is a mammalian species including, but not limited to, for example, humans and domestic animals, such as, for example, dogs, cats, and horses.

In yet a further embodiment, the patient is a human.

Compounds in accordance with Formula (I) may be used, for example, in combination with known therapies for treating advanced metastatic prostate cancer including, but not limited to, for example, "complete androgen ablation therapy" wherein tumor growth is inhibited by controlling the supply of androgen to the prostate tissues via chemical castration followed by the administration of at least one AR antagonist. The compounds of Formula (I) can be employed as AR antagonists in complete ablation therapy, alone or in combination with other AR antagonists such as Flutamide, Casodex, Nilutamide, or Cyproterone acetate.

The compounds of Formula (I) may further be employed adjuvant to surgery.

Compounds in accordance with Formula (I) may be used, for example, either in combination with antibody therapy including, but not limited to, for example, antibody therapy against PSCA, or in concert with vaccine/immune modulating agents used to treat cancer.

Compounds in accordance with Formula (I) can be administered by any means suitable for the condition to be treated, which can depend on the need for site-specific treatment or quantity of Formula (I) compound to be delivered.

Any pharmaceutical composition contemplated herein can, for example, be delivered orally via any acceptable and suitable oral preparations. Exemplary oral preparations, include, but are not limited to, for example, tablets; troches; lozenges; aqueous or oily suspensions; dispersible powders or granules; emulsions; hard or soft capsules; syrups; and elixirs. Pharmaceutical compositions intended for oral administration can be prepared according to any methods known in the art for manufacturing pharmaceutical compositions intended for oral administration. In order to provide pharmaceutically elegant and palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinylpyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate buryrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and a hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oil phase can be provided by, but is not limited to, for example, a vegetable oil, such as, for example, olive oil and arachis oil; a mineral oil, such as, for example, liquid paraffin; and mixtures thereof. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. An emulsion can also contain a sweetening agent, a flavoring agent, a preservative, and/or an antioxidant.

Any pharmaceutical composition contemplated herein can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleagenous suspensions.

A sterile injectable oil-in-water microemulsion can, for example, be prepared by 1) dissolving at least one compound of Formula (I) in an oily phase, such as, for example, a mixture of soybean oil and lecithin; combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Any pharmaceutical composition contemplated herein can, for example, further be administered via any acceptable and suitable rectal preparation, including, but not limited to, for example, a suppository. A suppository can be prepared by mixing at least one compound of Formula (I) with at least one suitable non-irritating excipient that is liquid at rectal temperatures but solid at a temperature below rectal temperature. Exemplary non-irritating excipients include, but are not limited to, for example, cocoa butter; glycerinated gelatin; hydrogenated vegetable oils; mixtures of polyethylene glycols of various molecular weights; and fatty acid esters of polyethylene glycol.

Any pharmaceutical composition contemplated herein can, for example, be administered via any acceptable and suitable topical preparations including, but not limited to, for example, creams; ointments; jellies; solutions; suspensions, transdermal patches; and intranasal inhalers. For purposes of this application, topical preparations include mouth washes and gargles.

Exemplary compositions for nasal aerosol or inhalation administration include solutions that may contain, for example, benzyl alcohol or other suitable preservatives, absorption promoters to enhance absorption and/or bioavailability, and/or other solubilizing or dispersing agents such as those known in the art An "effective amount" of Formula (I) compound may be determined by one of ordinary skill in the art, and includes exemplary dosage amounts for a mammal of from about 0.05 to about 300 mg/kg/day, preferably less than about 200 mg/kg/day, in a single dose or in or in the form of individual divided doses. Exemplary dosage amounts for an adult human are from about 1 to 100 (for example, 15) mg/kg of body weight of active compound per day, which can be administered in a single dose or in the form of individual divided doses, such as from 1 to 4 times per day.

The specific dose level and frequency of dosage for any particular subject, however, may be varied and generally depends on a variety of factors, including, but not limited to, for example, the bioavailability of the specific Formula (I) compound(s) in the administered form; metabolic stability and length of action of the specific Formula (I) compound(s); species, age, body weight, general health, sex, and diet of the subject; mode and time of administration; rate of excretion; drug combination; and severity of the particular condition.

The compounds of Formula (I) can also be formulated or co-administered with other therapeutic agents that are selected for their particular usefulness in administering therapies associated with the aforementioned conditions. For example, the compounds of the invention may be formulated with agents to prevent nausea, hypersensitivity, and/or gastric irritation, such as, for example, antiemetics and $H_1$ and $H_2$ antihistaminics.

The above other therapeutic agents, when employed in combination with the compounds of Formula (I), can be used, for example, in those amounts indicated in the Physicians' Desk Reference (PDR) or as otherwise determined by one of ordinary skill in the art.

Assays

Compounds within the scope of Formula (I), including the compounds described in the examples hereinbelow, have been tested in at least one of the assays described below and have shown activity as a modulator of at least one NHR described hereinabove.

MDA-MB-453 Androgen Receptor Transactivation Assay

The compounds of Formula (I) can be tested in a cell based transactivation assay used to measure the antagonism of androgen receptor (AR) transcriptional activity. The transactivation assay provides a means of identifying antagonists that inhibit the effects of the native hormone dihydrotestosterone (DHT). The human breast adenocarcinoma MDA-MB-453 cell line (American Type Culture Collection, Rockville, Md., ATCC#: HTB-131), expressing a functional endogenous wild type AR, was transiently transfected with a reporter plasmid and tested for AR dependent transactivation activity in the absence or presence of test compounds. The pGL3 PSA-Luc reporter plasmid is comprised of the cDNA for the firefly luciferase gene and the upstream promoter sequences containing the androgen response elements (AREs) of the prostate specific antigen (PSA). This plasmid functions as a reporter for the transcription-modulating activity of the AR. In order to detect antagonists, the transactivation assay is conducted in the presence of constant concentration of the natural AR hormone (DHT) to induce a defined reporter signal. Addition of increasing concentrations of the suspected antagonist will decrease the reporter signal (luciferase activity).

MDA-MB-453 cells, maintained in DMEM (Cellgro, Cat. # 10-014-CM) supplemented with 10% FBS (Invitrogen/GIBCO Life Science), were seeded in a 96-well plate at 60,000 cells per well the evening prior to experimentation and incubated at 37° C. with 5% $CO_2$ until time of assay. Cell culture media from the 96-well cell plate was carefully removed by aspiration and each well was transfected with 100 ng pGL3 PSA-Luc plasmid by using the Lipofectamine 2000 Reagent (Invitrogen, Cat. # 11668-019) and serum-free Opti-MEM I media (Invitrogen, Cat# 31985-070) according to the manufacturer's optimized conditions. The transfection was conducted at 37° C. with 5% $CO_2$ for 4 hours.

Following the four hour transfection, DMEM containing 10% Charcoal/Dextran Treated Fetal Bovine Serum (Hyclone, Cat.# SH30068.03) was added to the cell plate. The cells were then incubated in the absence (blank) or presence (control) of 1 nM DHT (Sigma, Cat. # A-8380) and in the presence or absence of the standard antiandrogen bicalutamide or compounds in formula (I), in concentrations ranging from $10^{-10}$ to $10^{-5}$M. Duplicates were used for each sample.

The compound dilutions were performed by the Tecan Genesis (Tecan, Triangle Park, N.C.). After a 48 hour incubation, luciferase activity was measured using the Steady-Glo Luciferase Assay System (Promega, Cat. # E2550) according to manufacturer's specifications and luminescence was measured on a Packard TopCount (PerkinElmer). For each luciferase sample reading, the percent control (in absence of compounds) was calculated as:

% Control=100×[average sample−average blank]/
[average control−average blank]

Data was plotted and the $IC_{50}$ value was defined as the concentration of compound that inhibited 50% of the luciferase activity for the controls.

AR Binding Assay

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, are incubated at 37° C. to remove any endogenous ligand that might be complexed with the receptor in the cells. After 48 hours, either a saturation analysis to determine the $K_d$ for tritiated dihydrotestosterone, [$^3$H]-DHT, or a competitive binding assay to evaluate the ability of test compounds to compete with [$^3$H]-DHT is performed. For the saturation analysis, media (RPMI 1640 or DMEM −0.2% CA-FBS) containing [$^3$H]-DHT (in concentrations ranging from 0.1 nM to 16 nM) in the absence (total binding) or presence (non-specific binding) of a 500-fold molar excess of unlabeled DHT are added to the cells. After 4 hours at 37° C., an aliquot of the total binding media at each concentration of [$^3$H]-DHT is removed to estimate the amount of free [$^3$H]-DHT. The remaining media is removed, cells are washed three times with PBS and harvested onto UniFilter GF/B plates (Packard), Microscint (Packard) is added and plates counted in a Top-Counter (Packard) to evaluate the amount of bound [$^3$H]-DHT.

For the saturation analysis, the difference between the total binding and the non-specific binding, is defined as specific binding. The specific binding is evaluated by Scatchard analysis to determine the $K_d$ for [$^3$H]-DHT. See e.g. D. Rodbard, *Mathematics and Statistics of Ligand Assays: An Illustrated Guide*: In: J. Langon and J. J. Clapp, eds., Ligand Assay, Masson Publishing U.S.A., Inc., New York, pp. 45-99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M are added to the cells. Two replicates are used for each sample. After 4 hours at 37° C., cells are washed, harvested, and counted as described above. The data is plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand is quantified ($IC_{50}$) after log-logit transformation. The $K_1$ values are determined by application of the Cheng-Prusoff equation to the $IC_{50}$ values, where:

$$K_I = \frac{IC_{50}}{(1 + (^3H\text{-}DHT)/K_d \text{ for } ^3H\text{-}DHT)}.$$

After correcting for non-specific binding, $IC_{50}$ values are determined. The $IC_{50}$ is defined as the concentration of competing ligand needed to reduce specific binding by 50%. The $K_d$ values for [$^3$H]-DHT for MDA 453 and LNCaP are 0.7 and 0.2 nM respectively.

Murine Breast Cell Proliferation Assay

The ability of the compounds of Formula (I) to modulate the function of the AR can be determined by testing said compounds in a proliferation assay using the androgen responsive murine breast cell line derived from the Shionogi tumor, Hiraoka et al., *Cancer Res.*, 47, 6560-6564 (1987). Stable AR dependent clones of the parental Shionogi line are established by passing tumor fragments under the general procedures originally described in Tetuo et al., *Cancer Res.*, 25, 1168-1175 (1965). From the above procedure, one stable line, SC114, is isolated, characterized, and utilized for the testing of example compounds. SC114 cells are incubated with or without the test compounds for 72 hours and the amount of [$^3$H]-thymidine incorporated into DNA is quantified as a surrogate endpoint to assess the number of cells and therefore the proliferation rate as described in Suzuki et. al., *J. Steroid Biochem. Mol. Biol.* 37, 559-567 (1990). The SC114 cell line is maintained in MEM containing $10^{-3}$ M testosterone and 2% DCC-treated FCS. For the assay, cells are plated in 96-well microplates in the maintenance media and incubated at 37° C. On the following day, the medium is changed to serum free medium [Ham's F-12:MEM (1; 1, v/v) containing 0.1% BSA] with (antagonist mode) or without (agonist mode) $10^{-3}$ M testosterone and the test compounds of formula (I) in concentrations ranging from $10^{-10}$ to $10^{-5}$ M. Duplicates are used for each sample. The compound dilutions are performed on a Biomek 2000 laboratory work station. Seventy two hours later 0.44 μCi of [$^3$H]-Thymidine (Amersham) is added per well and incubated for another 2 hr followed by tripsinization, and harvesting of the cells onto GF/B filters. Micro-scint PS is added to the filters before counting them on a Beckman TopCount. For the antagonist mode, the % Inhibition is calculated as:

$$\% \text{ Inhibition} = 100 \times (1 - [(\text{average}_{sample} - \text{average}_{blank}) / (\text{average}_{control} - \text{average}_{blank})])$$

Data is plotted and the concentration of compound that inhibited 50% of the [$^3$H]-Thymidine incorporation is quantified ($IC_{50}$).

For the agonist mode % Control is referred as the effect of the tested compound compared to the maximal effect observed with the natural hormone, in this case DHT, and is calculated as:

$$\% \text{ Control} = 100 \times (\text{average}_{sample} - \text{average}_{blank}) / (\text{average}_{control} - \text{average}_{blank})$$

Data is plotted and the concentration of compound that inhibited 50% of the [$^3$H]-Thymidine incorporation is quantified ($EC_{50}$).

Wet Prostate Weight Assay AR Antagonist Assay

The activity of compounds of Formula (I) as AR antagonists can be investigated in an immature male rat model, a standard, recognized test of antiandrogen activity of a given compound, as described in L. G. Hershberger et al., *Proc. Soc. Expt. Biol. Med.*, 83, 175 (1953); P. C. Walsh and R. F. Gittes, "Inhibition of extratesticular stimuli to prostate growth in the castrated rat by antiandrogens", *Endocrinology*, 86, 624 (1970); and B. J. Furr et al., "ICI 176,334: A novel nonsteroid, peripherally selective antiandrogen", *J. Endocrinol.*, 113, R7-9 (1987), the disclosures of which are herein incorporated by reference.

The basis of this assay is the fact that male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et al. *Clin. Invest. Med.,* 16, 475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues. M. C. Luke and D. S. Coffey, "The Physiolog of Reproduction" ed. by E. Knobil and J. D. Neill, 1, 1435-1487 (1994). Since the male sex organs are the tissues most responsive to modulation of the androgen activity, this model is used to determine the androgen dependent growth of the sex accessory organs in immature castrated rats.

Male immature rats (19-20 days old Sprague-Dawley, Harlan Sprague-Dawley) are castrated under metofane anesthesia. Five days after surgery these castrated rats (60-70 g, 23-25 day-old) are dosed for 3 days. Animals are dosed subcutaneously (s.c.) 1 mg/kg with Testosterone Proprionate (TP) in arachis oil vehicle and anti-androgen test compounds (compounds of formula (I)) are dosed orally by gavage (p.o.) in dissolved/suspensions of 80% PEG 400 and 20% Tween 80 surfactant (PEGTW). Animals are dosed (v/w) at 0.5 ml of vehicle/100 g body weight. Experimental groups are as follows:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of formula (I) ("test compound") is administered (p.o. in PEGTW, QD) with TP (s.c. as administered in group 2) in a range of doses.
5. To demonstrate agonist activity a compound of formula (I) ("test compound") is administered alone (p.o. in PEGTW, QD) in a range of doses.

At the end of the 3-day treatment, the animals are sacrificed, and the ventral prostate weighed. To compare data from different experiments, the sexual organs weights are first standardized as mg per 100 g of body weight, and the increase in organ weight induced by TP was considered as the maximum increase (100%). ANOVA followed by one-tailed Student or Fischer's exact test is used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases seminal vesicles (SV) and the ventral prostate (VP) in a dose dependent manner.

The maximum increase in organ weight is 4 to 5-fold when dosing 3 mg/rat/day of testosterone (T) or 1 mg/rat/day of testosterone propionate (TP) for 3 days. The $EC_{50}$ of T and TP are about 1 mg and 0.03 mg, respectively. The increase in the weight of the VP and SV also correlates with the increase in the serum T and DHT concentration. Although administration of T shows 5-times higher serum concentrations of T and DHT at 2 hours after subcutaneous injection than that of TP, thereafter, these high levels decline very rapidly. In contrast, the serum concentrations of T and DHT in TP-treated animals are fairly consistent during the 24 hours, and therefore, TP showed about 10-30-fold higher potency than free T.

In this immature castrated rat model, a known AR antagonist (Casodex) is also administered simultaneously with 0.1 mg of TP ($ED_{80}$), inhibiting the testosterone-mediated increase in the weights of the VP and SV in a dose dependent manner. The antagonist effects are similar when dosing orally or subcutaneously. Compounds of the invention also exhibit AR antagonist activity by suppressing the testosterone-mediated increase in the weights of VP and SV.

CWR22 Human Prostate Zenograft Assay

In Vivo Antitumor Testing: CWR22 human prostate tumors are maintained in Balb/c nu/nu nude mice. Tumors are propagated as subcutaneous transplants in adult male nude mice (4-6 weeks old) using tumor fragments obtained from donor mice. Tumor passage occurs every 5-6 weeks.

For antitumor efficacy trial, the required number of animals needed to detect a meaningful response are pooled at the start of the experiment and each is given a subcutaneous implant of a tumor fragment (~50 mg) with a 13-gauge trocar. Tumors are allowed to grow to approx. 100-200 mg (tumors outside the range were excluded) and animals are evenly distributed to various treatment and control groups. Treatment of each animal is based on individual body weight. Treated animals are checked daily for treatment related toxicity/mortality. Each group of animals is weighed before the initiation of treatment ($Wt_1$) and then again following the last treatment dose ($Wt_2$). The difference in body weight ($Wt_2-Wt_1$) provides a measure of treatment-related toxicity.

Tumor response is determined by measurement of tumors with a caliper twice a week, until the tumors reach a predetermined "target" size of 0.5 gm. Tumor weights (mg) are estimated from the formula: Tumor weight=(length×width$^2$)÷2.

Tumor response end-point is expressed in terms of tumor growth inhibition (% T/C), defined as the ratio of median tumor weights of the treated tumors (T) to that of the control group (C).

To estimate tumor cell kill, the tumor volume doubling time is first calculated with the formula:

TVDT=[(Median time (days) for control tumors to reach target size)−(Median time (days) for control tumors to reach half the target size)].

And, Log cell kill=(T−C)÷(3.32×TVDT)

Statistical evaluations of data are performed using Gehan's generalized Wilcoxon test.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

The following abbreviations are employed in the schemes and Examples set froth herein: $CH_2Cl_2$=dichloromethane; $CH_3CN$=acetonitrile: DAST=(Diethylamino)sulfur trifluoride; DIAD=diisopropyl azodicarboxylate; DMA=dimethylacetamide; EtOH=ethanol; EtOAc=ethyl acetate; HPLC=high pressure chromatography; LC-MS=liquid chromatography–mass spectroscopy; LiHMDS=lithium bis(trimethylsilyl)amide; MCPBA=3-chloroperoxybenzoic acid (approx. 77%); MeI=iodomethane; MeOH=methanol; PhMe=toluene; Pd/C=palladium on carbon; RT=room temperature; TLC=thin layer chromatography; THF=tetrahydrofuran; HCl=hydrochloric acid; KOH=potassium hydroxide; min=minutes; hrs=hours; $H_3PO_4$=phosphoric acid; $NaHCO_3$=sodium bicarbonate; $NaBH_4$=sodium borohydride; $NH_4Cl$=ammonium chloride; $Na_2SO_4$=sodium sulfate; $H_2O_2$=hydrogen peroxide; $BH_3$-THF=borane-tetrahydrofuran complex; HOAc:=acetic acid; $MgSO_4$=magnesium sulfate; $Na_2SO_3$=sodium sulfite; $N_2$=nitrogen; Prep HPLC=reverse phase preparative HPLC; temp=temperature; $K_2CO_3$=potassium carbonate; NaI=sodium iodide; NaH=sodium hydride; DIPEA=N,N-diisopropylethylamine; KCN=potassium cyanide; $PMe_3$=trimethylphosphine; $OSO_4$=osmium tetraoxide; $Bu_4CN$=tetrabutylammonium cyanide; $NaN_3$=sodium azide; KF=potassium fluoride; $Hg(OAc)_2$=mercuric acetate; $Et_2O$=diethyl ether; and $Et_3N$=triethyl amine.

Example 1

Rac-4-((1R,2S,6S,7S)-3,3-dioxido-3-thia-4-azatricyclo[5.2.1.0$^{2,6}$]dec-8-en-4-yl)-2-(trifluoromethyl)benzonitrile

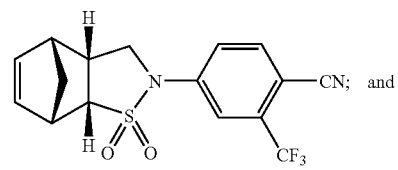

1K

Rac-4-((1R,2R,6R,7S)-3,3-dioxido-3-thia-4-azatricyclo[5.2.1.0$^{2,6}$]dec-8-en-4-yl)-2-(trifluoromethyl)benzonitrile

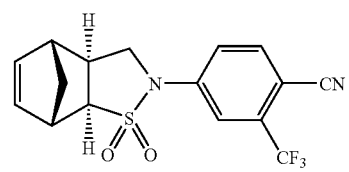

1L 1A. 3,3'-disulfanediyldipropanoyl chloride

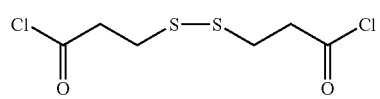

1A

Thionyl chloride (69.2 mL, 951 mmol) was added to a mixture of dithiopropionic acid (50.0 g, 238 mmol) and pyridine (0.1 mL) at 22° C. followed by stirring for 16 hrs. The reaction mixture was vented into a scrubbing solution of KOH in $H_2O$ to trap the HCl produced by the reaction. The mixture started out heterogeneous and became a clear amber solution after stirring overnight. The mixture was concentrated in vacuo to give 62 g of 1A as a yellow oil, which was stored under argon at 0° C.

1B. 3,3'-disulfanediylbis(N-(4-cyano-3-(trifluoromethyl)phenyl)propanamide)

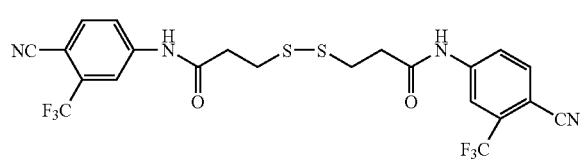

1A (10.0 g; 40.4 mmol; 1.0 equiv), neat, was added via syringe to a clear amber solution of 2-trifluoromethyl-4-aminobenzonitrile (14.9 g; 80.8 mmol; 2.0 equiv) in 80 mL dry THF at 22° C. A slight exotherm was observed. The homogeneous amber solution was stirred for 20 min, and then placed in a 55° C. oil bath for 30 min. HPLC indicated only a small amount of aniline was present. The contents of the reactor were concentrated in vacuo to yield a tan solid. After absorption onto silica, the crude material was purified by flash column chromatography (1% acetone/CH$_2$Cl$_2$ to elute aniline, then 10-50% acetone/CH$_2$Cl$_2$ to elute desired as a pale yellow band.) to give 20.3 g (94%) of 1B as an off-white solid. HPLC: 95% at 3.736 min (retention time) (YMC ODS-A column 4.6×50 mm eluting with 10-90% aqueous MeOH over 4 min containing 0.1% H$_3$PO$_4$, 4 mL/min, monitoring at 220 nm).

1C. 4-(3-oxo-2(3H)-isothiazolyl)-2-(trifluoromethyl)benzonitrile

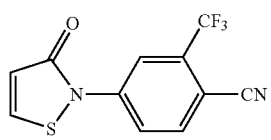

Sulfuryl chloride (5.80 mL, 71.3 mmol)) in PhMe (10 mL) was added via an addition funnel over 0.5 hr to a suspension of 1B (13.0 g, 23.8 mmol) in PhMe (50 mL) at 50° C. After completing the addition, the reaction mixture became clear, and then cloudy and viscous. After waiting 6 hrs, the reaction mixture was cooled to 22° C., filtered, and then rinsed with PhMe. The resulting white solid was briefly dried under high vacuum followed by slurrying with water. The resulting slurry was stirred for 10 min followed by filtration and drying under high vacuum. After drying, 10.9 g (85%) of 1C was isolated as a pale yellow solid. HPLC: 98% at 2.575 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 269.06 [M−H]$^-$.

1D. 4-(1,1-dioxido-3-oxo-2(3H)-isothiazolyl)-2-(trifluoromethyl)benzonitrile

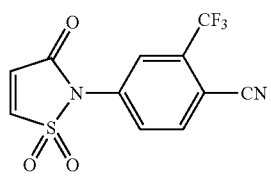

1C (10.00 g, 37.0 mmol) was dissolved in CH$_2$Cl$_2$ (400 mL) and mCPBA (77%, 20.0 g, 81.5 mmol) was added at 22° C. After 10 min, LC-MS showed no starting material remained. After 20 min, 3-hydroxypyridine (3.51 g, 37.0 mmol) was added over a 2 minute period with vigorous stirring producing a slight exotherm. After 5 min, saturated aqueous NaHCO$_3$ (300 mL) was added with vigorous stirring. After stirring for 5 min, the solution was transferred to a separatory funnel and the organic layer separated. The organic layer was washed once with a 1:1 solution of brine and saturated aqueous NaHCO$_3$ (300 mL) and then dried over anhydrous Na$_2$SO$_4$. Concentration in vacuo gave 10.2 g of 1D as a pale yellow solid. HPLC: 99% at 2.680 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 301.02 [M−H]$^-$.

1E and 1F. 4-((1S,2R,6R,7R)-3,3-dioxido-5-oxo-3-thia-4-azatricyclo[5.2.1.0$^{2,6}$]dec-8-en-4-yl)-2-(trifluoromethyl)benzonitrile

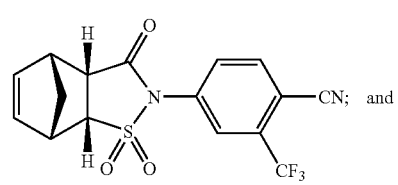

4-((1S,2S,6S,7R)-3,3-dioxido-5-oxo-3-thia-4-azatricyclo[5.2.1.0$^{2,6}$]dec-8-en-4-yl)-2-(trifluoromethyl)benzonitrile

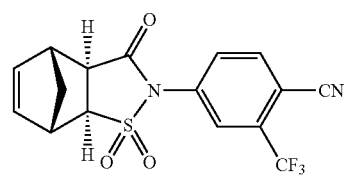

Cyclopentadiene (2.0 g, 30.0 mmol) was added to a solution of 1D (3.00 g, 7.5 mmol) in CH$_2$Cl$_2$ (10 mL). The reaction mixture was stirred at 22° C. under N$_2$ for 30 min. Solvent was removed and hexane (30 mL) was added. The resulting solid was filtered and rinsed with hexane to give 3.4 g of a racemic mixture (98% yield)of 1E and 1F as a white solid. 1E and 1F were separated by flash chromatography on SiO$_2$ eluting with 0-33% EtOAc in heptane to give 1E (3.22 g) and 1F (0.166 g) each as a white solid.

1E: HPLC: 99% at 3.295 min (retention time) (YMC ODS-A column 4.6×50 mm eluting with 10-90% aqueous MeOH over 4 min containing 0.1% H$_3$PO$_4$, 4 mL/min, monitoring at 220 nm); MS (ES): m/z 465.24 [M+H]$^+$; and $^1$H NMR: CDCl$_3$ (ppm) 7.8 (1H, d, J=8.3 Hz), 7.7 (1H, s), 7.6 (1H, d, J=6.38 Hz), 6.4 (1H, m), 6.3 (1H, m), 4.3 (1H, m), 3.9 (1H, m), 3.6 (2H, m), 1.8 (1H, m), 1.6 (1H, m).

1F: HPLC: 99% at 3.31 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 465.24 [M+H]$^+$.

1G. (1S,2R,3R,4R)—N-(4-cyano-3-(trifluoromethyl)phenyl)-3-(hydroxymethyl)bicyclo[2.2.1]hept-5-ene-2-sulfonamide

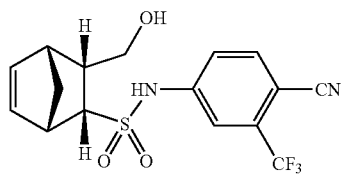

1G

NaBH$_4$ (1.14 g, 30.0 mmol) was added to a solution of 1E (2.5 g, 6.79 mmol) in THF (50 mL) and MeOH (50 mL) at 22° C. The resulting reaction mixture was stirred for 2 hrs, then acidified by addition of a saturated NH$_4$Cl solution (250 mL), and extracted with CH$_2$Cl$_2$ (3×250 mL). The organic phases were combined, dried over anhydrous Na$_2$SO$_4$, and filtered. The filtrate was concentrated in vacuo to give 2.5 g of 1G (a racemic mixture of 1H and 1J hereinbelow) as a white solid. HPLC: 98% at 3.048 min (retention time) (YMC ODS-A column 4.6×50 mm eluting with 10-90% aqueous MeOH over 4 min containing 0.1% H$_3$PO$_4$, 4 mL/min, monitoring at 220 nm); MS (ES): m/z 371.26 [M–H]$^+$; and $^1$H NMR: CDCl$_3$ (ppm) 7.7 (1H, d, J=8.4 Hz), 7.6 (2H, m), 6.3 (1H, m), 6.1 (1H, m), 3.9 (2H, m), 3.6 (1H, m), 3.3 (1H, s), 2.9 (1H, s), 2.7 (1H, m), 1.5 (1H, m), 1.3 (1H, m).

1H and 1J. (1S,2R,3R,4R)—N-(4-cyano-3-(trifluoromethyl)phenyl)-3-(hydroxymethyl)bicyclo[2.2.1]hept-5-ene-2-sulfonamide

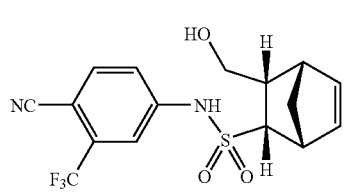

1H (1R,2S,3S,4S)—N-(4-cyano-3-(trifluoromethyl)phenyl)-3-(hydroxymethyl)bicyclo[2.2.1]hept-5-ene-2-sulfonamide

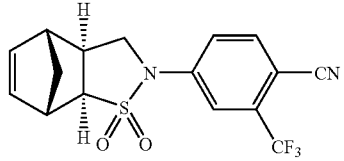

1J 1G (the racemic mixture of 1H and 1J) was separated into individual antipodes by preparative chiral HPLC using a supercritical fluid system. A Chiralpak AD column (250×4.6 mm) was used in a mobile phase of 75% CO$_2$/25% MeOH at 100 bar and 35° C., and a flow rate of 2 mL/min. 1H had a retention time of 3.00 min and 1J had a retention time of 3.97 min. 1H and 1J were each found to be >99% ee by the same analytical method. The absolute stereochemistries of 1H and 1J were established via single crystal X-ray diffraction studies. The SO$_2$ was found to be of sufficient mass to determine the absolute stereochemistry without the use of a chiral appendage. Vibrational Circular Dichroism studies confirmed the absolute stereochemical assignments of 1H and 1J.

1K. Rac-4-((1R,2S,6S,7S)-3,3-dioxido-3-thia-4-azatricyclo[5.2.1.0$^{2,6}$]dec-8-en-4-yl)-2-(trifluoromethyl)benzonitrile

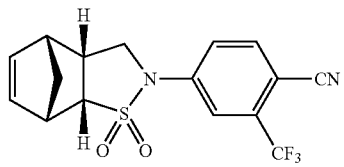

1K

To a solution of 1G (2.0 g, 5.37 mmol) in THF (20 mL) was added triphenyl phosphine (2.1 g, 8.0 mmol) followed by DIAD (1.59 mL, 8.0 mmol). The reaction mixture was stirred at 22° C. under N$_2$ for 1 hr and then concentrated in vacuo to give a crude material, which was purified with flash chromatography using an ISCO system (Isco, Inc., Lincoln, Nebr.) with a 120 g column, flow rate: 85 mL/min, solvent A: CH$_2$Cl$_2$, and solvent B: EtOAc. Gradient: 0% B to 20% B in 25 min to give 1.4 g 1K (76% yield) (in racemic form) as a white solid. HPLC: 99% at 3.265 min (retention time) (YMC ODS-A column 4.6×50 mm eluting with 10-90% aqueous MeOH over 4 min containing 0.1% H$_3$PO$_4$, 4 mL/min, monitoring at 220 nm); MS (ES): m/z 413.24 [M–H+ OAc]$^-$; and $^1$H NMR: CD$_3$COCD$_3$ (ppm) 7.9 (1H, d, J=8.8 Hz), 7.6 (1H, s), 7.56 (1H, m), 6.2 (2H, m), 4.1 (1H, m), 3.7 (1H, m), 3.6 (1H, m), 3.4 (2H, m), 3.17 (1H, s), 1.5 (2H, s).

1L. Rac-4-((1R,2R,6R,7S)-3,3-dioxido-3-thia-4-azatricyclo[5.2.1.0$^{2,6}$]dec-8-en-4-yl)-2-(trifluoromethyl)benzonitrile

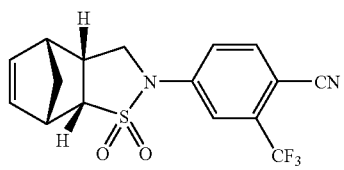

1L 1L was prepared in racemic form from 1F in accordance with the procedures utilized in preparing 1G and 1K. HPLC: 99% at 3.265 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 413.24 [M–H+ OAc]$^-$.

Example 2

4-((1S,2R,6R,7R)-3,3-dioxido-3-thia-4-azatricyclo[5.2.1.0$^{2,6}$]dec-8-en-4-yl)-2-(trifluoromethyl)benzonitrile Example 2 was prepared from 1H in accordance with the general procedures utilized in preparing 1K. Absolute stereochemistry is as drawn. HPLC: 98% at 3.262 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 413.24 [M–H+ OAc]⁻.

Example 3

4-((1R,2S,6S,7S)-3,3-dioxido-3-thia-4-azatricyclo[5.2.1.0$^{2,6}$]dec-8-en-4-yl)-2-(trifluoromethyl)benzonitrile

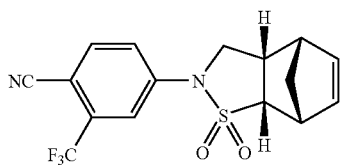

Example 3 was prepared from 1K in accordance with the general procedures utilized in preparing 1K. Absolute stereochemistry is as drawn. HPLC: 99% at 3.266 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 413.24 [M–H+ OAc]⁻.

Example 4

4-((1R,2R,6R,7S)-3,3-dioxido-3-thia-4-azatricyclo[5.2.1.0$^{2,6}$]dec-4-yl)-2-(trifluoromethyl)benzonitrile

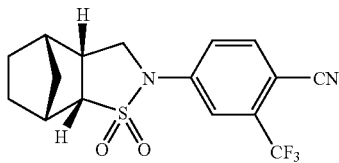

10% Pd/C (0.010 g) was added to a solution of Example 2 (0.025 g, 0.070 mmol) in EtOAc (10 mL). The reaction mixture was stirred under a $H_2$ balloon at 1 atmosphere for 2.5 hrs. Next, the reaction mixture was filtered through celite and the filtrate was concentrated in vacuo to give 0.025 g Example 4 (99% yield) as a white solid. HPLC: 98% at 3.26 min (retention time) (YMC ODS-A column 4.6×50 mm eluting with 10-90% aqueous MeOH over 4 min containing 0.1% $H_3PO_4$, 4 mL/min, monitoring at 220 nm); MS (ES): m/z 414.97 [M–H+ OAc]⁻; and ¹H NMR: CDCl$_3$ (ppm) 7.75 (1H, m), 7.65 (2H, m), 7.55 (1H, d, J=7.3 Hz), 3.65 (1H, m), 3.55 (2H, m), 2.95 (1H, m), 2.8 (1H, s), 2.55 (1H, s), 2.25 (1H, m), 1.5 (5H, m).

Example 5

4-((1S,2S,6S,7R)-3,3-dioxido-3-thia-4-azatricyclo[5.2.1.0$^{2,6}$]dec-4-yl)-2-(trifluoromethyl)benzonitrile

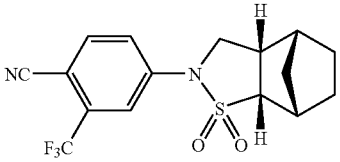

Example 5 was prepared from Example 3 in accordance with the general procedures utilized in preparing Example 4 (i.e., Example 3 instead of Example 2 was used as the starting material). HPLC: 98% 3.29 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 415.22 [M–H+OAc]⁻.

Example 6

4-((1S,2S,6R,7R,9S)-9-hydroxy-3,3-dioxido-3-thia-4-azatricyclo[5.2.1.0$^{2,6}$]dec-4-yl)-2-(trifluoromethyl)benzonitrile

6A

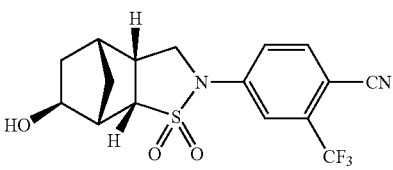

4-((1S,2R,6R,7S,8R)-8-hydroxy-3,3-dioxido-3-thia-4-azatricyclo[5.2.1.0$^{2,6}$]dec-4-yl)-2-(trifluoromethyl)benzonitrile

6B

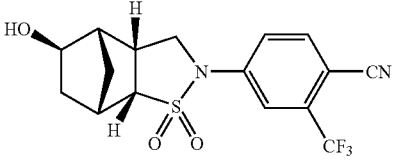

BH$_3$.THF (1.0 M solution in THF, 1.0 mL, 1.0 mmol) was added drop-wise to a solution of Example 2 (0.090, 0.254 mmol) in THF (1.5 mL) at 0° C. The reaction mixture was stirred at 0° C. for 1.5 hrs. Next, phosphate buffer (pH 7.4, 3.0 mL) was added followed by the addition of $H_2O_2$ (30% in $H_2O$, 3.0 mL). The reaction mixture was stirred for 2 hrs, and subsequently diluted with EtOAc. The organic layer was separated and stirred with 10% Na$_2$SO$_3$ (5.0 mL) for 20 min. The organic layer was separated and washed with brine, dried over MgSO$_4$, and filtered. The filtrate was concentrated in vacuo and purified with flash chromatography using an ISCO system (Isco, Inc., Lincoln, Nebr.) with a 40 g column, flow rate: 40 mL/min, solvent A: CH$_2$Cl$_2$, and solvent B: EtOAc. Gradient: 0% B to 60% B in 25 min to give 0.027 g 6A and 0.017 g 6B each as white solids.

6A: HPLC: 98% at 2.512 min (retention time) (YMC ODS-A column 4.6×50 mm eluting with 10-90% aqueous MeOH over 4 min containing 0.1% H$_3$PO$_4$, 4 mL/min, monitoring at 220 nm); MS (ES): m/z 431.04 [M–H+ OAc]$^-$; and $^1$H NMR: CDCl$_3$ (ppm) 7.81 (1H, d, J=8.25 Hz), 7.71 (1H, s), 7.69 (1H, m), 4.76 (1H, d, J=6.60 Hz), 3.72 (1H, m), 3.65 (1H, m), 3.51 (1H, d, J=9.9 Hz), 2.94 (1H, m), 2.82 (1H, d, J=4.4 Hz), 2.58 (1H, s), 2.05 (2H, m), 1.44 (2H, m).

6B: HPLC: 98% at 2.635 min (retention time) (YMC ODS-A column 4.6×50 mm eluting with 10-90% aqueous MeOH over 4 min containing 0.1% H$_3$PO$_4$, 4 mL/min, monitoring at 220 nm); MS (ES): m/z 431.07 [M–H+ OAc]$^-$; and $^1$H NMR: CDCl$_3$ (ppm) 7.79 (1H, M), 7.67 (2H, M), 3.99 (1H, d, J=6.6 Hz), 3.70 (1H, m), 3.68 (1H, d, J=9.9 Hz), 3.55 (1H, m), 3.04 (1H, m), 2.90 (2H, m), 2.54 (1H, d, J=4.9 Hz), 2.01 (2H, m), 1.55 (2H, m).

Example 7

4-((1R,2S,6S,7R,8S)-8-hydroxy-3,3-dioxido-3-thia-4-azatricyclo[5.2.1.0$^{2,6}$]dec-4-yl)-2-(trifluoromethyl)benzonitrile

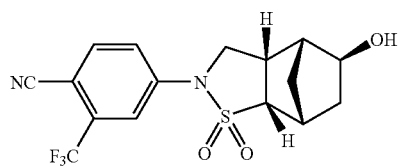

7A 4-((1R,2R,6S,7S,9R)-9-hydroxy-3,3-dioxido-3-thia-4-azatricyclo[5.2.1.0$^{2,6}$]dec-4-yl)-2-(trifluoromethyl)benzonitrile

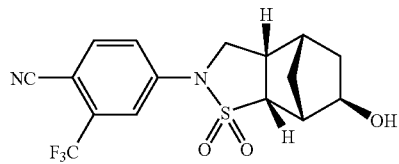

7B 7A and 7B were prepared from Example 3 in accordance with the general procedures utilized in preparing Example 6 (i.e., Example 3 instead of Example 2 was used as the starting material).

7A: HPLC: 99% at 2.65 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 431.21 [M–H]$^+$.

7B: HPLC: 98% at 2.52 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 431.21 [M–H]$^+$.

Example 8

4-((1S,2S,6R,7R)-3,3-dioxido-9-oxo-3-thia-4-azatricyclo[5.2.1.0$^{2,6}$]dec-4-yl)-2-(trifluoromethyl)benzonitrile

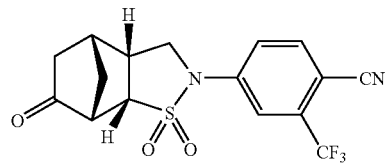

To a solution of 6A (0.26 g, 0.70 mmol) in CH$_2$Cl$_2$ (13 mL) at 22° C. was added Dess-Martin periodinane (0.89 g, 2.1 mmol). The reaction mixture was stirred at 22° C. for 24 hrs. Next, saturated NaHCO$_3$ (15 mL) was added, followed by the addition of 10% Na$_2$SO$_3$ (15 mL). The reaction mixture was stirred at 22° C. for 20 min. The organic layer was separated and washed with brine, dried over MgSO$_4$, and filtered. The filtrate was concentrated in vacuo to give 0.23 g of Example 8 as an off white solid. HPLC: 98% at 2.35 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 369.22 [M–H]$^-$.

Example 9

4-((1R,2R,6S,7S)-3,3-dioxido-9-oxo-3-thia-4-azatricyclo[5.2.1.0$^{2,6}$]dec-4-yl)-2-(trifluoromethyl)benzonitrile

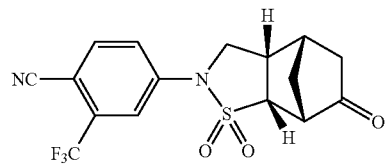

Example 9 was prepared from 7B in accordance with the general procedures utilized in preparing Example 8. HPLC: 98% at 2.35 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 369.22 [M–H]$^-$.

Example 10

4-((1S,2S,6R,7R,9R)-9-(benzylamino)-3,3-dioxido-3-thia-4-azatricyclo[5.2.1.0$^{2,6}$]dec-4-yl)-2-(trifluoromethyl)benzonitrile

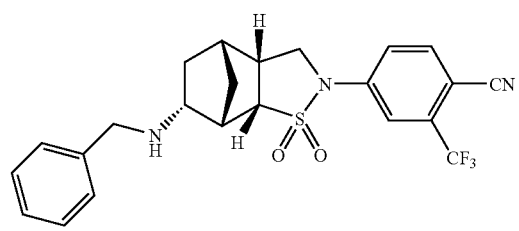

To a solution of Example 8 (0.022 g, 0.059 mmol) in CH₂Cl₂ (1.0 mL) at 22° C. was added benzyl amine (0.019 mL 0.18 mmol) followed by HOAc (0.020 mL, 0.36 mmol). The reaction mixture was heated at 80° C. under microwave heating for 10 hrs, and then concentrated in vacuo to give the crude material as an imine intermediate. The imine was dissolved in MeOH (1.0 mL) at 22° C. and NaBH₄ (0.014 g, 0.356 mmol) was added. The reaction mixture was stirred at 22° C. under N₂ for 2 hrs, and then diluted with EtOAc (10 mL). The organic layer was separated and washed with brine, dried over MgSO₄, and filtered. The filtrate was concentrated in vacuo and purified with a preparative TLC plate, eluting with 50% EtOAc/CH₂Cl₂ to give 0.020 g Example 10 (74% yield) as a light yellow solid. HPLC: 98% at 2.56 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 462.18 [M−H]⁻.

Example 11

4-((1R,2S,6S,7R,9S)-3,3-dioxido-9-(2-phenylethyl)-3-thia-4-azatricyclo[5.2.1.0²,⁶]dec-4-yl)-2-(trifluoromethyl)benzonitrile

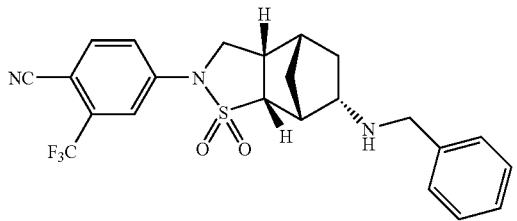

Example 11 was prepared from Example 9 in accordance with the general procedures utilized in preparing Example 10. HPLC: 98% at 2.56 min (retention time) (YMC ODS-A column 4.6×50 mm eluting with 10-90% aqueous MeOH over 4 min containing 0.1% H₃PO₄, 4 mL/min, monitoring at 220 nm). MS (ES): m/z 462.18 [M−H]⁻.

Example 12

4-((1S,2S,6R,7R,9R)-9-hydroxy-3,3-dioxido-3-thia-4-azatricyclo[5.2.1.0²,⁶]dec-4-yl)-2-(trifluoromethyl)benzonitrile

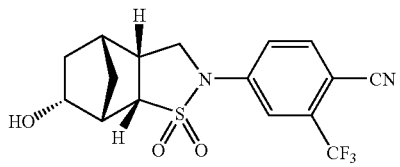

NaBH₄ (0.004 g, 0.108 mmol) was added to a solution of Example 8 (0.020 g, 0.054 mmol) in MeOH (1.0 mL) at 22° C. The reaction mixture was stirred at 22° C. under N₂ for 2 hrs and then diluted with EtOAc (10 mL). The organic layer was washed with saturated NH₄Cl, brine, dried over MgSO₄, and filtered. The filtrate was concentrated in vacuo to give 0.019 g Example 12 (95% yield) as a white solid. HPLC: 98% at 2.45 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 373.29 [M+H]⁺.

Example 13

4-((1R,2R,6S,7S,9S)-9-hydroxy-3,3-dioxido-3-thia-4-azatricyclo[5.2.1.0²,⁶]dec-4-yl)-2-(trifluoromethyl)benzonitrile

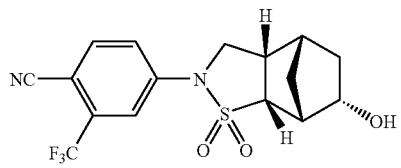

Example 13 was prepared from Example 9 in accordance with the general procedures utilized in preparing Example 12. HPLC: 98% at 2.45 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 373.29 [M−H]⁻.

Example 14

Rac-4-((1R,2R,6S,7R,8R,9S)-8,9-dihydroxy-3,3-dioxido-3-thia-4-azatricyclo[5.2.1.0²,⁶]dec-4-yl)-2-(trifluoromethyl)benzonitrile

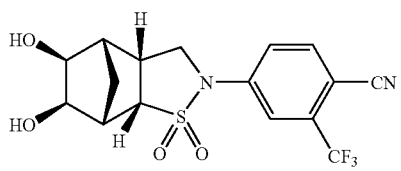

To a solution of 1K (0.050 g, 0.14 mmol) in acetone (2.0 mL) at 22° C. was added 4-morpholine N-oxide (0.025 g, 0.21 mmol) followed by 4% osmium tetra oxide in water solution (0.018 mL, 0.0028 mmol). The reaction mixture was stirred at 22° C. under N₂ for 2 hrs and then concentrated in vacuo. The concentrate was purified with preparative TLC plate, eluting with 50% EtOAc/CH₂Cl₂ to give 0.020 g racemic Example 14 (37% yield) as a white solid. HPLC: 98% at 2.36 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 447.15 [M−H+OAc]⁻.

Example 15

Rac-4-((1R,2R,6S,7R,8R,10S)-3,3-dioxido-9-oxa-3-thia-4-azatetracyclo[5.3.1.0$^{2,6}$.0$^{8,10}$]undec-4-yl)-2-(trifluoromethyl)benzonitrile

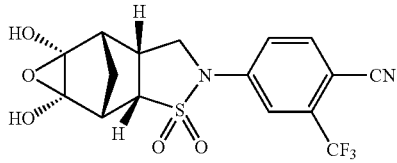

To a solution of 1K (0.25 g, 0.71 mmol) in CH$_2$Cl$_2$ (15 mL) at 22° C. was added mCPBA (0.47 g, 2.1 mmol). The reaction mixture was stirred at 22° C. under N$_2$ for 15 hrs, and then 3-hydroxyl pyridine (0.45 g, 4.7 mmol) was added. The reaction mixture was stirred at 22° C. for 25 min., diluted with EtOAc, washed with saturated NaHCO$_3$ (100 mL), brine, dried over MgSO$_4$, and filtered. The filtrate was concentrated in vacuo to give 0.25 g racemic Example 15 (96% yield) as a white solid. HPLC: 95% at 2.86 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 429.15 [M−H+ OAc]$^−$.

Example 16

Rac-4-((1R,2R,6S,7R,8S,9S)-8-azido-9-hydroxy-3,3-dioxido-3-thia-4-azatricyclo[5.2.1.0$^{2,6}$]dec-4-yl)-2-(trifluoromethyl)benzonitrile

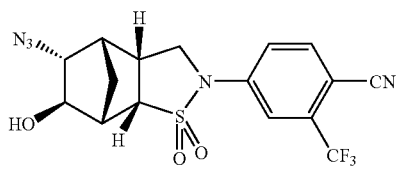

Sodium azide (0.087 g, 1.34 mmol) and NH$_4$Cl (0.046 g, 0.844 mmol) were added to a suspension of Example 15 (0.050 g, 0.134 mmol) in MeOH/water (8/1, 2 mL). The reaction mixture was heated at 100° C. in a sealed tube for 14 days. The pH of the solution was adjusted to and extracted with 10% isopropyl alcohol/EtOAc. The organic layer was separated and washed with brine, dried over MgSO$_4$, and filtered to give 0.046 g of racemic Example 16 (84% yield) as a light yellow solid. HPLC: 98% at 2.35 min (retention time) (YMC ODS-A column 4.6×50 mm eluting with 10-90% aqueous MeOH over 4 min containing 0.1% H$_3$PO$_4$, 4 mL/min, monitoring at 220 nm). MS (ES): m/z 414.12 [M+H]$^+$.

Example 17

4-((1S,2S,6R,7R,9S)-9-fluoro-3,3-dioxido-3-thia-4-azatricyclo[5.2.1.0$^{2,6}$]dec-4-yl)-2-(trifluoromethyl)benzonitrile

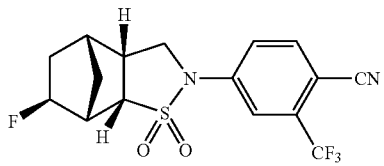

DAST (0.018 mL, 0.134 mmol) was added slowly to a solution of 6A (0.025 g, 0.067 mmol) in CH$_2$Cl$_2$ (0.5 mL) at 22° C. The reaction mixture was stirred at 22° C. under N$_2$ for 15 hrs and then purified by Prep HPLC to give 0.012 g Example 17 (49% yield) as a white solid. HPLC: 96% at 3.15 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 375.29 [M+H]$^+$.

Example 18

4-((1R,2R,6S,7S,9R)-9-fluoro-3,3-dioxido-3-thia-4-azatricyclo[5.2.1.0$^{2,6}$]dec-4-yl)-2-(trifluoromethyl)benzonitrile

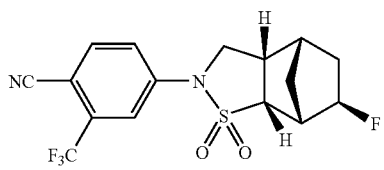

Example 18 was prepared from Example 7B in accordance with the general procedures utilized in preparing Example 17. HPLC: 97% at 3.15 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 375.29 [M+H]$^+$.

Example 19

4-((1S,2S,6R,7R,9S)-9-methoxy-3,3-dioxido-3-thia-4-azatricyclo[5.2.1.0$^{2,6}$]dec-4-yl)-2-(trifluoromethyl)benzonitrile

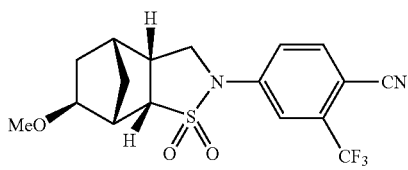

To a solution of 6A (0.040 g, 0.108 mmol) in CH$_3$CN (1.0 mL) at 22° C. was added MeI (0.67 mL, 10.8 mmol). The reaction mixture was stirred at 75° C. in a sealed vial for 2 hrs. The resulting solid was removed by filtration, and purified with Prep HPLC to give 0.030 g Example 19 (72% yield) as a white solid. HPLC: 97% at 3.03 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 445.19 [M−H+ OAc]⁻.

Example 20

4-((1R,2R,6S,7S,9R)-9-methoxy-3,3-dioxido-3-thia-4-azatricyclo[5.2.1.0$^{2,6}$]dec-4-yl)-2-(trifluoromethyl)benzonitrile

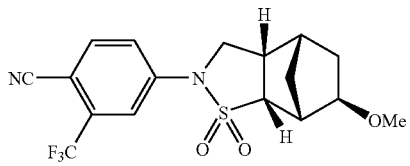

Example 20 was prepared from 7B in accordance with the general procedures utilized in preparing Example 19. HPLC: 97% at 3.028 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 445.19 [M−H]⁻.

Example 21

Rac-4-((1S,2S,6R,7S,8R,9R)-8-chloro-9-hydroxy-3,3-dioxido-3-thia-4-azatricyclo[5.2.1.0$^{2,6}$]dec-4-yl)-2-(trifluoromethyl)benzonitrile

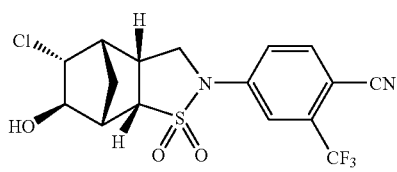

To a solution of Example 15 (0.050 g, 0.135 mmol) in $CH_2Cl_2$ (0.5 mL) at 22° C. was added 12N HCl (1.0 mL, 0.18 mmol). The reaction mixture was stirred at 22° C. for 15 hrs and then diluted with $CH_2Cl_2$ (5 mL). The organic layer was separated and washed with brine, dried over $MgSO_4$, and filtered. The filtrate was concentrated in vacuo and purified with flash chromatography by an ISCO chromatography system using a 4 g column, flow rate: 30 mL/min, solvent A: $CH_2Cl_2$, and solvent B: EtOAc. Gradient: 0% B to 20% B in 25 min to give 0.029 g of racemic Example 21 (54% yield) as a single isomer as a white solid. HPLC: 98% at 2.97 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 405.05 [M−H]⁻.

Example 22

4-((1S,2R,6R,7R)-2-methyl-3,3-dioxido-3-thia-4-azatricyclo[5.2.1.0$^{2,6}$]dec-8-en-4-yl)-2-(trifluoromethyl)benzonitrile

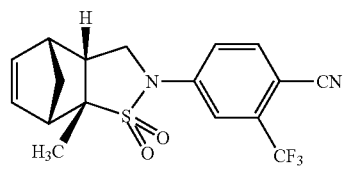

LiHMDS (3.67 mL of a 1M THF solution) was added to a colorless solution of Example 2 (1.0 g; 2.82 mmol) and MeI (0.5 mL; 8.47 mmol) in 28.0 mL dry THF at 0° C. under inert atmosphere to produce a pale yellow solution. After 10 min, the reaction was quenched with saturated aqueous $NH_4Cl$ and EtOAc and water was added. The layers were separated and the aqueous phase was extracted twice with 4 mL EtOAc. The organic layers were combined and washed once with brine, dried over $MgSO_4$, filtered, and concentrated in vacuo revealing the crude material in >95% purity by HPLC. The concentrate was purified on silica gel using 30% acetone/heptane and then dried in vacuo to give 0.980 g Example 22 (95% yield) as a white solid. HPLC: >99% at 3.291 min (YMC ODS-A column 4.6×50 mm eluting with 10-90% aqueous MeOH over 4 min containing 0.1% $H_3PO_4$, 4 mL/min, monitoring at 220 nm); and MS (ES): m/z 367 [M−H]⁻.

Example 23

4-((1R,2S,6S,7S)-2-methyl-3,3-dioxido-3-thia-4-azatricyclo[5.2.1.0$^{2,6}$]dec-8-en-4-yl)-2-(trifluoromethyl)benzonitrile

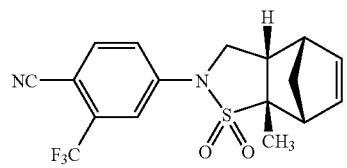

Example 23 was prepared from Example 3 in accordance with the general procedures utilized in preparing Example 22. HPLC: 99% at 3.29 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 427.2 [M−H]⁻.

Example 24

4-((1R,2R,6R,7S)-2-methyl-3,3-dioxido-3-thia-4-azatricyclo[5.2.1.0$^{2,6}$]dec-4-yl)-2-(trifluoromethyl)benzonitrile

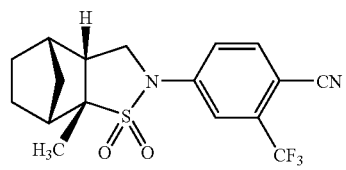

A solution-suspension of Example 22 (0.060 g; 0.16 mmol) and 10% Pd/C (0.012 g; 20 wt %) in EtOAc (3 mL) was stirred under 1 atmosphere of hydrogen at ambient temp for 2 hrs. The reaction mixture was filtered and washed with EtOAc. The resulting colorless filtrate was concentrated in vacuo to give 0.057 g Example 24 (93% yield) as a white solid. HPLC: 99% at 3.39 min (retention time) (YMC ODS-A column 4.6×50 mm eluting with 10-90% aqueous MeOH over 4 min containing 0.1% H3PO$_4$, 4 mL/min, monitoring at 220 nm); and MS (ES): m/z 429.2 [M−H]$^-$.

Example 25

4-((1R,2R,6R,7S)-2-ethyl-3,3-dioxido-3-thia-4-aza-tricyclo[5.2.1.0$^{2,6}$]dec-4-yl)-2-(trifluoromethyl)benzonitrile

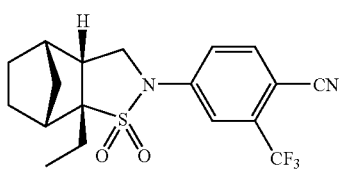

Example 25 was prepared from Example 4 and iodoethane in accordance with the general procedures utilized in preparing Example 22. HPLC: 99% at 3.55 min (retention time) (YMC ODS-A column 4.6×50 mm eluting with 10-90% aqueous MeOH over 4 min containing 0.1% H3PO$_4$, 4 mL/min, monitoring at 220 nm); and MS (ES): m/z 443.2[M−H]$^-$.

Example 26

4-((1R,2R,6R,7S)-2-allyl-3,3-dioxido-3-thia-4-aza-tricyclo[5.2.1.0$^{2,6}$]dec-4-yl)-2-(trifluoromethyl)benzonitrile

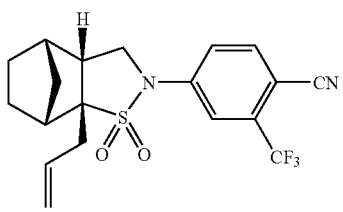

Example 26 was prepared from Example 4 and allyl iodide in accordance with the general procedures utilized in preparing Example 22. HPLC: 99% at 3.633 min (retention time) (YMC ODS-A column 4.6×50 mm eluting with 10-90% aqueous MeOH over 4 min containing 0.1% H3PO$_4$, 4 mL/min, monitoring at 220 nm); and MS (ES): m/z 455.2 [M−H]$^-$.

Example 27

4-((1R,2R,6R,7S)-2-ethyl-3,3-dioxido-3-thia-4-aza-tricyclo[5.2.1.0$^{2,6}$]dec-4-yl)-2-(trifluoromethyl)benzonitrile

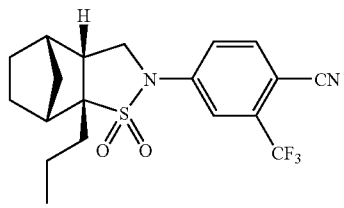

Example 27 was prepared from Example 26 in accordance with the general procedures utilized in preparing Example 4. HPLC: 98% at 3.75 min (retention time) (YMC ODS-A column 4.6×50 mm eluting with 10-90% aqueous MeOH over 4 min containing 0.1% H3PO$_4$, 4 mL/min, monitoring at 220 nm); and MS (ES): m/z 457.2[M−H]$^-$.

Example 28

4-((1S,2S,6S,7R)-2-ethyl-3,3-dioxido-3-thia-4-aza-tricyclo[5.2.1.0$^{2,6}$]dec-4-yl)-2-(trifluoromethyl)benzonitrile

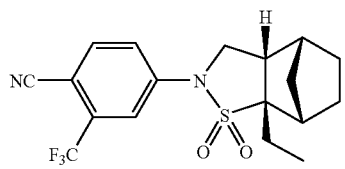

Example 28 was prepared from Example 5 and iodoethane in accordance with the general procedures utilized in preparing Example 22. HPLC: 99% at 3.54 min (retention time) (YMC ODS-A column 4.6×50 mm eluting with 10-90% aqueous MeOH over 4 min containing 0.1% H3PO$_4$, 4 mL/min, monitoring at 220 nm); and MS (ES): m/z 443.2 [M−H]$^-$.

Example 29

4-((1S,2S,6S,7R)-2-allyl-3,3-dioxido-3-thia-4-azatricyclo[5.2.1.0$^{2,6}$]dec-4-yl)-2-(trifluoromethyl)benzonitrile

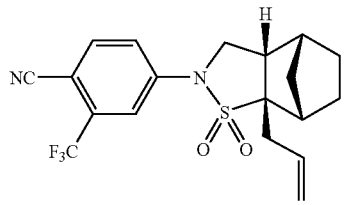

Example 29 was prepared from Example 5 and allyliodide in accordance with the general procedures utilized in preparing Example 22. HPLC: 98% at 3.63 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 455.2 [M−H]$^-$.

Example 30

4-((1S,2R,6R,7R)-2-((benzyloxy)methyl)-3,3-di-oxido-3-thia-4-azatricyclo[5.2.1.0²,⁶]dec-8-en-4-yl)-2-(trifluoromethyl)benzonitrile

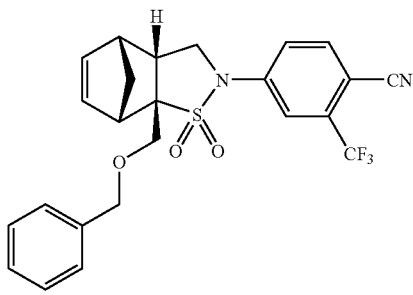

LiHMDS (1M/THF; 0.280 mL; 0.280 mmol) was added slowly via syringe to a solution of Example 2 (50 mg; 0.14 mmol) and chloromethyl benzyl ether (0.049 mL; 0.35 mmol) in 1.4 mL dry THF at 0° C. under $N_2$ atmosphere to give a pale yellow solution. After 20 min, the reaction was quenched with saturated $NH_4Cl$ and the ice bath removed. Next, 5 mL EtOAc and 3 mL water were added. The layers were separated and the aqueous layer was extracted three times with 5 mL EtOAc. The combined organic layers were washed with saturated $NaHCO_3$ and brine, dried over $MgSO_4$, filtrated, and concentrated to give 170 mg of a pale yellow oil, which was purified in two batches by preparative HPLC to give Example 30 in a quantitative yield (Mass recovery>100% due to 30% impurity). HPLC: 70% at 3.790 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 533.11 [M−H]⁻.

Example 31

4-((1R,2R,6R,7S)-2-((benzyloxy)methyl)-3,3-di-oxido-3-thia-4-azatricyclo[5.2.1.0²,⁶]dec-4-yl)-2-(trifluoromethyl)benzonitrile

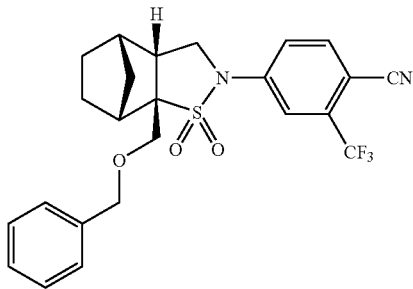

Example 31 was prepared from Example 30 in accordance with the general procedures utilized in preparing Example 24. HPLC: 99% at 3.838 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 535.2 [M−H]⁻.

Example 32

4-((1R,2R,6R,7S)-2-(hydroxymethyl)-3,3-dioxido-3-thia-4-azatricyclo[5.2.1.0²,⁶]dec-4-yl)-2-(trifluoromethyl)benzonitrile

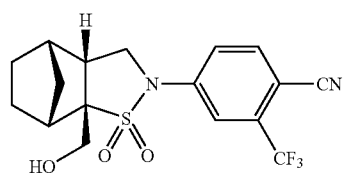

A solution-suspension of Example 30 (50 mg, 0.11 mmol) and Degussa-type Pd/C (10 mg; 20 wt %) in 4 mL EtOAc/MeOH (2:1) was stirred under 1 atmosphere of hydrogen at ambient temp for 5 hrs. The reaction vessel was then purged with $N_2$ to give a black suspension that was then filtered. The resulting colorless filtrate was concentrated in vacuo to give 35 mg of a mixture of starting material and product in a 2:1 ratio. The mixture was dissolved in $CH_2Cl_2$, loaded onto a preparative TLC plate, and eluted with 30% acetone/heptane to afford 15 mg Example 32 (36% yield) as a colorless film. HPLC: 98% at 3.015 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 445.11 [M−H+ OAc]⁻.

Example 33

4-((1S,2R,6R,7R)-2-(methoxymethyl)-3,3-dioxido-3-thia-4-azatricyclo[5.2.1.0²,⁶]dec-8-en-4-yl)-2-(trifluoromethyl)benzonitrile

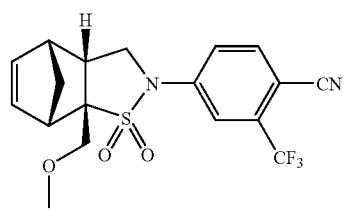

Example 33 was prepared from Example 2 and chloromethyl methyl ether in accordance with the general procedures utilized in preparing Example 30. HPLC: 93% at 3.24 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 457.1 [M−H]⁻.

Example 34

4-((1R,2R,6R,7S)-2-(methoxymethyl)-3,3-dioxido-3-thia-4-azatricyclo[5.2.1.0²,⁶]dec-4-yl)-2-(trifluoromethyl)benzonitrile

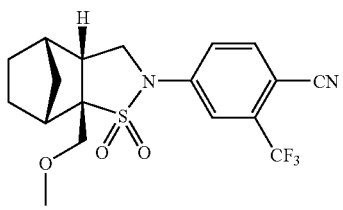

Example 34 was prepared from Example 33 in accordance with the general procedures utilized in preparing Example 24. HPLC: 99% at 3.295 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 459.1 [M−H]⁻.

Example 35

4-((1S,2S,6R,7R,9S)-9-hydroxy-2-(methoxymethyl)-3,3-dioxido-3-thia-4-azatricyclo[5.2.1.0²,⁶]dec-4-yl)-2-(trifluoromethyl)benzonitrile

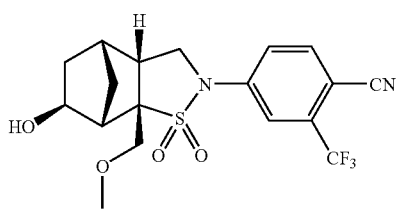

35A 4-((1S,2R,6R,7S,8R)-8-hydroxy-2-(methoxymethyl)-3,3-dioxido-3-thia-4-azatricyclo[5.2.1.0²,⁶]dec-4-yl)-2-(trifluoromethyl)benzonitrile

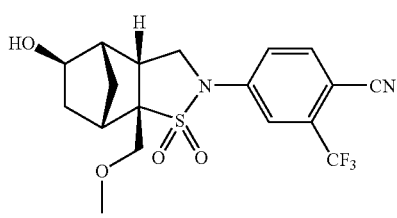

35B 35A and 35B were prepared from Example 33 in accordance with the general procedures utilized in preparing Example 6.

35A: HPLC: 99% at 2.57 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 475.1 [M−H]⁻.

35B: HPLC: 97% at 2.68 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 475.1 [M−H]⁻.

Example 36

Ethyl rac-(1R,2S,6S,7S)-4-(4-cyano-3-(trifluoromethyl)phenyl)-3-thia-4-azatricyclo[5.2.1.0²,⁶]dec-8-ene-2-carboxylate 3,3-dioxide

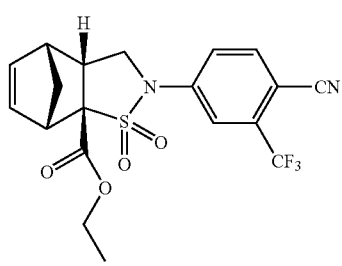

Example 36 (racemic) was prepared from Example 1K and ethyl chloroformate in accordance with the general procedures utilized in preparing Example 30. HPLC: 93% at 3.476 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 485.1 [M−H+OAc]⁻.

Example 37

4-((1S,2S,6R,7R,9S)-9-hydroxy-2-methyl-3,3-dioxido-3-thia-4-azatricyclo[5.2.1.0²,⁶]dec-4-yl)-2-(trifluoromethyl)benzonitrile

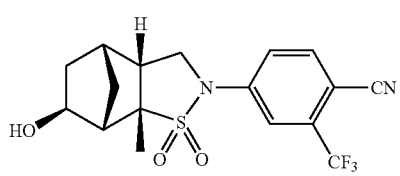

37A 4-((1S,2R,6R,7S,8R)-8-hydroxy-2-methyl-3,3-dioxido-3-thia-4-azatricyclo[5.2.1.0²,⁶]dec-4-yl)-2-(trifluoromethyl)benzonitrile (39i)

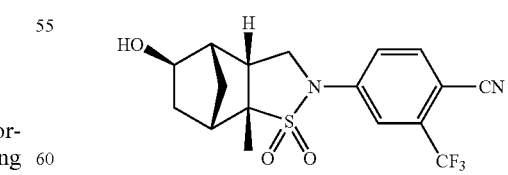

37B 37A and 37B were prepared from Example 22 in accordance with the general procedures utilized in preparing Example 6.

37A: HPLC: 97% at 2.65 min (retention time) (YMC ODS-A column 4.6×50 mm eluting with 10-90% aqueous MeOH over 4 min containing 0.1% H₃PO₄, 4 mL/min, monitoring at 220 nm). MS (ES): m/z 445.1 [M–H]⁻.

37B: HPLC: 99% at 2.80 min (retention time) (YMC ODS-A column 4.6×50 mm eluting with 10-90% aqueous MeOH over 4 min containing 0.1% H₃PO₄, 4 mL/min, monitoring at 220 nm). MS (ES): m/z 445.1 [M–H]⁻.

Example 38

4-((1S,2S,6R,7R,9S)-9-fluoro-2-methyl-3,3-dioxido-3-thia-4-azatricyclo[5.2.1.0²,⁶]dec-4-yl)-2-(trifluoromethyl)benzonitrile

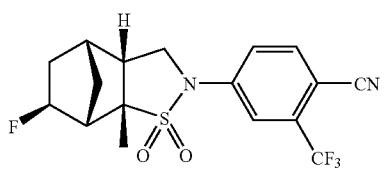

Example 38 was prepared from Example 37A in accordance with the general procedures utilized in preparing Example 17. HPLC: 99% at 3.30 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 447.18 [M–H]⁻.

Example 39

4-((1R,2R,6S,7S,9R)-9-fluoro-2-methyl-3,3-dioxido-3-thia-4-azatricyclo[5.2.1.0²,⁶]dec-4-yl)-2-(trifluoromethyl)benzonitrile

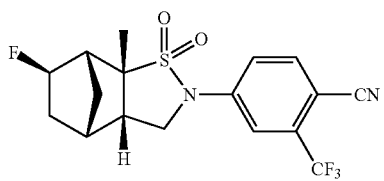

Example 39 was prepared from Example 18 in accordance with the general procedures utilized in preparing Example 22. HPLC: 99% at 3.3 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 447.18 [M–H]⁻.

Example 40

Rac-4-((1R,2S,5S,6S,7S)-5-allyl-3,3-dioxido-3-thia-4-azatricyclo[5.2.1.0²,⁶]dec-8-en-4-yl)-2-(trifluoromethyl)benzonitrile

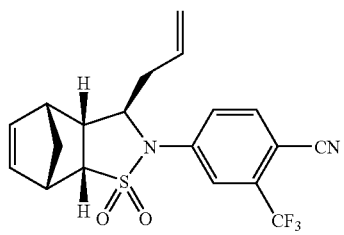

40A. Rac-4-((1S,2R,6R,7R)-5-hydroxy-3,3-dioxido-3-thia-4-azatricyclo[5.2.1.0²,⁶]dec-8-en-4-yl)-2-(trifluoromethyl)benzonitrile

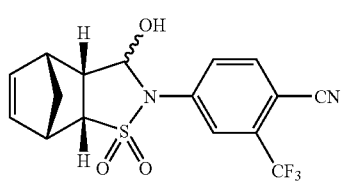

Diisobutylaluminum hydride solution (1M solution in PhMe; 5.43 mL; 2.0 equiv) was added to a colorless solution of 1E (1.0 g; 2.72 mmol) in dry THF at −78° C. under N₂ atmosphere to give a pale yellow solution. After 10 min at −78° C., the bath was removed and the reaction mixture was allowed to warm up to ambient temp. The reaction was quenched with 1 g sodium sulfate decahydrate, then 0.5 g celite and 25 mL EtOAc were added. The mixture was stirred vigorously for 20 min, filtered, and the filtrate concentrated to give 1 g 40A as a mixture of racemic diastereomers. HPLC: 84% at 2.895 min (retention time) (YMC ODS-A column 4.6×50 mm eluting with 10-90% aqueous MeOH over 4 min containing 0.1% H₃PO₄, 4 mL/min, monitoring at 220 nm).

40B. Rac-4-((1R,2S,5S,6S,7S)-5-allyl-3,3-dioxido-3-thia-4-azatricyclo[5.2.1.0²,⁶]dec-8-en-4-yl)-2-(trifluoromethyl)benzonitrile

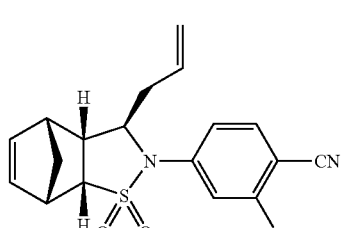

Boron trifluoride diethyl etherate (0.092 mL; 0.73 mmol) was added to a solution of allyl trimethylsilane (0.116 mL; 0.73 mmol) and 40A (0.090 g; 0.24 mmol) in dry CH₂Cl₂ at −78° C. under N₂ to give a yellow solution. After 20 min, the reaction mixture was quenched with saturated aqueous NH₄Cl solution. The organic layer was separated and the aqueous layer was extracted with CH$_2$Cl$_2$. The organic extracts were combined, dried over MgSO$_4$, filtered, and concentrated to give 0.1 g of an amber oil, which was purified by flash chromatography (10-40% EtOAc/hexane) affording 0.050 g of racemic 40B (as a single diastereomer) (53% yield). The colorless oil slowly crystallized into a solid. HPLC: 99% at 3.345 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 453.2 [M−H]$^-$.

Example 41

Rac-4-((1R,2R,5R,6R,7S)-3,3-dioxido-5-propyl-3-thia-4-azatricyclo[5.2.1.0$^{2,6}$]dec-4-yl)-2-(trifluoromethyl)benzonitrile

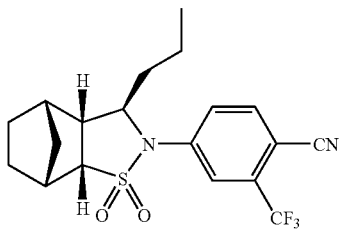

Racemic Example 41 was prepared from 40B in accordance with the general procedures utilized in preparing Example 4. HPLC: 99% at 3.57 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 457.2 [M−H]$^-$.

Example 42

Rac-4-((1R,2R,5R,6R,7S)-2-methyl-3,3-dioxido-5-propyl-3-thia-4-azatricyclo[5.2.1.0$^{2,6}$]dec-4-yl)-2-(trifluoromethyl)benzonitrile

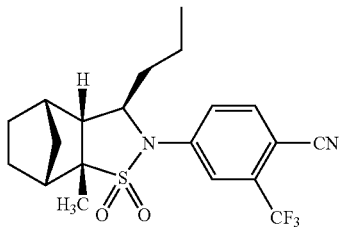

Racemic Example 42 was prepared from Example 41 in accordance with the general procedures utilized in preparing Example 22. HPLC: 99% at 3.573 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 457.2 [M−H]$^-$.

Example 43

Rac-4-((1R,2S,5S,6S,7S)-5-methyl-3,3-dioxido-3-thia-4-azatricyclo[5.2.1.0$^{2,6}$]dec-

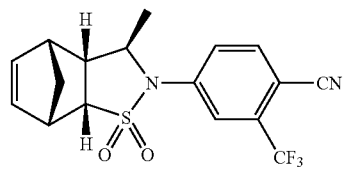

To a pale yellow solution of 40A (0.9 g; 2.43 mmol) in 25 mL dry CH$_2$Cl$_2$-78° C. under N$_2$ atmosphere were added successively a 2M solution of trimethylaluminum in PhMe (3.65 mL; 7.30 mmol) and boron trifluoride diethyl etherate (0.92 mL; 7.30 mmol). The reaction mixture was stirred for 10 min, and then slowly warmed to 0° C. Next, the reaction was quenched with solid sodium sulfate decahydrate, and then celite and CH$_2$Cl$_2$ were added. After stirring vigorously for 25 min, the suspension was filtered and the resulting cake was washed with CH$_2$Cl$_2$. The resulting yellow filtrate was concentrated in vacuo to give 1 g of an orange semisolid that was purified on silica gel using 5-30% acetone/hexane as eluent to give 0.402 g racemic Example 43 (45% yield) as a pale yellow solid. HPLC: 95% at 3.106 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 427.2 [M−H]$^-$.

Example 44

Rac-4-((1R,2R,5R,6R,7S)-5-methyl-3,3-dioxido-3-thia-4-azatricyclo[5.2.1.0$^{2,6}$]dec-4-yl)-2-(trifluoromethyl)benzonitrile

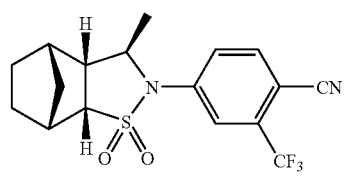

Example 44 was prepared as a racemate from Example 43 in accordance with the general procedures utilized in preparing Example 4. HPLC: 98% at 3.253 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 429.2 [M−H]$^-$.

Example 45

Rac-4-((1R,2R,5R,6R,7S)-2,5-dimethyl-3,3-dioxido-3-thia-4-azatricyclo[5.2.1.0$^{2,6}$]dec-4-yl)-2-(trifluoromethyl)benzonitrile

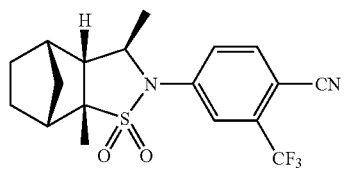

Example 45 was prepared as a racemate from Example 44 in accordance with the general procedures utilized in preparing Example 22. HPLC: 98% at 3.44 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 443.2 [M−H]$^-$.

Example 46

Rac-4-((1R,2R,5S,6S,7S,9R)-9-hydroxy-5-methyl-3,3-dioxido-3-thia-4-azatricyclo[5.2.1.0$^{2,6}$]dec-4-yl)-2-(trifluoromethyl)benzonitrile

46A

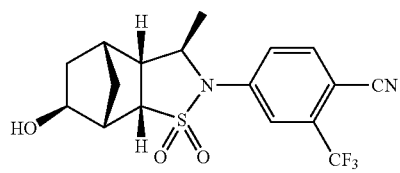

Rac-4-((1R,2S,5S,6S,7R,8S)-8-hydroxy-5-methyl-3,3-dioxido-3-thia-4-azatricyclo[5.2.1.0$^{2,6}$]dec-4-yl)-2-(trifluoromethyl)benzonitrile

46B

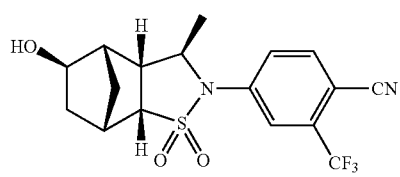

46A and 46B were prepared in racemic form from Example 43 in accordance with the general procedures utilized in preparing Example 6.

46A: HPLC: 96% at 2.70 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 445.1 [M−H]$^-$.

46B: HPLC: 96% at 2.79 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 445.1 [M−H]$^-$.

Example 47

4-((1S,2R,6R,7S)-3,3-dioxido-8-oxo-3-thia-4-azatricyclo[5.2.1.0$^{2,6}$]dec-4-yl)-2-(trifluoromethyl)benzonitrile

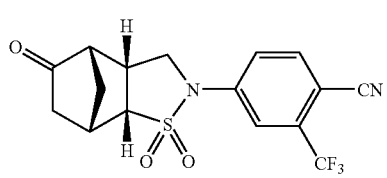

To a stirred solution of 6B (25 mg; 0.07 mmol) in 10 mL of THF/CH$_2$Cl$_2$ (1:1) under inert atmosphere at ambient temp was added Dess-Martin periodinane (89 mg; 0.21 mmol). The resulting white suspension was stirred overnight at 22° C. Next, the reaction was quenched with 2 mL of 1:1 10% Na$_2$SO$_3$/saturated NaHCO$_3$ solution and stirred vigorously until clear and biphasic. The layers were separated and the aqueous layer was extracted with CH$_2$Cl$_2$. The organic extracts were combined, dried over MgSO$_4$, filtered, and concentrated in vacuo to give 28 mg of a white film. The film was purified by preparative thin layer chromatography (20% EtOAc/hexane) to give 20 mg Example 47 (77% yield) as a white solid. HPLC: 98% at 2.67 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 429.3 [M−H]$^-$.

Example 48

4-((1S,2R,6R,7S,8S)-8-hydroxy-3,3-dioxido-8-phenyl-3-thia-4-azatricyclo[5.2.1.0$^{2,6}$]dec-4-yl)-2-(trifluoromethyl)benzonitrile

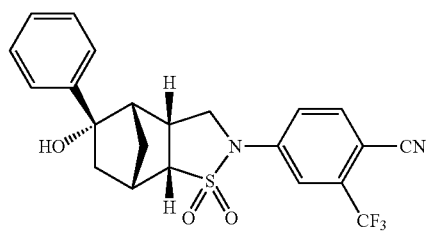

To a colorless solution of Example 47 (20 mg; 0.05 mmol) in 0.5 mL dry THF at 0° C. under inert atmosphere was added phenyl magnesium bromide (1M/THF; 0.070 mL; 0.07 mmol). The reaction was complete after warming to ambient temp. The reaction was then quenched with saturated NH$_4$Cl and EtOAc (2 mL). The organics were dried over MgSO$_4$, filtered thru celite rinsing with EtOAc; and concentrated in vacuo to give a colorless oil. The oil was immediately purified by prep TLC (20% EtOAc/CH$_2$Cl$_2$) to give 18 mg Example 48 (yield 82%) as a white solid. HPLC: 96% at 3.31 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 449.3 [M+H]$^+$.

Example 49

4-((1S,2R,6R,7S,8S)-8-hydroxy-3,3-dioxido-3-thia-4-azatricyclo[5.2.1.0²,⁶]dec-4-yl)-2-(trifluoromethyl)benzonitrile

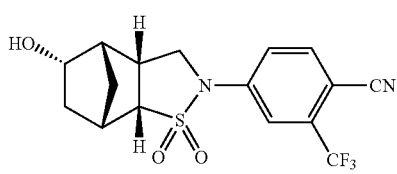

Example 49 was prepared from Example 47 in accordance with the general procedures utilized in preparing Example 12. HPLC: 99% at 2.65 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 373.2 [M+H]+.

Example 50

Rac-2-chloro-4-((1S,2R,6R,7R)-3,3-dioxido-3-thia-4-azatricyclo[5.2.1.0²,⁶]dec-8-en-4-yl)-3-methylbenzonitrile

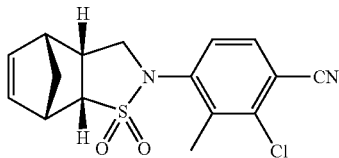
50D

Rac-2-chloro-4-((1S,2S,6S,7R)-3,3-dioxido-3-thia-4-azatricyclo[5.2.1.0²,⁶]dec-8-en-4-yl)-3-methylbenzonitrile

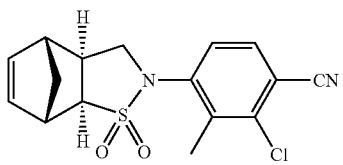
50E 50A. (E)-N-(3-chloro-4-cyano-2-methylphenyl)-2-phenylethenesulfonamide

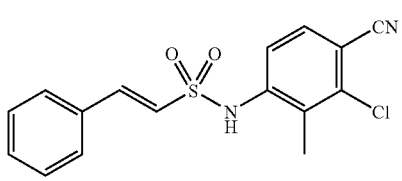
50A 50A was prepared according to the procedure disclosed in Harned A. M., et al, Org. Lett. 2003, 5, 15-1). Styrene sulfonyl chloride (6.08 g, 30 mmol) was reacted with 4-amino-2-chloro-3-methylbenzonitrile (5.00 g, 30 mmol) to give 7.32 g of crude 50A, which was used without further purification. HPLC retention time: 3.00 min (Chromolith SpeedROD column 4.6×50 mm eluting with 10-90% aqueous MeOH over 4 min containing 0.1% $H_3PO_4$, 4 mL/min, monitoring at 220 nm); and MS (ES): m/z 333 [M+H]+.

50B. (E)-N-(3-chloro-4-cyano-2-methylphenyl)-2-phenyl-N-2-propen-1-ylethenesulfonamide

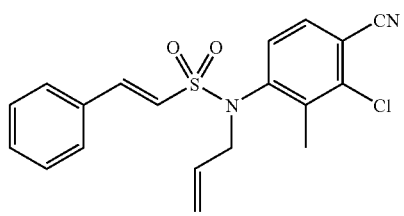
50B

Following the procedure described in the reference given above, 50A (6.86 g, 20.6 mmol) was treated with $K_2CO_3$ (5.79 g, 41.9 mmol), NaI (1.03 g, 6.87 mmol.), and allyl bromide (6.68 mL, 77.2 mmol.) in 60 mL $CH_3CN$ to give 7.32 g of crude 50B, which was used without further purification. HPLC retention time 3.33 min (Chromolith SpeedROD column 4.6×50 mm eluting with 10-90% aqueous MeOH over 4 min containing 0.1% $H_3PO_4$, 4 mL/min, monitoring at 220 nm); and MS (ES): m/z 373 [M+H]+.

50C. 2-chloro-4-(1,1-dioxido-2(3H)-isothiazolyl)-3-methylbenzonitrile

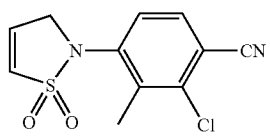
50C

To a solution of 50B (1.00 g, 2.68 mmol) in $CH_2Cl_2$ (5 mL) under $N_2$ was added 0.12 g (0.14 mmol) of [1,3-bis-(2,4,6-trimethylphenyl)-2-imidazolidinylidene)dichloro(phenylmethylene)-(tricyclohexylphosphine)ruthenium] (second generation Grubbs catalyst, Aldrich catalog number 56,974-7). The reaction mixture was heated at 45° C. for 14 hrs, allowed to cool to RT and filtered through a short silica gel pad to give 480 mg 50C, which was used without further purification. HPLC retention time 2.02 min (Chromolith SpeedROD column 4.6×50 mm eluting with 10-90% aqueous MeOH over 4 min containing 0.1% $H_3PO_4$, 4 mL/min, monitoring at 220 nm); and MS (ES): m/z 301 (M+H+ MeOH).

50D and 50E. Rac-2-chloro-4-((1S,2R,6R,7R)-3,3-dioxido-3-thia-4-azatricyclo[5.2.1.0$^{2,6}$]dec-8-en-4-yl)-3-methylbenzonitrile

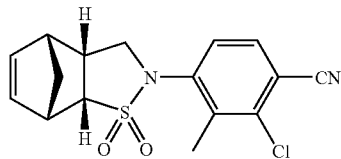

50D

Rac-2-chloro-4-((1S,2S,6S,7R)-3,3-dioxido-3-thia-4-azatricyclo[5.2.1.0$^{2,6}$]dec-8-en-4-yl)-3-methylbenzonitrile

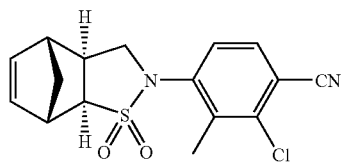

50E

To a stirred mixture of 50C (1.57 g, 5.84 mmol) and cyclopentadiene (1.02 mL, 17.9 mmol) in dry PhMe (20 mL) under N$_2$ at −78° C. was added dropwise a 1.8 M solution of diethylaluminum chloride in PhMe (3.40 mL, 6.12 mmol) over 10 min. The cooling bath was removed; the reaction mixture was stirred at RT for 1 hr, and then heated at 55° C. for 15 hrs. The mixture was allowed to cool to RT and poured into a mixture of cold (0° C.) aq. saturated NaHCO$_3$ (150 mL) solution and EtOAc (180 mL). The aqueous layer was separated and extracted with EtOAc (220 mL). The combined EtOAc extracts were washed with brine (60 mL), dried over MgSO$_4$, filtered, and concentrated in vacuo to give 2.05 g of crude product, which was purified by the ISCO Companion Auto Flash Chromatography using a 120 g column; Flow rate: 85 mL/min, solvent A: Hexanes, solvent B: CH$_2$Cl$_2$. Gradient: 50% B to 100% B elution to give 1.66 g racemic 50D (85% yield) and 62.4 mg racemic 50E (3.2% yield).

50D: HPLC: 97% at 2.82 min (retention time): (Chromolith SpeedROD column 4.6×50 mm eluting with 10-90% aqueous MeOH over 4 min containing 0.1% H$_3$PO$_4$, 4 mL/min, monitoring at 220 nm); and LC/MS: M+H=335.

50E: HPLC: 97% at 2.89 min (retention time): (Chromolith SpeedROD column 4.6×50 mm eluting with 10-90% aqueous MeOH over 4 min containing 0.1% H$_3$PO$_4$, 4 mL/min, monitoring at 220 nm); and LC/MS: M+H=335.

Example 51

Rac-2-chloro-4-((2'S,6'S)-3,'3'-dioxido-3'-thia-4'-azaspiro[cyclopropane-1,10'-tricyclo[5.2.1.0$^{2,6}$]decane]-8'-en-4'-yl)-3-methylbenzonitrile

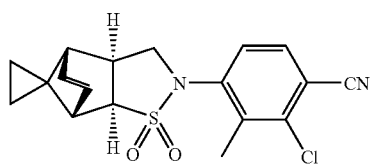

Example 53 was prepared as a racemate from 50C and spiro-[2.4]-hepta-4,6-diene in accordance with the general procedures utilized in preparing Example 50. HPLC: 100% at 3.03 min (retention time) (Chromolith SpeedROD column 4.6×50 mm eluting with 10-90% aqueous MeOH over 4 min containing 0.1% H$_3$PO$_4$, 4 mL/min, monitoring at 220 nm); and LC/MS: M+H=361.

Example 52

Rac-2-chloro-4-((1R,2S,6R,7R,10R)-3,3-dioxido-10-(trimethylsilyl)-3-thia-4-azatricyclo[5.2.1.0$^{2,6}$]dec-8-en-4-yl)-3-methylbenzonitrile

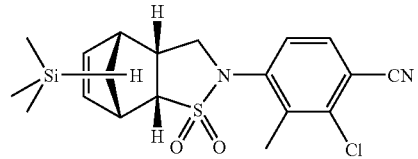

Example 54 was prepared as a racemate from 50C and 5-(trimethylsilyl)-1,3-cyclopentadiene in accordance with the general procedures utilized in preparing Example 50. HPLC: 100% at 3.70 min (retention time) (Chromolith SpeedROD column 4.6×50 mm eluting with 10-90% aqueous MeOH over 4 min containing 0.1% H$_3$PO$_4$, 4 mL/min, monitoring at 220 nm); and LC/MS: M+H=407.

Example 53

Rac-2-chloro-4-((2R,6R)-3,3-dioxido-3-thia-4-azatricyclo[5.2.2.0$^{2,6}$]undec-8-en-4-yl)-3-methylbenzonitrile

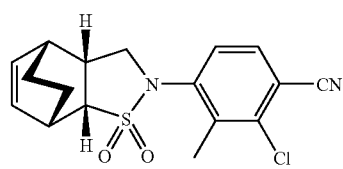

Example 53 was prepared as a racemate from 50C and 1,3-cyclohexadiene in accordance with the general procedures utilized in preparing Example 50. HPLC: 98% at 3.01 min (retention time) (Chromolith SpeedROD column 4.6×50 mm eluting with 10-90% aqueous MeOH over 4 min containing 0.1% H3PO$_4$, 4 mL/min, monitoring at 220 nm); and LC/MS: M+H=349.

Example 54

Rac-2-chloro-4-((1R,2S,6R,7R,9S)-9-hydroxy-3,3-dioxido-3-thia-4-azatricyclo[5.2.1.0$^{2,6}$]dec-4-yl)-3-methylbenzonitrile

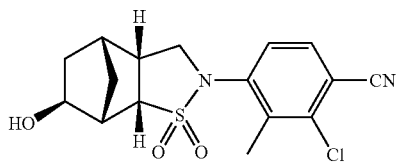

54A

Rac-2-chloro-4-((1R,2R,6R,7S,8R)-8-hydroxy-3,3-dioxido-3-thia-4-azatricyclo[5.2.1.0$^{2,6}$]dec-4-yl)-3-methylbenzonitrile

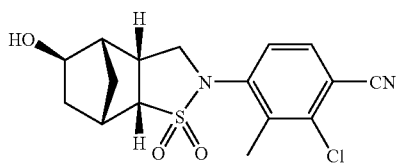

54B

Examples 54A and 54B were prepared in racemic form from 50D in accordance with the general procedures utilized in preparing Example 6 to yield 42% 54A and 43% 54B.

54A: HPLC: 100% at 2.15 min (retention time) (Chromolith SpeedROD column 4.6×50 mm eluting with 10-90% aqueous MeOH over 4 min containing 0.1% H3PO$_4$, 4 mL/min, monitoring at 220 nm); and LC/MS: M+H=353.

54B: HPLC: 98% at 2.12 min (retention time) (Chromolith SpeedROD column 4.6×50 mm eluting with 10-90% aqueous MeOH over 4 min containing 0.1% H$_3$PO$_4$, 4 mL/min, monitoring at 220 nm); and LC/MS: M+H=353.

Example 55

Rac-2-chloro-4-((1R,2S,6R,7S,8S,10R)-3,3-dioxido-9-oxa-3-thia-4-azatetracyclo[5.3.1.0$^{2,6}$.0$^{8,10}$]undec-4-yl)-3-methylbenzonitrile

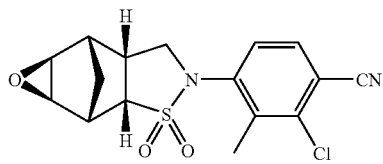

Example 55 was prepared as a racemate from Example 50D in accordance with the general procedures utilized in preparing Example 15 to yield 91% Example 55. HPLC: 100% at 2.43 min (retention time) (Chromolith SpeedROD column 4.6×50 mm eluting with 10-90% aqueous MeOH over 4 min containing 0.1% H$_3$PO$_4$, 4 mL/min, monitoring at 220 nm); and LC/MS: M+H=351.

Example 56

Rac-2-chloro-4-((1R,2R,6R,7S)-3,3-dioxido-3-thia-4-azatricyclo[5.2.1.0$^{2,6}$]dec-4-yl)-3-methylbenzonitrile

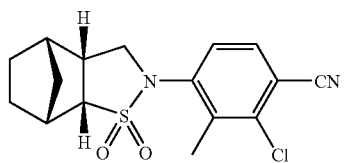

Example 56 was prepared as a racemate from 50D in accordance with the general procedures utilized in preparing Example 4 to yield 91% Example 56. HPLC retention time 3.00 min (Chromolith SpeedROD column 4.6×50 mm eluting with 10-90% aqueous MeOH over 4 min containing 0.1% H$_3$PO$_4$, 4 mL/min, monitoring at 220 nm); and MS (ES): m/z 337 [M+H]$^+$.

Example 57

4-((1S,2S,6R,7S,8S,10R)-2-((benzyloxy)methyl)-3,3-dioxido-9-oxa-3-thia-4-azatetracyclo[5.3.1.0$^{2,6}$.0$^{8,10}$]undec-4-yl)-2-(trifluoromethyl)benzonitrile

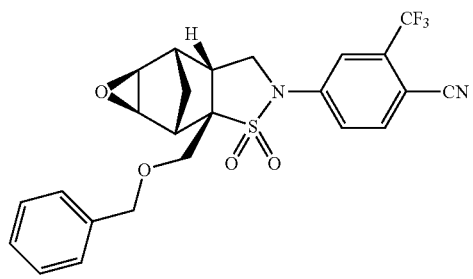

Example 57 was synthesized from Example 30 in accordance with the general procedures utilized in preparing Example 15 (i.e., Example 30 instead of 1K was used as the starting material). HPLC: 99% at 3.633 min (retention time) (YMC ODS-A column 4.6×50 mm eluting with 10-90% aqueous MeOH over 4 min containing 0.1% H3PO$_4$, 4 mL/min, monitoring at 220 nm); and MS (ES): m/z 549.1 [M−H+ OAc]$^−$.

Example 58

4-((1S,2S,6R,7S,8S,10R)-2-(hydroxymethyl)-3,3-dioxido-9-oxa-3-thia-4-azatetracyclo[5.3.1.0$^{2,6}$.0$^{8,10}$]undec-4-yl)-2-(trifluoromethyl)benzonitrile

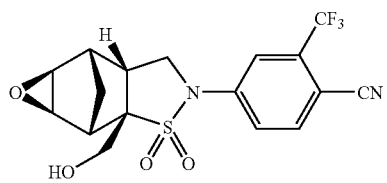

Example 58 was prepared from Example 57 in accordance with the general procedures utilized in preparing Example 32. HPLC: 99% at 2.600 min (retention time) (YMC ODS-A column 4.6×50 mm eluting with 10-90% aqueous MeOH over 4 min containing 0.1% H3PO4, 4 mL/min, monitoring at 220 nm); and MS (ES): m/z 459.19 [M−H+ OAc]−.

Example 59

4-((1S,2S,6R,7R,9S)-9-hydroxy-3,3-dioxido-2-((((phenylmethyl)oxy)methyl)-3-thia-4-azatricyclo[5.2.1.0261]dec-4-yl)-2-(trifluoromethyl)benzonitrile

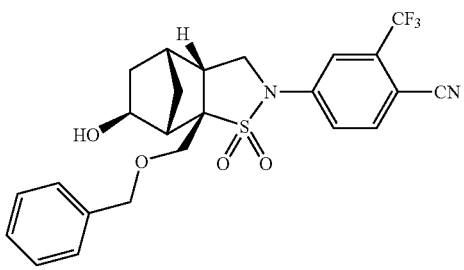

Example 59 was prepared from Example 30 in accordance with the general procedures utilized in preparing 6A. HPLC: 98% at 3.298 min (retention time), (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 551.28 [M−H+ OAc]−.

Example 60

4-((1S,2S,6R,7R,9S)-9-hydroxy-2-(hydroxymethyl)-3,3-dioxido-3-thia-4-azatricyclo[5.2.1.0$^{2,6}$]dec-4-yl)-2-(trifluoromethyl)benzonitrile

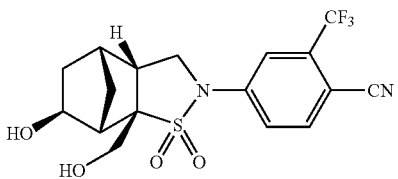

Hydrogen at 40 psi was introduced to a suspension of Example 59 (25 mg; 0.05 mmol) and 10% Pd/C (Degussa-Type; 10 mg 40 wt %) in 0.5 mL EtOAc in a sealed tube. The reaction mixture was stirred vigorously overnight, and subsequently filtrated and concentrated in vacuo to give 15 mg Example 60 (75% yield as a colorless film. HPLC: 95% at 2.287 min (retention time), (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 461.39 [M−H+ OAc]−.

Example 61

((1R,2R,6R,7S)-4-(4-cyano-3-(trifluoromethyl)phenyl)-3,3-dioxido-3-thia-4-azatricyclo[5.2.1.0$^{2,6}$]dec-2-yl)methyl trifluoromethanesulfonate

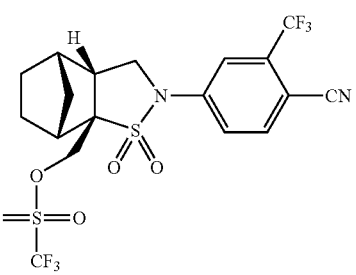

Triflic anhydride (0.350 mL; 1.5 mmol) was added via syringe to a colorless solution of Example 32 (542 mg; 1.4 mmol) and pyridine (0.230 mL; 2.8 mmol) in 14.0 mL dry CH$_2$Cl$_2$ at 0° C. under inert atmosphere. After 5 min, the resulting clear amber solution was quenched with 10 mL water and 3 mL 0.5 N HCl solution and 50 mL EtOAc added. The aqueous phase was extracted 3× with 10 mL EtOAc. The crimson organic extracts were combined, washed with saturated NaHCO$_3$ and brine, dried over MgSO$_4$, filtrated, and then concentrated in vacuo to give 525 mg Example 61 (~100% yield) as a brown foam in 92% purity by analytical HPLC. (Material was used successfully without purification, and is stable for several weeks under an inert atmosphere.) HPLC: 90% at 3.666 min (retention time), (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 519.18 [M+H]+.

Example 62

4-((1R,2R,6R,7S)-2-(((4-fluorophenyl)sulfanyl)methyl)-3,3-dioxido-3-thia-4-azatricyclo[5.2.1.0$^{2,6}$]dec-4-yl)-2-(trifluoromethyl)benzonitrile

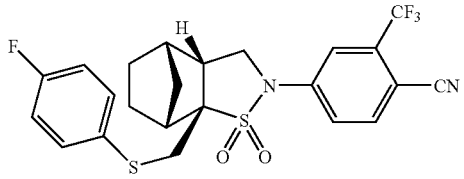

To a suspension of NaH (6.0 mg of a 60 wt % dispersion in mineral oil; 0.10 mmol) in 1 mL dry DMF at 0° C. under inert atmosphere was added 4-fluorobenzenthiol (0.012 mL; 0.11 mmol), resulting in gas evolution. After 5 min, a solution of Example 61 (50 mg; 0.1 mmol) in 1 mL of DMF was added via syringe, giving a clear amber solution. Reaction was complete after 5 min and was then quenched with saturated NH$_4$Cl, and 1 mL water and 3 mL EtOAc were added. The aqueous layer was then extracted 3× with 4 mL EtOAc. The organics were combined, washed with water and brine several times (to remove DMF), dried over MgSO$_4$, filtered, and then concentrated in vacuo revealing a yellow oil that was purified by silica gel chromatography (30% EtOAc/hexanes) to give 30 mg Example 62 (61% yield) as a colorless oil in 95% purity. HPLC: 95% at 3.881 min (retention time), (YMC ODS-A column 4.6×50 mm eluting with 10-90% aqueous MeOH over 4 min containing 0.1% H₃PO₄, 4 mL/min, monitoring at 220 nm); and MS (ES): m/z 555.19 [M−H+ OAc]⁻.

Example 63

4-((1R,2R,6R,7S)-2-(((4-fluorophenyl)sulfonyl)methyl)-3,3-dioxido-3-thia-4-azatricyclo[5.2.1.0²,⁶]dec-4-yl)-2-(trifluoromethyl)benzonitrile

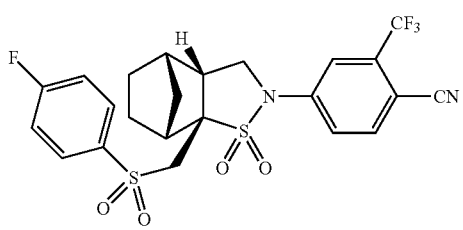

To a solution of Example 62 (30 mg; 0.06 mmol) in 2 mL of dry CH₂Cl₂ at ambient temp was added CPBA (40 mg; 0.18 mmol). The resulting clear colorless solution was stirred overnight under inert atmosphere. The reaction was then quenched with 3-hydroxypyridine (11.4 mg; 0.12 mmol) and stirred for 20 min. 2 mL saturated NaHCO₃ was then added and the reaction stirred an additional 20 min. The layers were separated and the aqueous phase extracted 2× with 3 mL methylene chloride. The colorless organics were combined, dried over MgSO₄, filtered, and concentrated in vacuo affording a colorless oil that was then purified by preparatory HPLC to give 24 mg Example 63 (80% yield) as a colorless oil. HPLC: 99% at 3.228 min (retention time), (YMC ODS-A column 4.6×50 mm eluting with 10-90% aqueous MeOH over 4 min containing 0.1% H₃PO₄, 4 mL/min, monitoring at 220 nm); and MS (ES): m/z 546.19 [M+H₂O].

Example 64

4-((1R,2R,6R,7S)-2-(cyanomethyl)-3,3-dioxido-3-thia-4-azatricyclo[5.2.1.0²,⁶]dec-4-yl)-2-(trifluoromethyl)benzonitrile

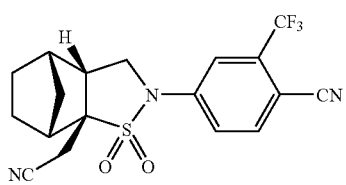

To a clear, brown solution of Example 63 (50 mg; 0.10 mmol) in 1.0 mL dry DMF at ambient temp under N₂ atmosphere was added KCN (13 mg; 0.20 mmol). The reaction was heated to 40° C. for 30 min and then quenched with 2 mL water and diluted with 5 mL EtOAc. The layers were separated and the aqueous phase extracted with 3 mL EtOAc. The organic extracts were combined, washed liberally with water and brine to remove DMF, dried over MgSO₄, filtered, and concentrated in vacuo affording a crude oil that was purified on silica gel (5% acetone/CH₂Cl₂) to give 23 mg Example 64 (58% yield) as a pale yellow oil. HPLC: 93% at 3.010 min (retention time), (YMC ODS-A column 4.6×50 mm eluting with 10-90% aqueous MeOH over 4 min containing 0.1% H3PO₄, 4 mL/min, monitoring at 220 nm); and MS (ES): m/z 454.31 [M−H+ OAc]⁻.

Example 65

4-((1R,2R,6R,7S)-2-(azidomethyl)-3,3-dioxido-3-thia-4-azatricyclo[5.2.1.0²,⁶]dec-4-yl)-2-(trifluoromethyl)benzonitrile

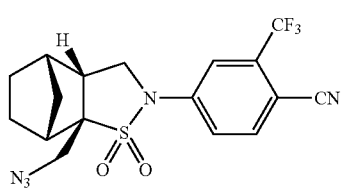

Example 65 was prepared in accordance with the general procedures utilized in preparing Example 64 by using sodium azide as the nucleophile. NOTE: Example 65 was prone to decomposition under ambient conditions. It is recommended that the material be used right away. HPLC: ~60% (impurity is residual DMF) at 3.010 min (retention time), (YMC ODS-A column 4.6×50 mm eluting with 10-90% aqueous MeOH over 4 min containing 0.1% H₃PO₄, 4 mL/min, monitoring at 220 nm); and MS (ES): m/z 470.28 [M−H+ OAc]⁻.

Example 66

4-((1R,2R,6R,7S)-2-(aminomethyl)-3,3-dioxido-3-thia-4-azatricyclo[5.2.1.0²,⁶]dec-4-yl)-2-(trifluoromethyl)benzonitrile

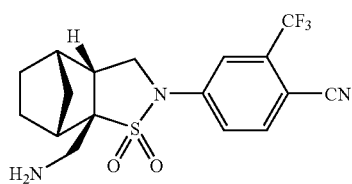

To a stirred amber solution of Example 65 (120 mg; 0.29 mmol) in 2.0 mL PhMe at RT under inert atmosphere was added PMe₃ (0.5M in THF; 2.3 mL; 1.17 mmol). After 1 hr, 1.5 mL 6 N HCl was added. The cloudy suspension was stirred for 30 min and then diluted with 5 mL water and 10 mL EtOAc. The mixture was washed 1× with NaHCO₃ and the layers separated. The aqueous phase was extracted 2× with 5 mL EtOAc. The organic extracts were combined, washed liberally with water and brine (to remove DMF), dried over MgSO₄, filtered, and concentrated in vacuo affording amber oil that was purified on silica gel (2% MeOH/CH₂Cl₂) to give 70 mg Example 66 (64% yield) as an off-white semi-solid. HPLC: 90% at 3.383 min (retention time), (YMC ODS-A column 4.6×50 mm eluting with 10-90% aqueous MeOH over 4 min containing 0.1% H3PO₄, 4 mL/min, monitoring at 220 nm); and MS (ES): m/z 386.28 [M+H]⁺.

Example 67

Methyl(((1R,2R,6R,7S)-4-(4-cyano-3-(trifluoromethyl)phenyl)-3,3-dioxido-3-thia-4-azatricyclo[5.2.1.0$^{2,6}$]dec-2-yl)methyl)carbamate

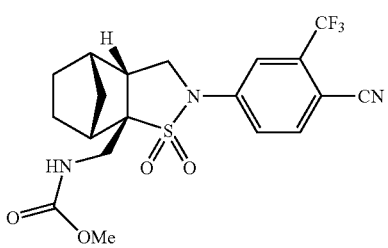

To a solution of Example 66 (100 mg; 0.26 mmol) in 2.5 mL of dry CH$_2$Cl$_2$ at ambient temp under inert gas was added DIPEA (0.091 mL; 0.52 mmol) and methyl chloroformate (0.026 mL; 0.34 mmol). After 5 min, 3 mL water and 10 mL EtOAc were added and the layers separated. The aqueous phase was extracted 2× with 5 mL EtOAc. The organic extracts were combined, dried over MgSO$_4$, filtered, and concentrated in vacuo to afford an amber oil that was purified on silica gel (1-2% acetone/CH$_2$Cl$_2$) to give 87 mg Example 67 (76% yield) as a white foam. HPLC: 99% at 3.268 min (retention time), (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 502.28 [M−H+ acetate]$^-$.

Examples 68 to 69

Examples 68 to 69, which are set forth in Table 1 hereinbelow, were prepared from Example 66 in accordance with the procedure utilized in preparing Example 67, wherein an appropriate amide and sulfonamide group were coupled thereto via standard amine-coupling techniques known in the field and/or as shown in Examples 67 and/or as otherwise described herein.

TABLE 1

| Example | Compound | Retention Time Min./Molecular Mass |
|---|---|---|
| 68 | ![structure] N-(((1R,2R,6R,7S)-4-(4-cyano-3-(trifluoromethyl)phenyl)-3,3-dioxido-3-thia-4-azatricyclo[5.2.1.0$^{2,6}$]dec-2-yl)methyl)ethanesulfonamide | 3.170 LCMS [M − H]$^-$ = 476.28 |
| 69 | ![structure] N-(((1R,2R,6R,7S)-4-(4-cyano-3-(trifluoromethyl)phenyl)-3,3-dioxido-3-thia-4-azatricyclo[5.2.1.0$^{2,6}$]dec-2-yl)methyl)-4-(methyloxy)benzamide | 3.620 LCMS [M + H]$^+$ = 520.35 |

Example 70

4-((1S,2R,6R,7R)-3,3-dioxido-2-(((phenylmethyl)oxy)methyl)-3-thia-4-azatricyclo[5.2.1.0$^{2,6}$]dec-8-en-4-yl)-2-(trifluoromethyl)benzonitrile

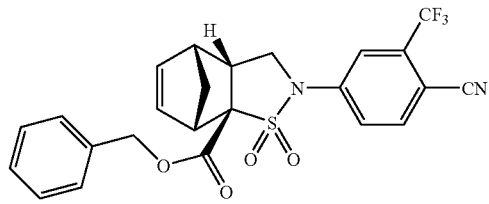

Example 70 was prepared from Example 2 in accordance with the general procedures utilized in preparing Example 30, wherein benzyl chloroformate was used as a reactant. HPLC: 99% at 3.793 min (retention time), (YMC ODS-A column 4.6×50 mm eluting with 10-90% aqueous MeOH over 4 min containing 0.1% H3PO$_4$, 4 mL/min, monitoring at 220 nm); and MS (ES): m/z 557.29 [M−H+ OAc]$^-$.

Example 71

Methyl (1S,2R,6R,7R)-4-(4-cyano-3-(trifluoromethyl)phenyl)-3-thia-4-azatricyclo[5.2.1.0$^{2,6}$]dec-8-ene-2-carboxylate 3,3-dioxide

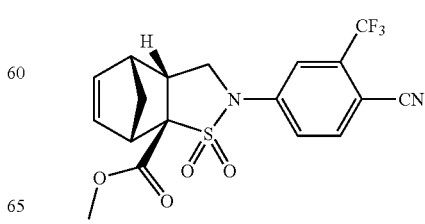

Example 71 was prepared from Example 2 in accordance with the general procedures utilized in preparing Example 30, wherein methyl chloroformate was used as a reactant. HPLC: 99% at 3.271 min (retention time), (YMC ODS-A column 4.6×50 mm eluting with 10-90% aqueous MeOH over 4 min containing 0.1% $H_3PO_4$, 4 mL/min, monitoring at 220 nm); and MS (ES): m/z 471.29 [M−H+ acetate]$^-$.

Example 72

(1R,2R,6R,7S)-4-(4-cyano-3-(trifluoromethyl)phenyl)-3-thia-4-azatricyclo[5.2.1.0$^{2,6}$]decane-2-carboxylic acid 3,3-dioxide

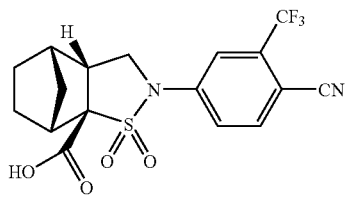

To a solution of Example 70 (1.8 g; 3.69 mmol) in 12 mL EtOAc was added 10% Pd/C, Degussa-type (360 mg; 20 wt %) in a sealed tube apparatus. A 40 psi hydrogen atmosphere was then introduced. The black suspension stirred vigorously at ambient temp for 5 hrs, filtrated, and then concentrated in vacuo to give 1.8 g of Example 72 (100% yield) as a white foam. No purification was necessary. HPLC: 99% at 3.206 min (retention time), (YMC ODS-A column 4.6×50 mm eluting with 10-90% aqueous MeOH over 4 min containing 0.1% $H_3PO_4$, 4 mL/min, monitoring at 220 nm); and MS (ES): compound would not ionize; only parent decarboxylation observed by positive or negative ESI technology.

Example 73

(1R,2R,6R,7S)-4-(4-cyano-3-(trifluoromethyl)phenyl)-3-thia-4-azatricyclo[5.2.1.0$^{2,6}$]decane-2-carbonyl chloride 3,3-dioxide

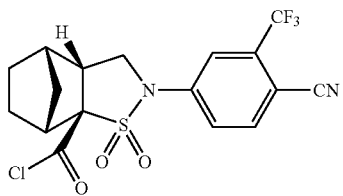

To a solution of Example 72 (915 mg; 2.3 mmol) and a drop of pyridine in 2 mL dry $CH_2Cl_2$ at ambient temp under inert gas was added neat oxalyl chloride (2.9 g; 23 mmol). The reaction was heated overnight at 40° C. and then $CH_2Cl_2$ (5 mL) was added. 2 mL PhMe was then added and the volatiles removed in vacuo to give a tan solid. 950 mg Example 73 (99% yield) was obtained in >95% purity by HPLC. HPLC: 98% at 3.596 min (retention time), (YMC ODS-A column 4.6×50 mm eluting with 10-90% aqueous MeOH over 4 min containing 0.1% $H_3PO_4$, 4 mL/min, monitoring at 220 nm); and MS (ES): no molecular ion observed.

Example 74

(1R,2R,6R,7S)-4-(4-cyano-3-(trifluoromethyl)phenyl)-3-thia-4-azatricyclo[5.2.1.0$^{2,6}$]decane-2-carboxamide 3,3-dioxide

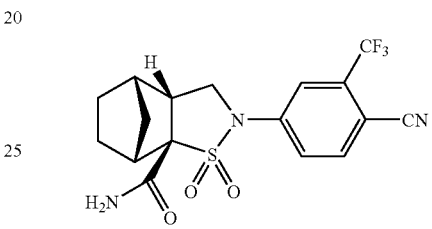

To an off-white solution of Example 73 (100 mg; 0.24 mmol) in 2.0 mL dry $CH_2Cl_2$ at ambient temp under inert gas was added DIPEA (0.084 mL; 0.48 mmol) and ammonia (0.5M in 1,4-dioxane; 1.44 mL; 0.72 mmol). The resulting clear brown reaction was complete within 10 min and the solvent removed using a stream of $N_2$. The remaining residue was purified by flash chromatography (1-5% acetone/$CH_2Cl_2$) to give 91 mg Example 74 (96% yield) as a white foam. HPLC: 99% at 2.890 min (retention time), (YMC ODS-A column 4.6×50 mm eluting with 10-90% aqueous MeOH over 4 min containing 0.1% $H_3PO_4$, 4 mL/min, monitoring at 220 nm); and MS (ES): m/z 397.19 [M−H]$^-$.

Examples 75 to 79

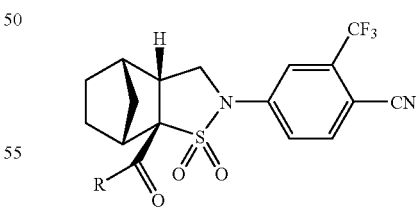

Compounds having the formulae above, wherein the group R has the values reported in Table 2, were prepared from Example 73 in accordance with the general procedures utilized in preparing Example 74, wherein an appropriate amine was coupled thereto via standard amine-coupling techniques known in the field and/or as shown in Example 74 and/or as otherwise described herein.

TABLE 2

| Example | R | Name | Retention Time Min/Molecular Mass |
|---|---|---|---|
| 75 | ![benzyl-NH] | (1R,2R,6R,7S)-N-benzyl-4-(4-cyano-3-(trifluoromethyl)phenyl)-3-thia-4-azatricyclo[5.2.1.0$^{2,6}$]decane-2-carboxamide 3,3-dioxide | 3.206 LCMS [M − H]$^-$ = 488.19 |
| 76 | ![4-methoxybenzyl-NH] | (1R,2R,6R,7S)-4-(4-cyano-3-(trifluoromethyl)phenyl)-N-(4-methoxybenzyl)-3-thia-4-azatricyclo[5.2.1.0$^{2,6}$]decane-2-carboxamide 3,3-dioxide | 3.413 LCMS [M + H]$^+$ = 518.28 |
| 77 | ![(S)-1-phenylethyl-NH] | (1R,2R,6R,7S)-4-(4-cyano-3-trifluoromethyl)phenyl)-N-((1S)-1-phenylethyl)-3-thia-4-azatricyclo[5.2.1.0$^{2,6}$]decane-2-carboxamide 3,3-dioxide | 3.523 LCMS [M − H]$^-$ = 502.29 |
| 78 | ![N-methyl] | (1R,2R,6R,7S)-4-(4-cyano-3-(trifluoromethyl)phenyl)-N-methyl-3-thia-4-azatricyclo[5.2.1.0$^{2,6}$]decane-2-carboxamide 3,3-dioxide | 2.961 LCMS [M − H + OAc]$^-$ = 472.28 |
| 79 | ![N,N-dimethyl] | (1R,2R,6R,7S)-4-(4-cyano-3-(trifluoromethyl)phenyl)-N,N-dimethyl-3-thia-4-azatricyclo[5.2.1.0$^{2,6}$]decane-2-carboxamide 3,3-dioxide | 3.301 LCMS [M − H + OAc]$^-$ = 486.26 |

Example 80

4-((1S,2S,6R,7S,8S,10R)-2-methyl-3,3-dioxido-9-oxa-3-thia-4-azatetracyclo[5.3.1.0$^{2,6}$.0$^{8,10}$]undec-4-yl)-2-(trifluoromethyl)benzonitrile

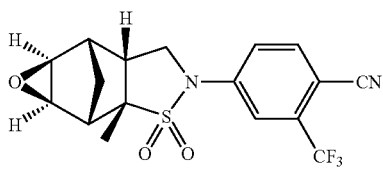

To a solution of Example 22 (0.30 g, 0.81 mmol) in CH$_2$Cl$_2$ (15 mL) at 22° C. was added mCPBA (~70% mixture, 0.36 g, 1.6 mmol). The reaction was stirred at 22° C. under N$_2$ for 15 hrs and then 3-hydroxyl pyridine (0.23 g, 2.4 mmol) was added. The reaction was stirred at 22° C. for 25 min and then it was diluted with EtOAc, washed with saturated NaHCO$_3$ (100 mL) and brine, dried over MgSO$_4$, filtered, concentrated in vacuo, and purified with flash chromatography by an ISCO system using an 80 g column, Flow rate: 60 mL/min, solvent A: CH$_2$Cl$_2$, solvent B: EtOAc. Gradient: 0% B to 20% B in 25 min to give 0.23 g Example 80 (74% yield) as a white solid. HPLC: 98% at 3.04 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 443.08 [M−H+ OAc]$^-$.

Example 81

4-((1S,2S,6R,7S,8S,9R)-8,9-dihydroxy-2-methyl-3,3-dioxido-3-thia-4-azatricyclo[5.2.1.0$^{2,6}$]dec-4-yl)-2-(trifluoromethyl)benzonitrile

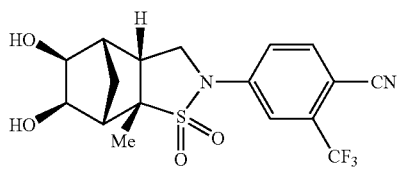

To a solution of Example 22 (0.050 g, 0.14 mmol) in acetone (0.5 mL) at 22° C. was added 4-methylmorpholine N-oxide (50% solution in water, 0.048 g, 0.20 mmol) followed by OsO$_4$ (0.034 mL, 0.0027 mmol). The reaction was stirred under N$_2$ at 22° C. for 15 hrs and then diluted with CH$_2$Cl$_2$ and water. The organic layer was separated and washed with brine, dried over MgSO$_4$, filtered, concentrated in vacuo, and purified with flash chromatography with an ISCO system using a 4 g column, Flow rate: 20 mL/min, solvent A: CH$_2$Cl$_2$, solvent B: EtOAc. Gradient: 0% B to 40% B in 25 min to give 0.030 g Example 81 (56% yield) as an off white solid. HPLC: 98% at 2.6 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 461.32 [M−H+ OAc]$^-$.

Example 82

4-((1S,2S,6R,7R)-2-methyl-3,3-dioxido-9-oxo-3-thia-4-azatricyclo[5.2.1.0²,⁶]dec-4-yl)-2-(trifluoromethyl)benzonitrile

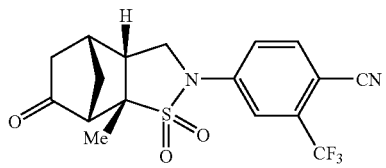

To a solution of 37A (1.00 g, 2.59 mmol) in CH$_2$Cl$_2$ (100 mL) at 22° C. was added Dess-Martin periodinane (1.65 g, 3.88 mmol). The reaction was stirred at 22° C. for 24 hrs and then saturated NaHCO$_3$ (50 mL) followed by 10% Na$_2$SO$_3$ (100 mL) were added. The reaction was stirred at 22° C. for 20 min, and then the organic layer was separated, washed with brine, dried over MgSO$_4$, filtered, and concentrated in vacuo to give 0.90 g Example 82 (90% yield) as an off-white solid. HPLC: 98% at 2.4 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 443.20 [M–H]⁻.

Example 83

4-((1S,2R,6R,7S)-2-methyl-3,3-dioxido-8-oxo-3-thia-4-azatricyclo[5.2.1.0²,⁶]dec-4-yl)-2-(trifluoromethyl)benzonitrile

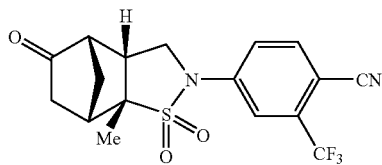

Example 83 was prepared from 37B in accordance with the general procedures utilized in preparing Example 82. HPLC: 98% at 2.78 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 443.20 [M–H]⁻.

Example 84

4-((1S,2S,6R,7R,9R)-9-hydroxy-2-methyl-3,3-dioxido-3-thia-4-azatricyclo[5.2.1.0²,⁶]dec-4-yl)-2-(trifluoromethyl)benzonitrile

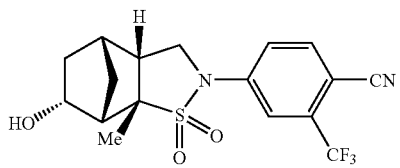

To a solution of Example 82 (0.90 g, 2.3 mmol) in MeOH and THF (5.0 mL, 5.0 mL) at 22° C. was added NaBH$_4$ (0.18 g, 4.7 mmol). The reaction was stirred at 22° C. under N$_2$ for 2 hrs and then diluted with EtOAc (100 mL). The organic layer was washed with saturated NH$_4$Cl, brine, dried over MgSO$_4$, filtered, and concentrated in vacuo to give 0.90 g Example 84 (98% yield) as a white solid. HPLC: 98% at 2.67 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 385.27 [M–H]⁻.

Example 85

4-((1S,2R,6R,7S,8S)-8-hydroxy-2-methyl-3,3-dioxido-3-thia-4-azatricyclo[5.2.1.0²,⁶]dec-4-yl)-2-(trifluoromethyl)benzonitrile

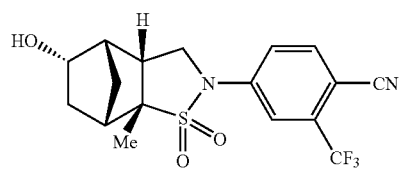

Example 85 was prepared from Example 83 in accordance with the general procedures utilized in preparing Example 84. HPLC: 98% at 2.81 min (retention times) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 445.30 [M–H+ OAc]⁻.

Example 86

(1S,2S,6R,7R,9R)-4-(4-cyano-3-(trifluoromethyl)phenyl)-2-methyl-3,3-dioxido-3-thia-4-azatricyclo[5.2.1.0²,⁶]dec-9-yl trifluoromethanesulfonate

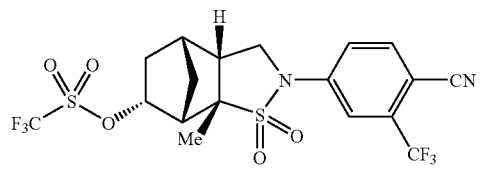

To a solution of Example 84 (0.904 g, 2.3 mmol) in CH$_2$Cl$_2$ (50 mL) at 0° C. was added pyridine (0.28 mL, 3.5 mmol) followed by trifluoromethylsulfonic anhydride (0.43 mL, 2.6 mmol). The reaction was stirred at 0° C. for 10 min then it was warmed to 22° C. and stirred under N$_2$ for 2 hrs. The reaction was diluted with CH$_2$Cl$_2$; washed with saturated NaHCO$_3$ (100 mL), 1N HCl (100 mL), and brine; dried over MgSO$_4$, filtered, concentrated in vacuo, and purified with flash chromatography by an ISCO system using an 80 g column, Flow rate: 60 mL/min, solvent A: CH$_2$Cl$_2$, solvent B: EtOAc. Gradient: 0% B to 50% B in 25 min to give 0.80 g Example 86 (67% yield) as a white solid. HPLC: 98% at 3.26 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 577.15 [M–H+ OAc]⁻.

Example 87

(1S,2R,6R,7S,8S)-4-(4-cyano-3-(trifluoromethyl)phenyl)-2-methyl-3,3-dioxido-3-thia-4-azatricyclo[5.2.1.0²,⁶]dec-8-yl trifluoromethanesulfonate

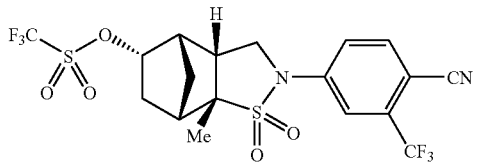

Example 87 was prepared from Example 85 in accordance with the general procedures utilized in preparing Example 86. HPLC: 98% at 3.40 min (retention times) (YMC ODS-A column 4.6×50 mm eluting with 10-90% aqueous MeOH over 4 min containing 0.1% $H_3PO_4$, 4 mL/min, monitoring at 220 nm); and MS (ES): m/z 577.17 [M–H+ OAc]⁻.

Example 88

(1S,2R,6R,7S,9S)-4-(4-cyano-3-(trifluoromethyl)phenyl)-2-methyl-3-thia-4-azatricyclo[5.2.1.0²,⁶]decane-9-carbonitrile 3,3-dioxide

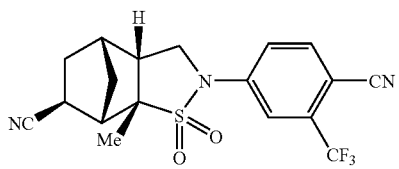

To a solution of Example 86 (0.025 g, 0.048 mmol) in PhMe (0.5 mL) at 22° C. was added nBu₄CN (0.065 g, 0.24 mmol). The reaction was stirred at 50° C. under $N_2$ for 16 hrs, concentrated in vacuo, and purified with preparative TLC, eluting with 40% EtOAc/$CH_2Cl_2$ to give 0.005 g Example 88 (26% yield) as a light yellow solid. HPLC: 98% at 3.00 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 454.31 [M–H+ OAc]⁻.

Example 89

(1S,2R,6R,7R,8R)-4-(4-cyano-3-(trifluoromethyl)phenyl)-2-methyl-3-thia-4-azatricyclo[5.2.1.0²,⁶]decane-8-carbonitrile 3,3-dioxide

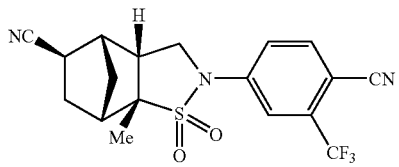

Example 89 was prepared from Example 87 in accordance with the general procedures utilized in preparing Example 88. HPLC: 98% at 3.00 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 454.31 [M–H+ OAc]⁻.

Example 90

4-((1S,2R,6R,7S,8R)-8-azido-2-methyl-3,3-dioxido-3-thia-4-azatricyclo[5.2.1.0²,⁶]dec-4-yl)-2-(trifluoromethyl)benzonitrile

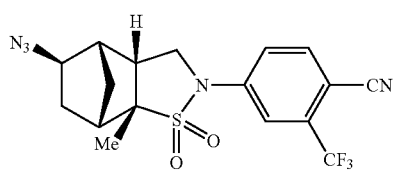

90A 4-((1S,2S,6R,7R,9S)-9-azido-2-methyl-3,3-dioxido-3-thia-4-azatricyclo[5.2.1.0²,⁶]dec-4-yl)-2-(trifluoromethyl)benzonitrile

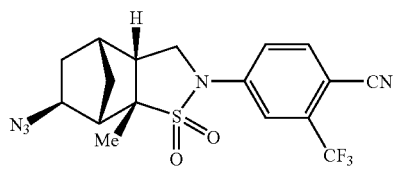

90B

To a solution of NaN₃ (0.57 g, 8.8 mmol) in THF/$H_2O$ (12 mL/6 mL) at 22° C. was added Hg(OAc)₂ (0.68, 2.1 mmol) followed by Example 22 (0.65 g, 1.8 mmol). The reaction was stirred at 22° C. for 2 hrs and then 15% KOH (3 mL) was slowly added followed by NaBH₄ (0.20 g, 5.3 mmol) in 15% KOH (3 mL). The reaction was stirred for 30 min and then diluted with EtOAc and water. The organic layer was separated, washed with brine, dried over MgSO₄, filtered, concentrated in vacuo, and purified with flash chromatography by an ISCO system using a 120 g column, Flow rate: 85 mL/min, solvent A: Heptane, solvent B: EtOAc. Gradient: 0% B to 100% B in 25 min to give 0.14 g 90A as a white solid and 0.36 g 90B as a white solid.

90A: HPLC: 98% at 3.5 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 470.32 [M–H+ OAc]⁻.

90B: HPLC: 99% at 3.5 min (retention time) (YMC ODS-A column 4.6×50 mm eluting with 10-90% aqueous MeOH over 4 min containing 0.1% $H_3PO_4$, 4 mL/min, monitoring at 220 nm); and MS (ES): m/z 470.32 [M–H+ OAc]⁻.

Example 91

4-((1S,2S,6R,7R,9S)-9-amino-2-methyl-3,3-dioxido-3-thia-4-azatricyclo[5.2.1.0²,⁶]dec-4-yl)-2-(trifluoromethyl)benzonitrile

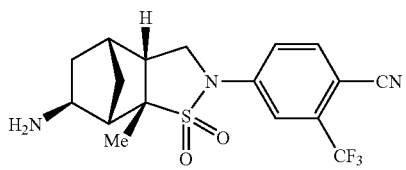

To a suspension of 90B (0.31 g, 0.75 mmol) in PhMe (10 mL) at 22° C. was added PMe₃ (1M solution in THF, 3.5 mL, 3.5 mmol). The resulting homogeneous reaction was stirred at 22° C. for 16 hrs, and then 6N HCl (4 mL) was added. The reaction was stirred for 30 min. and then diluted with EtOAc. The aqueous layer was separated and purified with Prep HPLC to give 0.19 g Example 91 (64% yield) as a white solid. HPLC: 99% at 2.0 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 386.33 [M+H]⁺.

Example 92

4-((1S,2R,6R,7S,8R)-8-amino-2-methyl-3,3-dioxido-3-thia-4-azatricyclo[5.2.1.0²,⁶]dec-4-yl)-2-(trifluoromethyl)benzonitrile

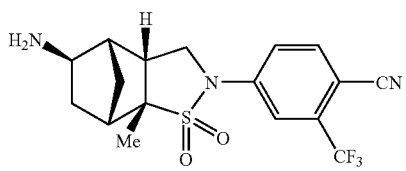

Example 92 was prepared from 90A in accordance with the general procedures utilized in preparing Example 91. HPLC: 99% at 2.12 min (retention time) (YMC ODS-A column 4.6×50 mm eluting with 10-90% aqueous MeOH over 4 min containing 0.1% H₃PO₄, 4 mL/min, monitoring at 220 nm); and MS (ES): m/z 386.33 [M+H]⁺.

Example 93

N-((1S,2R,6R,7S,8R)-4-(4-cyano-3-(trifluoromethyl)phenyl)-2-methyl-3,3-dioxido-3-thia-4-azatricyclo[5.2.1.0²,⁶]dec-8-yl)acetamide

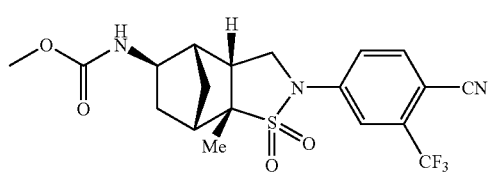

To a solution of Example 92 (0.010 g, 0.026 mmol) in CH₂Cl₂ (0.5 mL) at 22° C. was added Et₃N (0.007 mL, 0.052 mmol) followed by methyl chloroformate (0.004 mL, 0.052 mmol). The reaction was stirred at 22° C. for 20 min then it was purified with flash chromatography in ISCO using a 4 g column, eluting with 50% EtOAc to give 0.008 g Example 93 (70% yield) as a white solid. HPLC: 98% at 3.02 min (retention times) (YMC ODS-A column 4.6×50 mm eluting with 10-90% aqueous MeOH over 4 min containing 0.1% H₃PO₄, 4 mL/min, monitoring at 220 nm); and MS (ES): m/z 442.32 [M−H]⁻.

Examples 94 to 97

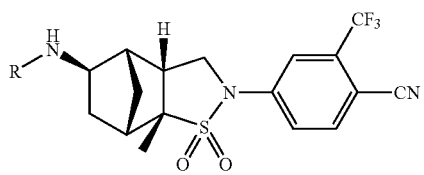

Compounds having the formulae above, wherein the group R has the values reported in Table 3, were prepared from Example 92 in accordance with the general procedures utilized in preparing Example 93, wherein an appropriate amide, alkanoyl, carboxamide, carboxylic acid, sulfonamide, substituted alkyl, etc. group was coupled thereto via standard amine-coupling techniques known in the field and/or as shown in Example 93 and/or as otherwise described herein.

TABLE 3

| Example | R | Name | Retention Time Min./Molecular Mass |
|---------|---|------|------------------------------------|
| 94 | —CO₂n-Propyl | Propyl ((1S,2R,6R,7S,8R)-4-(4-cyano-3-(trifluoromethyl)phenyl)-2-methyl-3,3-dioxido-3-thia-4-azatricyclo[5.2.1.0²,⁶]dec-8-yl)carbamate | 3.35 LCMS [M + H]⁺ = 472.33 |
| 95 | —COMe | N-((1S,2R,6R,7S,8R)-4-(4-cyano-3-(trifluoromethyl)phenyl)-2-methyl-3,3-dioxido-3-thia-4-azatricyclo[5.2.1.0²,⁶]dec-8-yl)acetamide | 2.84 LCMS [M − H + OAc]⁻ = 486.33 |
| 96 | CONHi-Propyl | 1-((1S,2R,6R,7S,8R)-4-(4-cyano-3-(trifluoromethyl)phenyl)-2-methyl-3,3-dioxido-3-thia-4-azatricyclo[5.2.1.0²,⁶]dec-8-yl)-3-isopropylurea | 3.15 LCMS [M + H]⁺ = 471.32 |

TABLE 3-continued

| Example | R | Name | Retention Time Min./Molecular Mass |
|---|---|---|---|
| 97 | —SO$_2$Et | N-((1S,2R,6R,7S,8R)-4-(4-cyano-3-(trifluoromethyl)phenyl)-2-methyl-3,3-dioxido-3-thia-4-azatricyclo[5.2.1.0$^{2,6}$]dec-8-yl)ethanesulfonamide | 2.88 LCMS [M − H]$^−$ = 476.26 |

Example 98

Rac-4-((1R,2S,6R,7R,10S)-10-hydroxy-2-methyl-3,3-dioxido-3-thia-4-azatricyclo[5.2.1.0$^{2,6}$]dec-8-en-4-yl)-2-(trifluoromethyl)benzonitrile

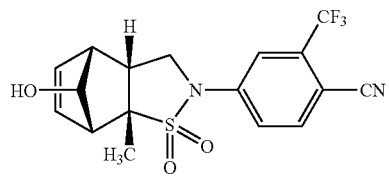

98A. 2,4-cyclopentadien-1-yl(dimethyl)phenylsilane

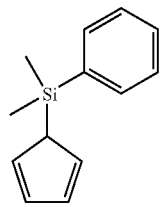

To a solution of sodium cyclopentadienylide (2.0 M in THF, 142 mL, 285 mmol) in THF (250 mL) at −78° C. was added a solution of chlorodimethylphenylsilane (50.0 g, 285 mmol) in THF (50 mL) via an addition funnel over 30 min. After addition was complete, the reaction was slowly warmed to 0° C. After 15 min at 0° C., the reaction was quenched with H$_2$O (50 mL) and then diluted with heptane (200 mL). The aqueous phase was extracted 1× with heptane (200 mL) and the organics combined. The combined organics were dried over anhydrous MgSO$_4$ and concentrated in vacuo to give 61.1 g 98A as a brown oil that was used without purification. HPLC: 86% at 4.253 min (retention time) (YMC ODS-A column 4.6×50 mm eluting with 10-90% aqueous MeOH over 4 min containing 0.1% H$_3$PO$_4$, 4 mL/min, monitoring at 220 nm).

98B. Rac-4-((1R,2S,6R,7R,10R)-10-(dimethyl(phenyl)silyl)-3,3-dioxido-5-oxo-3-thia-4-azatricyclo[5.2.1.0$^{2,6}$]dec-8-en-4-yl)-2-(trifluoromethyl)benzonitrile

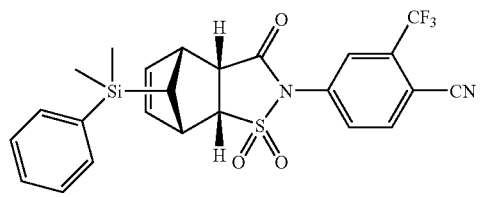

To a solution of 98A (2.00 g, 6.60 mmol) in THF (5 mL) was added 1D (2.64 g, 13.2 mmol). After 30 min. at 22° C. the reaction was complete and the mixture was concentrated in vacuo to give an orange oil. After drying under high vacuum for 14 hrs, a solid remained that was triturated with heptane to yield 3.3 g 98B (as a 9:1 mixture of endo and exo isomers) as a pale yellow solid that was used without purification. HPLC: 79% at 4.041 min (retention times) (YMC ODS-A column 4.6×50 mm eluting with 10-90% aqueous MeOH over 4 min containing 0.1% H$_3$PO$_4$, 4 mL/min, monitoring at 220 nm).

98C. Rac-4-((1R,2S,6R,7R,10R)-10-(dimethyl(phenyl)silyl)-3,3-dioxido-3-thia-4-azatricyclo[5.2.1.0$^{2,6}$]dec-8-en-4-yl)-2-(trifluoromethyl)benzonitrile

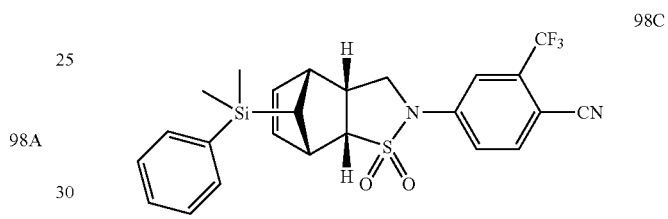

To solution of 98B (3.31 g, 6.61 mmol) in THF/MeOH (60 mL/6 mL) at 0° C. was added NaBH$_4$ (0.502 g, 13.2 mmol) resulting in vigorous gas evolution. After 10 min, the reaction was warmed to 22° C. After 1 hr at 22° C., the reaction was quenched by the addition of sat aq NH$_4$Cl (50 mL). The mixture was extracted 2× with EtOAc (100 mL) and the organics combined. The combined organics were washed 1× with brine (50 mL), dried over anhydrous MgSO$_4$, filtrated, and concentrated in vacuo to give a crude primary alcohol intermediate as a tan oil that was used without purification.

To a solution of the crude alcohol (~6.6 mmol) and triphenylphosphine (2.23 g, 8.58 mmol) in THF (75 mL) was added DIAD (1.69 mL, 8.58 mmol) over 5 min. After 30 min at 22° C., the reaction was complete and concentrated in vacuo to give an orange foam, which was purified by flash chromatography on silica eluting with a gradient of 50-100% methylene chloride in heptane to give 1.39 g of 98C as a white foam. HPLC: 98% at 4.08 min (retention times) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 547.36 [M−H+ OAc]$^−$.

98D. Rac-4-((1R,2S,6R,7R,10R)-10-(dimethyl(phenyl)silyl)-2-methyl-3,3-dioxido-3-thia-4-azatricyclo[5.2.1.0$^{2,6}$]dec-8-en-4-yl)-2-(trifluoromethyl)benzonitrile

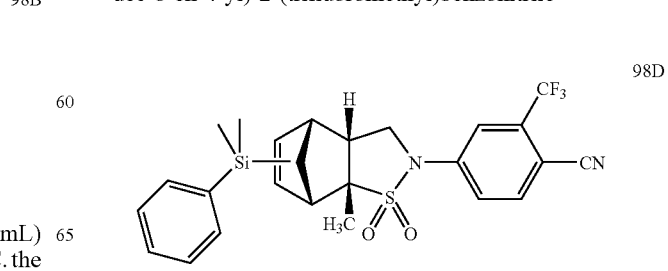

To a solution of 98C (0.485 g, 0.99 mmol) and methyl iodide (0.185 mL, 2.97 mmol) in THF (10 mL) at 0° C. was added LiHMDS (1.0 M soln in THF, 1.28 mL, 1.28 mmol). After 30 min, the reaction was complete and was quenched by the addition of sat aq NH$_4$Cl (10 mL). The solution was extracted 2× with EtOAc (50 mL) and the combined organics dried over anhydrous MgSO$_4$, filtrated, and then concentrated in vacuo to give 0.451 g 98D as a white foam. No purification was necessary. HPLC: 99% at 4.175 min (retention times) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 561.31 [M−H+ OAc]$^−$.

98E. Rac-4-((1R,2S,6R,7R,10S)-10-hydroxy-2-methyl-3,3-dioxido-3-thia-4-azatricyclo[5.2.1.0$^{2,6}$]dec-8-en-4-yl)-2-(trifluoromethyl)benzonitrile

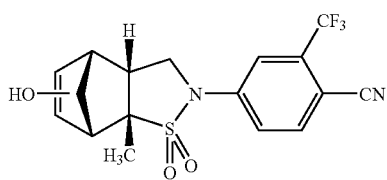

98E

To a solution of 98D (0.050 g, 0.102 mmol) in methylene chloride (1.5 mL) at 22° C. was added HBF$_4$-Et$_2$O (57% soln, 0.4 mL). After 4 hrs, the starting material was consumed and 1N HCl (1.0 mL) was added to the reaction. The reaction was stirred vigorously for 10 min. and the aqueous phase adjusted to pH>8.0 by the addition of 15% KOH. The solution was extracted 2× with methylene chloride (20 mL), and the combined organics were dried over anhydrous Na$_2$SO$_4$, filtered, and concentrated in vacuo to give the intermediate silyl fluoride.

The silyl fluoride was dissolved in dry DMF at 22° C. and then KF (0.059 g, 1.02 mmol) was added followed by H$_2$O$_2$ (30% in water, 0.032 mL, 0.306 mmol). The mixture was heated to 50° C. and after 6 hrs the reaction was complete. The mixture was diluted with EtOAc (50 mL); washed 1× with sat aq NH$_4$Cl (20 mL), 1× with H$_2$O, (20 mL), and 1× with brine (20 mL); and dried over anhydrous MgSO$_4$. The crude material was purified by preparative-TLC on silica eluting with 15% acetone in chloroform to give 0.011 g 98E as a white solid. HPLC: 99% at 2.705 min (retention time) (YMC ODS-A column 4.6×50 mm eluting with 10-90% aqueous MeOH over 4 min containing 0.1% H$_3$PO$_4$, 4 mL/min, monitoring at 220 nm); and MS (ES): m/z 433.21 [M−H+ OAc]$^−$.

What is claimed is:

1. A compound of the following formula (I):

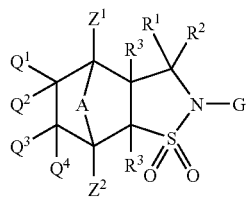

(I)

or a pharmaceutically-acceptable salt thereof;
wherein the symbols have the following meanings and are, for each occurrence, independently selected:

G is aryl, substituted aryl, heteroaryl, or substituted heteroaryl, wherein G is attached to the N atom of the core rings via a carbon atom of G;

A is CR$^4$R$^5$, C(=O), C(OR$^4$)R$^5$, CR$^4$R$^5$CR$^4$R$^5$, CR$^4$R$^5$C(=O), or CR$^4$R$^5$C(OR$^4$)R$^5$;

Z$^1$ and Z$^2$ are each independently H, halogen, CN, alkyl, substituted alkyl, alkenyl, substituted alkenyl, cycloalkyl, substituted cycloalkyl, cycloalkylalkyl, substituted cycloalkylalkyl, aryl, substituted aryl, arylalkyl, substituted arylalkyl, heterocyclo, substituted heterocyclo, heterocycloalkyl, substituted heterocycloalkyl, —C(=O)OR$^6$, —C(=O)R$^6$, —C(=O)NR$^6$R$^7$, —OC(=O)NR$^6$R$^7$, —OC(=O)R$^6$, —OR$^6$, —C(=N—CN)NR$^6$R$^7$, —NR$^6$C(=O)OR$^7$, —NR$^6$C(=O)R$^7$, —SO$_2$R$^7$, —NR$^6$R$^7$, —NR$^6$SO$_2$R$^7$, —NR$^6$SO$_2$NR$^6$R$^7$, and/or —NR$^6$C(=O)NR$^6$R$^7$;

Q$^1$, Q$^2$, Q$^3$, and Q$^4$ are each independently H, halogen, CN, alkyl, substituted alkyl, aryl, substituted aryl, heterocyclo, substituted heterocyclo, —OR$^6$, —NR$^6$R$^7$, —NR$^6$C(=O)OR$^7$, —OC(=O)NR$^6$R$^7$, —NR$^6$SO$_2$R$^7$, —SO$_2$R$^7$, —OSO$_2$R$^7$, —SO$_2$NR$^6$R$^7$, —NR$^6$SO$_2$NR$^6$R$^7$, —SR$^9$, —SOR$^9$, —C(=O)NR$^6$R$^7$, —C(=O)OR$^6$, —C(=O)R$^6$, —NR$^6$C(=O)R$^7$, and/or —NR$^6$C(=O)NR$^6$R$^7$; or Q$^1$ and Q$^2$ together form O and/or Q$^3$ and Q$^4$ together form O; or Q$^2$ and Q$^4$ together form CR$^6$R$^7$, O, NR$^8$, or a carbon-carbon bond;

R$^1$ and R$^2$ are each independently H, alkyl, substituted alkyl, cycloalkyl, substituted cycloalkyl, cycloalkylalkyl, substituted cycloalkylalkyl, alkenyl, substituted alkenyl, arylalkyl, substituted arylalkyl, heterocycloalkyl, substituted heterocycloalkyl, aryl, substituted aryl, heteroaryl, substituted heteroaryl, OH, and/or CN;

each R$^3$ is independently H, alkyl, substituted alkyl, alkenyl, substituted alkenyl, cycloalkyl, substituted cycloalkyl, cycloalkylalkyl, substituted cycloalkylalkyl, —COR$^6$, —CONR$^6$R$^7$, —OR$^6$, —C(=O)OR$^6$, —OC(=O)NR$^6$R$^7$, —SO$_2$R$^7$, —NR$^6$C(=O)R$^7$, —NR$^6$SO$_2$R$^7$, —NR$^6$C(=O)NR$^6$R$^7$, —NR$^6$C(=O)OR$^7$, and/or —NR$^6$R$^7$;

each R$^4$ and each R$^5$ are independently H, alkyl, substituted alkyl, cycloalkyl, substituted cycloalkyl, cycloalkylalkyl, substituted cycloalkylalkyl, arylalkyl, substituted arylalkyl, heterocycloalkyl, substituted heterocycloalkyl, aryl, substituted aryl, heteroaryl, substituted heteroaryl, and/or CN; or R$^4$ and R$^5$ together with the carbon atom to which they are attached form a cycloalkyl ring;

each R$^6$ and each R$^7$ are independently H, alkyl, substituted alkyl, cycloalkyl, substituted cycloalkyl, cycloalkylalkyl, substituted cycloalkylalkyl, arylalkyl, substituted arylalkyl, heterocycloalkyl, substituted heterocycloalkyl, aryl, substituted aryl, heteroaryl, substituted heteroaryl, and/or CN;

R$^8$ is H, alkyl, substituted alkyl, cycloalkyl, substituted cycloalkyl, cycloalkylalkyl, substituted cycloalkylalkyl, —C(=O)R$^6$, —C(=O)NR$^6$R$^7$, —C(=O)OR$^6$, —SO$_2$R$^7$, —SO$_2$NR$^6$R$^7$, or —SO$_3$R$^7$; and each R$^9$ is independently H, alkyl, substituted alkyl, cycloalkyl, substituted cycloalkyl, cycloalkylalkyl, substituted cycloalkylalkyl, arylalkyl, substituted arylalkyl, heterocycloalkyl, substituted heterocycloalkyl, aryl, substituted aryl, heteroaryl, and/or substituted heteroaryl;

with the proviso that when Q$^2$ and Q$^4$ together form a carbon-carbon bond and A$^1$ is CH$_2$, then G is not a phenyl group substituted at the 4-position with an oxygen-substituted methylene group or —C(=O)O-alkyl.

2. The compound according to claim 1 wherein:
G is substituted aryl or substituted heteroaryl;
A is $CR^4R^5$;
$Z^1$ and $Z^2$ are each independently H, lower alkyl, and/or substituted lower alkyl;
$Q^1, Q^2, Q^3$, and $Q^4$ are each independently H, halogen, CN, alkyl, substituted alkyl, —$OR^6$, —$NR^6R^7$, —$NR^6C(=O)OR^7$, —$OC(=O)NR^6R^7$, —$NR^6SO_2R^7$, —$SO_2R^7$, —$SO_2NR^6R^7$, —$NR^6SO_2NR^6R^7$, —$C(=O)NR^6R^7$, —$C(=O)OR^6$, —$C(=O)R^6$, —$NR^6C(=O)R^7$, and/or —$NR^6C(=O)NR^6R^7$; or $Q^1$ and $Q^2$ together form O and/or $Q^3$ and $Q^4$ together form O; or $Q^2$ and $Q^4$ together form $CR^6R^7$, O, $NR^8$, or a carbon-carbon bond;
$R^1$ and $R^2$ are each independently H, lower alkyl, and/or substituted lower alkyl;
each $R^3$ is independently H, lower alkyl, substituted lower alkyl, —$C(=O)NR^6R^7$, —$NR^6SO_2R^7$, —$NR^6C(=O)OR^7$, and/or —$SO_2R^7$;
each $R^4$ and each $R^5$ are independently H, lower alkyl, and/or substituted lower alkyl;
each $R^6$ and each $R^7$ are independently H, lower alkyl, and/or substituted lower alkyl;
$R^5$ is H, lower alkyl, substituted lower alkyl, —$C(=O)OR^6$, or —$SO_2R^7$; and
each $R^9$ is lower alkyl or substituted lower alkyl;
or a pharmaceutically-acceptable salt thereof.

3. The compound according to claim 2, wherein:
$Z^1$ and $Z^2$ are each independently H, methyl, —$CH_2OH$, —$CH_2CN$, —$CH_2SO_2R^{10}$ and/or —$CH_2NHC(=O)OR^{10}$; and
each $R^{10}$ is lower alkyl;
or a pharmaceutically-acceptable salt thereof.

4. The compound according to claim 2, wherein: A is $CH_2$ or CHOH,
or a pharmaceutically-acceptable salt thereof.

5. The compound according to claim 2, wherein:
$Q^1, Q^2, Q^3$, and $Q^4$ are each independently H, halogen, CN, lower alkyl, substituted lower alkyl, —$NR^6C(=O)OR^7$, —$NR^6SO_2R^7$, —$C(=O)NR^6R^7$, and/or —$NR^6C(=O)R^7$;
or a pharmaceutically-acceptable salt thereof.

6. The compound according to claim 2, wherein:
$Q^1$ and $Q^3$ are each independently H, halogen, CN, lower alkyl, substituted lower alkyl, —$NR^6C(=O)OR^7$, —$NR^6SO_2R^7$, —$C(=O)NR^6R^7$, and/or —$NR^6C(=O)R^7$; and
$Q^2$ and $Q^4$ together form a carbon-carbon bond;
or a pharmaceutically-acceptable salt thereof.

7. The compound according to claim 2, wherein:
G is a substituted phenyl, substituted naphthyl, substituted pyridyl, substituted quinoline, substituted isoquinoline, or substituted benzoxadiazol;
or a pharmaceutically-acceptable salt thereof.

8. The compound according to claim 7, wherein:
G is substituted with 1, 2, or 3 substituents;
or a pharmaceutically-acceptable salt thereof.

9. The compound according to claim 8, wherein:
G is substituted with 1, 2, or 3 substituents independently selected from —CN, Cl, Br, I, $CF_3$, methyl, and/or —$OR^{11}$; and
each $R^{11}$ is lower alkyl or substituted lower alkyl;
or a pharmaceutically-acceptable salt thereof.

10. The compound according to claim 2, wherein G is:

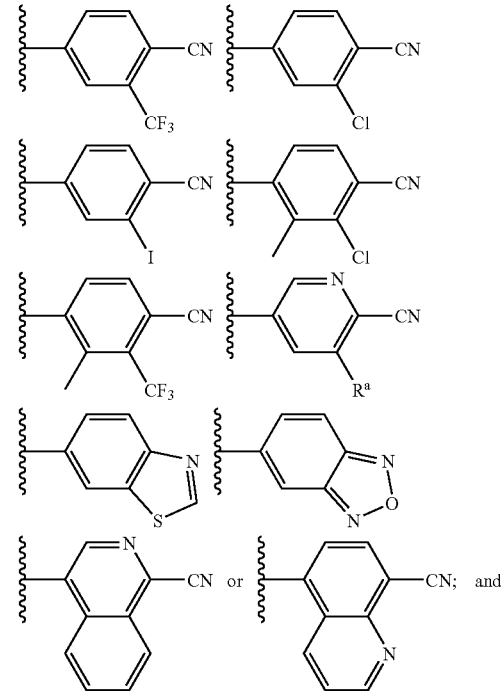

$R^a$ is alkyl, substituted alkyl, or —$OR^{11}$; and
$R^{11}$ is alkyl or substituted alkyl;
or a pharmaceutically-acceptable salt thereof.

11. A pharmaceutical composition comprising:
a) at least one compound according to claim 1 or a pharmaceutically-acceptable salt thereof;
b) optionally at least one pharmaceutically-acceptable carrier and/or diluent; and
c) optionally at least one other anti-cancer agent.

12. The compound according to claim 1 selected from:
4-((1S,2R,6R,7R)-3,3-dioxido-5-oxo-3-thia-4-azatricyclo[5.2.1.0²,⁶]dec-8-en-4-yl)-2-(trifluoromethyl)benzonitrile (1E); 4-((1S,2S,6S,7R)-3,3-dioxido-5-oxo-3-thia-4-azatricyclo[5.2.1.0²,⁶]dec-8-en-4-yl)-2-(trifluoromethyl)benzonitrile (1F); Rac-4-((1R,2S,6S,7S)-3,3-dioxido-3-thia-4-azatricyclo[5.2.1.0²,⁶]dec-8-en-4-yl)-2-(trifluoromethyl)benzonitrile (1K); Rac-4-((1R,2R,6R,7S)-3,3-dioxido-3-thia-4-azatricyclo[5.2.1.0²,⁶]dec-8-en-4-yl)-2-(trifluoromethyl)benzonitrile (1L); 4-((1S,2R,6R,7R)-3,3-dioxido-3-thia-4-azatricyclo[5.2.1.0²,⁶]dec-8-en-4-yl)-2-(trifluoromethyl)benzonitrile (2); 4-((1R,2S,6S,7S)-3,3-dioxido-3-thia-4-azatricyclo[5.2.1.0²,⁶]dec-8-en-4-yl)-2-(trifluoromethyl)benzonitrile (3); 4-((1R,2R,6R,7S)-3,3-dioxido-3-thia-4-azatricyclo[5.2.1.0²,⁶]dec-4-yl)-2-(trifluoromethyl)benzonitrile (4); 4-((1S,2S,6S,7R)-3,3-dioxido-3-thia-4azatricyclo[5.2.1.0²,⁶]dec-4-yl)-2-(trifluoromethyl)benzonitrile (5); 4-((1S,2S,6R,7R,9S)-9hydroxy-3,3-dioxido-3-thia-4-azatricyclo[5.2.1.0²,⁶]dec-4-yl)-2-(trifluoromethyl)benzonitrile (6A); 4-((1S,2R,6R,7S,8R)-8-hydroxy-3,3-dioxido-3-thia-4-azatricyclo[5.2.1.0²,⁶]dec-4-yl)-2-(trifluoromethyl)benzonitrile (6B); 4-((1R,2S,6S,7R,8S)-8-hydroxy-3,3-dioxido-3-thia-4-azatricyclo[5.2.1.0²,⁶]dec-4-yl)-2-(trifluoromethyl)benzonitrile (7A); 4-((1R,2R,6S,7S,9R)-9-hydroxy-3,3-dioxido-3-thia-4-azatricyclo[5.2.1.0²,⁶]dec-4-yl)-2-(trifluoromethyl)benzonitrile (7B); 4-((1S,2S,6R,7R)-3,3-dioxido-9-oxo-3-thia-4-azatricyclo[5.2.1.0$^{2,6}$]dec-4-yl)-2-(trifluoromethyl)benzonitrile (8); 4-((1R,2R,6S,7S)-3,3-dioxido-9-oxo-3-thia-4azatricyclo[5.2.1.0$^{2,6}$]dec-4-yl)-2-(trifluoromethyl)benzonitrile (9); 4-((1S,2S,6R,7R,9R)-9-(benzylamino)-3,3-dioxido-3-thia-4-azatricyclo[5.2.1.0$^{2,6}$]dec-4-yl)-2-(trifluoromethyl)benzonitrile (10); 4-((1R,2S,6S,7R,9S)-3,3-dioxido-9-(2-phenylethyl)-3-thia-4-azatricyclo[5.2.1.0$^{2,6}$]dec-4-yl)-2-(trifluoromethyl)benzonitrile (11); 4-((1S,2S,6R, 7R,9R)-9-hydroxy-3,3-dioxido-3-thia-4-azatricyclo[5.2.1.0$^{2,6}$]dec-4-yl)-2-(trifluoromethyl)benzonitrile (12); 4-((1R,2R,6S,7S, 9S)-9-hydroxy-3,3-dioxido-3-thia-4-azatricyclo[5.2.1.0$^{2,6}$]dec-4-yl)-2-(trifluoromethyl)benzonitrile (13); Rac-4-((1R, 2R,6S,7R,8R,9S)-8,9-dihydroxy-3,3-dioxido-3-thia-4-azatricyclo[5.2.1.0$^{2,6}$]dec-4-yl)-2-(trifluoromethyl)benzonitrile (14); Rac-4-((1R,2R,6S,7R,8R,10S)-3,3-dioxido-9-oxa-3-thia-4-azatetracyclo[5.3.1.0$^{2,6}$.0$^{8,10}$]undec-4-yl)-2-(trifluoromethyl)benzonitrile (15); 4-((1S,2S,6R,7R, 9S)-9-fluoro-3,3-dioxido-3-thia-4azatricyclo[5.2.1.0$^{2,6}$]dec-4-yl)-2-(trifluoromethyl)benzonitrile (17); 4-((1R,2R,6S,7S, 9R)-9-fluoro-3,3-dioxido-3-thia-4-azatricyclo[5.2.1.0$^{2,6}$]dec-4-yl)-2-(trifluoromethyl)benzonitrile (18); 4-((1S,2S,6R,7R,9S)-9-methoxy-3,3-dioxido-3-thia-4-azatricyclo[5.2.1.0$^{2,6}$]dec-4-yl)-2-(trifluoromethyl)benzonitrile (19); 4-((1R,2R,6S,7S,9R)-9-methoxy-3,3-dioxido-3-thia-4-azatricyclo[5.2.1.0$^{2,6}$]dec-4-yl)-2-(trifluoromethyl)benzonitrile (20); Rac-4-((1S,2S,6R,7S,8R,9R)-8-chloro-9-hydroxy-3,3-dioxido-3-thia-4-azatricyclo[5.2.1.0$^{2,6}$]dec-4-yl)-2-(trifluoromethyl)benzonitrile (21); 4-((1S,2R,6R,7R)-2-methyl-3,3-dioxido-3-thia-4-azatricyclo[5.2.1.0$^{2,6}$]dec-8-en-4-yl)-2-(trifluoromethyl)benzonitrile (22); 4-((1R,2S,6S,7S)-2-methyl-3,3-dioxido-3-thia-4-azatricyclo[5.2.1.0$^{2,6}$]dec-8-en-4-yl)-2-(trifluoromethyl)benzonitrile (23); 4-((1R,2R,6R,7S)-2-methyl-3,3-dioxido-3-thia-4-azatricyclo[5.2.1.0$^{2,6}$]dec-4-yl)-2-(trifluoromethyl)benzonitrile (24); 4-((1R,2R,6R,7S)-2-ethyl-3,3-dioxido-3-thia-4-azatricyclo[5.2.1.0$^{2,6}$]dec-4-yl)-2-(trifluoromethyl)benzonitrile (25); 4-((1R,2R,6R,7S)-2-allyl-3,3-dioxido-3-thia-4-azatricyclo[5.2.1.0$^{2,6}$]dec-4-yl)-2-(trifluoromethyl)benzonitrile(26); 4-((1R,2R,6R,7S)-2-ethyl-3,3-dioxido-3-thia-4-azatricyclo[5.2.1.0$^{2,6}$]dec-4-yl)-2-(trifluoromethyl)benzonitrile (27); 4-((1S,2S,6S,7R)-2-ethyl-3,3-dioxido-3-thia-4-azatricyclo[5.2.1.0.$^{2,6}$]dec-4-yl)-2-(trifluoromethyl)benzonitrile (28); 4-((1S,2S,6S,7R)-2-allyl-3,3-dioxido-3-thia-4-azatricyclo[5.2.1.0$^{2,6}$]dec-4-yl)-2-(trifluoromethyl)benzonitrile (29); 4-((1S,2R,6R,7R)-2-((benzyloxy)methyl)-3,3-dioxido-3-thia-4-azatricyclo[5.2.1.0$^{2,6}$]dec-8-en-4-yl)-2-(trifluoromethyl)benzonitrile (30); 4-((1R,2R,6R,7S)-2-((benzyloxy)methyl)-3,3-dioxido-3-thia-4-azatricyclo[5.2.1.0$^{2,6}$]dec-4-yl)-2-(trifluoromethyl)benzonitrile (31); 4-((1R,2R,6R,7S)-2-(hydroxymethyl)-3,3-dioxido-3-thia-4-azatricyclo[5.2.1.0$^{2,6}$]dec-4-yl)-2-(trifluoromethyl)benzonitrile (32); 4-((1S,2R,6R,7R)-2-(methoxymethyl)-3,3-dioxido-3-thia-4-azatricyclo[5.2.1.0$^{2,6}$]dec-8-en-4-yl)-2-(trifluoromethyl)benzonitrile (33); 4-((1R,2R,6R,7S)-2-(methoxymethyl)-3,3-dioxido-3-thia-4-azatricyclo[5.2.1.0$^{2,6}$]dec-4-yl)-2-(trifluoromethyl)benzonitrile (34); 4-((1S,2S,6R,7R,9S)-9-hydroxy-2-(methoxymethyl)-3,3-dioxido-3-thia-4-azatricyclo[5.2.1.0$^{2,6}$]dec-4-yl)-2-(trifluoromethyl)benzonitrile (35A); 4-((1S,2R,6R,7S,8R)-8-hydroxy-2-(methoxymethyl)-3,3-dioxido-3-thia-4-azatricyclo[5.2.1.0$^{2,6}$]dec-4-yl)-2-(trifluoromethyl)benzonitrile (35B); Ethyl rac-(1R,2S,6S,7S)-4-(4-cyano-3-(trifluoromethyl)phenyl)-3-thia-4-azatricyclo[5.2.1.0$^{2,6}$]dec-8-ene-2-carboxylate 3,3-dioxide (36); 4-((1S,2S,6R,7R,9S)-9-hydroxy-2-methyl-3,3-dioxido-3-thia-4-azatricyclo[5.2.1.0$^{2,6}$]dec-4-yl)-2-(trifluoromethyl)benzonitrile (37A); 4-((1S,2R,6R,7S,8R)-8-hydroxy-2-methyl-3,3dioxido-3-thia-4-azatricyclo[5.2.1.0$^{2,6}$]dec-4-yl)-2-(trifluoromethyl)benzonitrile (37B); 4-((1S,2S,6R,7R,9S)-9-fluoro-2-methyl-3,3-dioxido-3-thia-4-azatricyclo[5.2.1.0$^{2,6}$]dec-4-yl)-2-(trifluoromethyl)benzonitrile (38); 4-((1R,2R,6S,7S,9R)-9-fluoro-2-methyl-3,3-dioxido-3-thia-4-azatricyclo[5.2.1.0$^{2,6}$]dec-4-yl)-2-(trifluoromethyl)benzonitrile (39); Rac-4-((1S,2R, 6R, 7R)-5-hydroxy-3,3-dioxido-3-thia-4-azatricyclo[5.2.1.0$^{2,6}$]dec-8-en-4-yl)-2-(trifluoromethyl)benzonitrile (40A); Rac-4-((1R,2S,5 S,6S,7S)-5-allyl-3,3-dioxido-3-thia-4-[5.2.1.0$^{2,6}$] dec-8-en-4-yl)-2-(trifluoromethyl)benzonitrile (40B); Rac-4-((1R,2R,5R,6R,7S)-3,3-dioxido-5-propyl-3-thia-4-azatricyclo[5.2.1.0$^{2,6}$]dec-4-yl)-2-(trifluoromethyl)benzonitrile (41); Rac-4-((1R,2R,5R,6R,7S)-2-methyl-3,3-dioxido-5-propyl-3-thia-4-azatricyclo[5.2.1.0$^{2,6}$]dec-4-yl)-2-(trifluoromethyl)benzonitrile (42); Rac-4-((1R,2S,5S,6S, 7S)-5-methyl-3,3-dioxido-3-thia-4-azatricyclo[5.2.1.0$^{2,6}$]dec-8-en-4-yl)-2-(trifluoromethyl)benzonitrile (43); Rac-4 ((1R,2R,5R,6R,7S)-5-methyl-3,3-dioxido-3-thia-4-azatricyclo[5.2.1.0$^{2,6}$]dec-4-yl)-2-(trifluoromethyl) benzonitrile (44); Rac-4-((1R,2R,5R,6R,7S)-2,5-dimethyl-3,3-dioxido-3-thia-4-azatricyclo[5.2.1.0$^{2,6}$]dec-4-yl)-2-(trifluoromethyl)benzonitrile (45); Rac-4((1R,2R,5S,6S,7S, 9R)-9-hydroxy-5-methyl-3,3-dioxido-3-thia-4-azatricyclo [5.2.1.0$^{2,6}$]dec-4-yl)-2-(trifluoromethyl)benzonitrile (46A); Rac-4-((1R,2S,5S,6S,7R,8S)-8-hydroxy-5methyl-3,3-dioxido-3-thia-4-azatricyclo[5.2.1.0$^{2,6}$]dec-4-yl)-2-(trifluoromethyl)benzonitrile (46B); 4((1S,2R,6R,7S)-3,3-dioxido-8-oxo-3-thia-4-azatricyclo[5.2.1.0$^{2,6}$]dec-4-yl)-2-(trifluoromethyl)benzonitrile (47); 4-((1S,2R,6R,7S,8S)-8-hydroxy-3,3-dioxido-8-phenyl-3-thia-4-azatricyclo [5.2.1.0$^{2,6}$]dec-4-yl)-2-(trifluoromethyl)benzonitrile (48); 4-((1S,2R,6R,7S,8S)-8-hydroxy-3,3-dioxido-3-thia-4-azatricyclo[5.2.1.0$^{2,6}$]dec-4-yl)-2-(trifluoromethyl)benzonitrile (49); Rac-2-chloro-4-((1S,2R,6R,7R)-3,3-dioxido-3-thia-4-azatricyclo[5.2.1.0$^{2,6}$]dec-8-en-4-yl)-3-methylbenzonitrile (50D); Rac-2-chloro-4-((1S,2S,6S,7R)-3,3-dioxido-3-thia-4-azatricyclo [5.2.1.0$^{2,6}$]dec-8-en-4-yl)-3-methylbenzonitrile (50E); Rac-2-chloro-4-((2'S,6'S)-3',3'-dioxido-3'-thia-4'-azaspiro[cyclopropane-1,10'-tricyclo[5.2.1.0$^{2,6}$]decane]-8'-en-4'-yl)-3-methylbenzonitrile (51); Rac-2-chloro-4-((2R, 6R)-3,3-dioxido-3-thia-4-azatricyclo[5.2.2.0$^{2,6}$]undec-8-en-4-yl)-3-methylbenzonitrile (53); Rac-2-chloro-4-((1R,2S, 6R,7R,9S)-9-hydroxy-3,3-dioxido-3-thia-4-azatricyclo [5.2.1.0$^{2,6}$]dec-4-yl)-3-methylbenzonitrile (54); Rac-2-chloro-4-((1R,2S,6R,7S,8S,10R)-3,3-dioxido-9-oxa-3-thia-4-azatetracyclo[5.3.1.0$^{2,6}$.0$^{8,10}$]undec-4-yl)-3-methylbenzonitrile (55); Rac-2-chloro-4-((1R,2R,6R,7S)-3,3-dioxido-3-thia-4-azatricyclo[5.2.1.0$^{2,6}$]dec-4-yl)-3-methylbenzonitrile (56); 4-((1S,2S,6R,7S, 8S,10R)-2((benzyloxy)methyl)-3,3-dioxido-9-oxa-3-thia-4-azatetracyclo[5.3.1.0$^{2,6}$.0$^{8,10}$]undec-4-yl)-2-(trifluoromethyl)benzonitrile (57); 4-((1S,2S,6R,7S,8S, 10R)-2-(hydroxymethyl)-3,3-dioxido-9-oxa-3-thia-4-azatetracyclo[5.3.1.0$^{2,6}$.0$^{8,10}$]undec-4-yl)-2-(trifluoromethyl)benzonitrile (58); 4-((1S,2S,6R,7R,9S)-9-hydroxy-3,3-dioxido-2-(((phenylmethyl)oxy)methyl)-3-thia-4-azatricyclo[5.2.1.0$^{2,6}$]dec-4-yl)-2-(trifluoromethyl)benzonitrile (59); 4-((1S,2S,6R, 7R,9S)-9-hydroxy-2-(hydroxymethyl)-3,3-dioxido-3-thia-4-azatricyclo[5.2.1.0$^{2,6}$]dec-4-yl)-2-(trifluoromethyl)benzonitrile (60); ((1R,2R,6R,7S)-4-(4-cyano-3-(trifluoromethyl)phenyl)-3,3-dioxido-3-thia-4-azatricyclo[5.2.1.0$^{2,6}$]dec-2-yl)methyl trifluoromethanesulfonate (61); 4-((1R,2R,6R,7S)-2-(((4-fluorophenyl)sulfanyl)methyl)-3,3-dioxido-3-thia-4-azatricyclo[5.2.1.0$^{2,6}$]dec-4-yl)-2-(trifluoromethyl)benzonitrile (62); 4-((1R,2R,6R,7S)-2-(((4-fluorophenyl)sulfonyl)methyl)-3,3-dioxido-3-thia-4-azatricyclo[5.2.1.0$^{2,6}$]dec-4-yl)-

2-(trifluoromethyl)benzonitrile (63); 4-((1R,2R,6R,7S)-2-(cyanomethyl)-3,3-dioxido-3-thia-4-azatricyclo[5.2.1.0$^{2,6}$]dec-4-yl)-2-(trifluoromethyl)benzonitrile (64); 4-((1R,2R,6R,7S)-2-(aminomethyl)-3,3-dioxido-3-thia-4-azatricyclo[5.2.1.0$^{2,6}$]dec-4-yl)-2-(trifluoromethyl)benzonitrile (66); Methyl (((1R,2R,6R,7S)-4-(4-cyano-3-(trifluoromethyl)phenyl)-3,3-dioxido-3-thia-4-azatricyclo[5.2.1.0$^{2,6}$]dec-2-yl)methyl)carbamate (67); N-(((1R,2R,6R,7S)-4-(4-cyano3-(trifluoromethyl)phenyl)-3,3-dioxido-3-thia-4-azatricyclo[5.2.1.0$^{2,6}$]dec-2-yl)methyl)ethanesulfonamide (68); N-(((1R,2R,6R,7S)-4-(4-cyano-3-(trifluoromethyl)phenyl)-3,3-dioxido-3-thia-4-azatricyclo[5.2.1.0$^{2,6}$]dec-2-yl)methyl)-4-(methyloxy)benzamide (69); 4-((1S,2R,6R,7R)-3,3-dioxido-2-(((phenylmethyl)oxy)methyl)-3-thia-4-azatricyclo[5.2.1.0$^{2,6}$]dec-8-en-4-yl)-2-(trifluoromethyl)benzonitrile (70); Methyl (1S,2R,6R,7R)-4-(4-cyano-3-(trifluoromethyl)phenyl)-3-thia-4-azatricyclo[5.2.1.0$^{2,6}$]dec-8-ene-2-carboxylate 3,3-dioxide (71); (1R,2R,6R,7S)-4-(4-cyano-3-(trifluoromethyl)phenyl)-3-thia-4-azatricyclo[5.2.1.0$^{2,6}$]decane-2-carboxylic acid 3,3-dioxide (72); (1R,2R,6R,7S)-4-(4-cyano-3-(trifluoromethyl)phenyl)-3-thia-4-azatricyclo[5.2.1.0$^{2,6}$]decane-2-carbonyl chloride 3,3-dioxide (73); (1R,2R,6R,7S)-4-(4-cyano-3-(trifluoromethyl)phenyl)-3-thia-4-azatricyclo[5.2.1.0$^{2,6}$]decane-2-carboxamide 3,3-dioxide (74); (1R,2R,6R,7S)-N-benzyl-4-(4-cyano-3-(trifluoromethyl)phenyl)-3-thia-4-azatricyclo[5.2.1.0$^{2,6}$]decane-2-carboxamide 3,3-dioxide (75); (1R,2R,6R,7S)-4-(4-cyano-3-(trifluoromethyl)phenyl)-N-(4-methoxybenzyl)-3-thia-4-azatricyclo[5.2.1.0$^{2,6}$]decane-2-carboxamide 3,3-dioxide (76); (1R,2R,6R,7S)-4-(4-cyano-3-(trifluoromethyl)phenyl)-N-((1S)-1-phenylethyl)-3-thia-4-azatricyclo[5.2.1.0$^{2,6}$]decane-2-carboxamide 3,3-dioxide (77); (1R,2R,6R,7S)-4-(4-cyano-3-(trifluoromethyl)phenyl)-N-methyl-3-thia-4-azatricyclo[5.2.1.0$^{2,6}$]decane-2-carboxamide 3,3-dioxide (78); (1R,2R,6R,7S)-4-(4-cyano-3-(trifluoromethyl)phenyl)-N,N-dimethyl-3-thia-4-azatricyclo[5.2.1.0$^{2,6}$]decane-2-carboxamide 3,3-dioxide (79); 4-((1S,2S,6R,7S,8S,10R)-2-methyl-3,3-dioxido-9-oxa-3-thia-4-azatetracyclo[5.3.1.0$^{2,6}$.0$^{8,10}$]undec-4-yl)-2-(trifluoromethyl)benzonitrile (80); 4-((1S,2S,6R,7S,8S,9R)-8,9-dihydroxy-2-methyl-3,3-dioxido-3-thia-4-azatricyclo[5.2.1.0$^{2,6}$]dec-4-yl)-2-(trifluoromethyl)benzonitrile (81); 4-((1S,2S,6R,7R)-2-methyl-3,3-dioxido-9-oxo-3-thia-4-azatricyclo[5.2.1.0$^{2,6}$]dec-4-yl)-2-(trifluoromethyl)benzonitrile (82); 4-((1S,2R,6R,7S)-2-methyl-3,3-dioxido-8-oxo-3-thia-4-azatricyclo[5.2.1.0$^{2,6}$]dec-4-yl)-2-(trifluoromethyl)benzonitrile (83); 4-((1S,2S,6R,7R,9R)-9-hydroxy-2-methyl-3,3-dioxido-3-thia-4-azatricyclo[5.2.1.0$^{2,6}$]dec-4-yl)-2-(trifluoromethyl)benzonitrile (84); 4-((1S,2R,6R,7S,8S)-8-hydroxy-2-methyl-3,3-dioxido-3-thia-4-azatricyclo[5.2.1.0$^{2,6}$]dec-4-yl)-2-(trifluoromethyl)benzonitrile (85); (1S,2S,6R,7R,9R)-4-(4-cyano-3-(trifluoromethyl)phenyl)-2-methyl-3,3-dioxido-3-thia-4-azatricyclo[5.2.1.0$^{2,6}$]dec-9-yl trifluoromethanesulfonate (86); (1S,2R,6R,7S,8S)-4-(4-cyano-3-(trifluoromethyl)phenyl)-2-methyl-3,3-dioxido-3-thia-4-azatricyclo[5.2.1.0$^{2,6}$]dec-8-yl trifluoromethanesulfonate (87); (1S,2R,6R,7S,9S)-4-(4-cyano-3-(trifluoromethyl)phenyl)-2-methyl-3-thia-4-azatricyclo[5.2.1.0$^{2,6}$]decane-9-carbonitrile 3,3-dioxide (88); (1S,2R,6R,7R,8R)-4-(4-cyano-3-(trifluoromethyl)phenyl)-2-methyl-3-thia-4-azatricyclo[5.2.1.0$^{2,6}$]decane-8-carbonitrile 3,3-dioxide (89); 4-((1S, 2S,6R,7R,9S)-9-amino-2-methyl-3,3-dioxido-3-thia-4-azatricyclo[5.2.1.0$^{2,6}$]dec-4-yl)-2-(trifluoromethyl)benzonitrile (91); 4-((1S,2R,6R,7S,8R)-8-amino-2-methyl-3,3-dioxido-3-thia-4-azatricyclo[5.2.1.0$^{2,6}$]dec-4-yl)-2-(trifluoromethyl)benzonitrile (92); N-((1S,2R,6R,7S,8R)-4-(4-cyano-3-(trifluoromethyl)phenyl)-2-methyl-3,3-dioxido-3-thia-4-azatricyclo[5.2.1.0$^{2,6}$]dec-8-yl)acetamide (93); Propyl ((1S,2R,6R,7S,8R)-4-(4-cyano-3-(trifluoromethyl)phenyl)-2-methyl-3,3-dioxido-3-thia-4-azatricyclo[5.2.1.0$^{2,6}$]dec-8-yl)carbamate (94); N-((1S,2R,6R,7S,8R)-4-(4-cyano-3-(trifluoromethyl)phenyl)-2-methyl-3,3-dioxido-3-thia-4-azatricyclo[5.2.1.0$^{2,6}$]dec-8-yl)acetamide (95); 1-((1S,2R,6R,7S,8R)-4-(4-cyano-3-(trifluoromethyl)phenyl)-2-methyl-3,3-dioxido-3-thia-4-azatricyclo[5.2.1.0$^{2,6}$]dec-8-yl)-3-isopropylurea (96); N-((1S,2R,6R,7S,8R)-4-(4-cyano-3-(trifluoromethyl)phenyl)-2-methyl-3,3-dioxido-3-thia-4-azatricyclo[5.2.1.0$^{2,6}$]dec-8-yl)ethanesulfonamide (97); and Rac-4-((1R,2S,6R,7R,10S)-10-hydroxy-2-methyl-3,3-dioxido-3-thia-4-azatricyclo[5.2.1.0$^{2,6}$]dec-8-en-4-yl)-2-(trifluoromethyl)benzonitrile (98E).

\* \* \* \* \*

UNITED STATES PATENT AND TRADEMARK OFFICE
CERTIFICATE OF CORRECTION

PATENT NO. : 7,468,439 B2
APPLICATION NO. : 11/850070
DATED : December 23, 2008
INVENTOR(S) : Shan et al.

It is certified that error appears in the above-identified patent and that said Letters Patent is hereby corrected as shown below:

In Column 91, Line 24,
"$R^5$ is H, lower alkyl, substituted lower alkyl, -C(=O)" should read:
-- $R^8$ is H, lower alkyl, substituted lower alkyl, -C(=O) --

Signed and Sealed this

Twenty-fourth Day of March, 2009

JOHN DOLL
*Acting Director of the United States Patent and Trademark Office*